United States Patent
Augeri et al.

(10) Patent No.: US 10,828,288 B2
(45) Date of Patent: Nov. 10, 2020

(54) HYDRAZONE DERIVATIVES FOR THE TREATMENT OF CANCER

(71) Applicants: RUTGERS, THE STATE UNIVERSITY OF NEW JERSEY, New Brunswick, NJ (US); THE RESEARCH FOUNDATION FOR THE STATE UNIVERSITY OF NEW YORK, Syracuse, NY (US)

(72) Inventors: David J. Augeri, New Brunswick, NJ (US); Anthony F. Bencivenga, New Brunswick, NJ (US); Adam Blanden, Syracuse, NY (US); Darren R. Carpizo, New Brunswick, NJ (US); John A. Gilleran, New Brunswick, NJ (US); Spencer David Kimball, New Brunswick, NJ (US); Stewart N. Loh, Syracuse, NY (US); Xin Yu, New Brunswick, NJ (US)

(73) Assignees: Rutgers, the State University of New Jersey, New Brunswick, NJ (US); The Research Foundation for the State University of New York, Syracuse, NY (US)

(*) Notice: Subject to any disclaimer, the term of this patent is extended or adjusted under 35 U.S.C. 154(b) by 0 days.

(21) Appl. No.: 15/545,971

(22) PCT Filed: Jan. 27, 2016

(86) PCT No.: PCT/US2016/015195
§ 371 (c)(1),
(2) Date: Jul. 24, 2017

(87) PCT Pub. No.: WO2016/123253
PCT Pub. Date: Aug. 4, 2016

(65) Prior Publication Data
US 2018/0000806 A1  Jan. 4, 2018

Related U.S. Application Data

(60) Provisional application No. 62/108,415, filed on Jan. 27, 2015, provisional application No. 62/258,256, filed on Nov. 20, 2015.

(51) Int. Cl.
| | | |
|---|---|---|
| A61K 31/4439 | (2006.01) | |
| A61K 31/4427 | (2006.01) | |
| C07D 513/04 | (2006.01) | |
| C07D 417/12 | (2006.01) | |
| C07D 403/12 | (2006.01) | |
| C07D 401/12 | (2006.01) | |
| C07D 413/12 | (2006.01) | |

(52) U.S. Cl.
CPC ...... *A61K 31/4439* (2013.01); *A61K 31/4427* (2013.01); *C07D 401/12* (2013.01); *C07D 403/12* (2013.01); *C07D 413/12* (2013.01); *C07D 417/12* (2013.01); *C07D 513/04* (2013.01)

(58) Field of Classification Search
None
See application file for complete search history.

(56) References Cited

U.S. PATENT DOCUMENTS

| | | | |
|---|---|---|---|
| 4,665,173 A | 5/1987 | Klayman et al. | |
| 7,112,680 B2 * | 9/2006 | Hofmann | C07D 401/12 546/273.4 |
| 10,221,133 B2 | 3/2019 | Augeri et al. | |
| 2008/0118576 A1 * | 5/2008 | Theodorescu | A61K 31/337 424/649 |
| 2013/0345164 A1 | 12/2013 | Vazquez et al. | |
| 2014/0142266 A1 * | 5/2014 | Sakamoto | C07D 215/38 526/257 |
| 2018/0000772 A1 | 1/2018 | Augeri et al. | |

(Continued)

FOREIGN PATENT DOCUMENTS

| | | | |
|---|---|---|---|
| JP | 49126728 | * | 12/1974 |
| WO | 2001094340 A1 | | 12/2001 |
| WO | 2006019955 A2 | | 2/2006 |

(Continued)

OTHER PUBLICATIONS

Vartale et al. in Indian Journal of Heterocyclic Chemistry 16(2), 163-166 (2006) (Year: 2006).*

(Continued)

*Primary Examiner* — Dennis Heyer
(74) *Attorney, Agent, or Firm* — Viksnins Harris Padys Malen LLP

(57) ABSTRACT

The invention provides compounds of formula (I): and salts thereof wherein ring A, $R^2$, HET, X, n, and $R^3$ have any of the meanings described in the specification, as well as compositions comprising such compounds and salts, and methods for treating cancer using such compounds and salts.

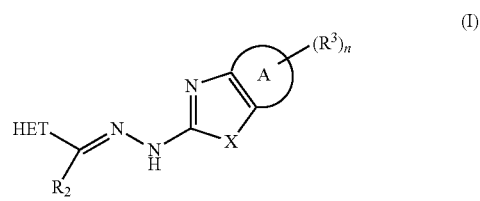

14 Claims, 2 Drawing Sheets

(56) References Cited

U.S. PATENT DOCUMENTS

| | | |
|---|---|---|
| 2018/0002279 A1 | 1/2018 | Augeri et al. |
| 2018/0002280 A1 | 1/2018 | Augeri et al. |

FOREIGN PATENT DOCUMENTS

| | | |
|---|---|---|
| WO | 2006101740 A2 | 9/2006 |
| WO | 2007035489 A2 | 3/2007 |
| WO | 2009039553 A1 | 4/2009 |
| WO | 2012175962 A1 | 12/2012 |
| WO | 2015021456 A1 | 2/2015 |
| WO | 2016123242 A1 | 8/2016 |
| WO | 2016123246 A1 | 8/2016 |
| WO | 2016123250 A1 | 8/2016 |

OTHER PUBLICATIONS

Gudasi et al. in Transition Metal Chemistry 30:726-732 (2005) (Year: 2005).*

Easmon et al. in European Journal of Medicinal Chemistry 32, 397-408 (1997) (Year: 1997).*

Agrawal, et al., "Potential antitumor agents. 13. 4-Methy1-5-amino-1-formylisoquinoline thiosemicarbazone", Journal of Medicinal Chemistry 19(7), 970-972 (1976).

Agrawal, et al., "Potential antitumor agents. 13. 4-Methyl-5-amino-1-formylisoquinoline thiosemicarbazone", Journal of Medicinal Chemistry 19(7), 970-972 (1976).

Antonini, et al., "Elucidation of the structure of the antineoplastic agents, 2-formylpyridine and 1-formylisoquinoline thiosemicarbazones", Journal of Medicinal Chemistry 20(3), 447-449 (1977).

Bellitto, et al., "Conformational Studies of Some Potentially Bidentate Thiosemicarba-zones and Related Complexes of Zinc(II)", J.C.S. Dalton 68570(21), 758-762 (1976).

Chun-Ying, et al., "Synthesis, Crystal Structure and Nonlinear Optical Properties of Thiosemicarbazone Zinc Complex", J Coord Chem 47, 433-439 (1999).

Easmon, et al., "2-benzoxazolyl and 2-benzimidazolyl hydrazones derived from 2-acetylpyridine: a novel class of antitumor agents", Int J Cancer 94, 89-96 (2001).

Easmon, et al., "Synthesis, Structure—Activity Relationships, and Antitumor Studies of 2-Benzoxazolyl Hydrazones Derived from Alpha-(N)-acyl Heteroaromatics", J Med Chem 49, 6343-6350 (2006).

Easmon, et al., "Thiazolyl and benzothiazolyl hydrazones derived from α-(N)-acetylpyridines and diazines: synthesis, antiproliferative activity and CoMFA studies", Eur J Med Chem 32, 397-408 (1997).

File Caplus, "Preparation and characterization of vanillin thiosemicarbazone complexes with cobalt(II), nickel(II), copper(II), zinc(II), cadmium(II), and mercury(II)", STN CA Caesar Accession No. 1170, 2 pages (1984).

File Caplus, "Synthesis and crystal structure of zinc(II) complex [Zn(25-MBTSC)2I2]", STN CA Caesar Accession No. 1162, 1 page (2013).

File Caplus, "Synthesis and structure of 1.5Zn(phen)3.cntdot.L. cntdot . . . 3N03 supramolecule (phen = o-phenanthroline, L = 4-aminoacetophenone thiosemicarbazone", STN CA Caesar Accession No. 1176, 2 pages (2008).

Hall, et al., "Investigations on the Mechanism of Action of the Novel Antitumor Agents 2-Benzothiazolyl, 2-Benzoxazolyl, and 2-Benzimidazolyl Hydrazones Derived from 2-Acetylpyridine", Arch Pharm Pharm Med Chem 332 (4), 115-123 (1999).

Huang, et al., "A Series of α-Heterocyclic Carboxaldehyde Thiosemicarbazones Inhibit Topoisomerase IIα Catalytic Activity", Journal of Medicinal Chemistry 53, 3048-3064 (2010).

Huang, et al., "Correlating gene expression with chemical scaffolds of cytotoxic agents: ellipticines as substrates and inhibitors of MDR1", Pharmacogenomics Journal 5, 112-125 (2005).

Ibrahim, et al., "Indole-7-carbaldehyde thiosemicarbazone as a flexidentate ligand toward ZnII, CdII, PdII and PtII ions: cytotoxic and apoptosis-inducing properties of the PtII complex", Dalton Trans 43, 3860-3860 (2014).

Kalinowski, et al., "Design, Synthesis, and Characterization of Novel Iron Chelators: Structure—Activity Relationships of the 2-Benzoylpyridine Thiosemicarbazone Series and Their 3-Nitrobenzoyl Analogues as Potent Antitumor Agents", Journal of Medicinal Chemistry 50(15), 3716-3729 (2007).

Khalaji, et al., "Synthesis and Characterization of Zinc(II) Complexes with 3,4-Dimethoxybenzaldehyde Thiosemicarbazone: The Crystal Structure of [Zn(34-MBTSC) 2 Cl 2 ]", Phosphorus, Sulfur, and Silicon 188, 1119-1126 (2013).

Kovala-Demertzi, et al., "Zinc(II) complexes derived from pyridine-2-carbaldehyde thiosemicarbazone and (1E)-1-pyridin-2-ylethan-1-one thiosemicarbazone. Synthesis, crystal structures and antiproliferative activity of zinc(II) complexes", Journal of Inorganic Biochemistry 100, 1558-1567 (2006).

Mohan, et al., "Synthesis, Characterization, and Antitumor Properties of some Metal Complexes of 2,6- Diacetylpyridine Bis(N4-azacyclic Thiosemicarbazone)", Journal of Inorganic Biochemistry 34, 41-54 (1988).

Moorthy, et al., "QSAR analysis of 2-benzoxazolyl hydrazone derivatives for anticancer activity and its possible target prediction", Med Chem Res 21, 133-144 (2012).

Mrozek-Wilczkiewicz, et al., "Iron Chelators in Photodynamic Therapy Revisited: Synergistic Effect by Novel Highly Active Thiosemicarbazones", ACS Medicinal Chemistry Letters 5(4), 336-339 (2014).

Patent Cooperation Treaty, International Searching Authority, Search Report and Written Opinion for PCT/US2016/015195, 16 pages, dated Mar. 30, 2016.

Priyadharsini, et al., "Docking, synthesis, characterization and evaluation of novel cdk2 inhibitors: benzothiazole derivatives", International Journal of Pharmacy and Pharmaceutical Sciences 4(3), 574-585 (2012).

Ren, et al., "A new approach to suppress nonlinearity-transparency trade-off through coordination chemistry: syntheses and spectroscopic study on second-order nonlinear optical properties of a series of square-pyramidal zinc(II) complexes", Spectrochimica Acta Part A 59, 1095-1101 (2003).

Richardson, et al., "Dipyridyl Thiosemicarbazone Chelators with Potent and Selective Antitumor Activity Form Iron Complexes with Redox Activity", J Med Chem 49, 6510-6521 (2006).

Ruangpornvisuti, et al., "A DFT investigation of conformational geometries and interconversion equilibria of phenylthiosemicarbazone and its complexation with zinc", J Mol Model 10, 418-426 (2004).

Sleebs, et al., "Discovery of Potent and Selective Benzothiazole Hydrazone Inhibitors of Bcl-XL", J Med Chem 56, 5514-5540 (2013).

Tian, et al., "Structural characterization and second-order nonlinear optical properties of zinc halide thiosemicarbazone complexes", Polyhedron 21, 1217-1222 (2002).

Todorovic, et al., "Synthesis and characterization of Zn(II) and Cd(II) complexes with 2,6-diacetylpyridine-bis (selenosemicarbazone). Crystal structure of a Ni(II) complex with a modified 2,6-diacetylpyridine-bis (selenosemicarbazone)", Inorganic Chemistry Communications 9, 862-865 (2006).

Webster, et al., "Synthesis and characterization of novel pentagonal bipyramidal compleses of iron(II), cobalt(II), and zinc(II)", Journal of American Chemical Society 95(19), 6505-6506 (1973).

Yu, et al., "Allele-Specific p53 Mutant Reactivation", Cancer Cell 21, 614-625 (2012).

Yu, et al., "Small molecule restoration of wildtype structure and function of mutant p53 using a novel zinc-metallochaperone based mechanism", Oncotarget 5(19), 8879-8892 (2014).

Heit, et al., "Substituted Hydrazones as Tridentate Chelating Agents", Analytica Chimica Acta 32, 448-455 (1965).

Bermejo, E , et al., "Complexes of Grup 12 Metals with 2-Acetylpyridine 4N-Dimethyl-thiosemiearbazone and with 2-Acetyipyridine-N-

(56) References Cited

OTHER PUBLICATIONS oxide 4N-Dimethyl-thiosemicarbazone: Synthesis, Structure and Antifungal Activity", Zeitschrift fuer Naturforschung, B: Chemical Sciences 54(6), 777-787 (1999).

Bjelogrlic, S., et al., "Synthesis, structure and characterization of novel Cd(II) and Zn(II) complexes with the condensation product of 2-formylpyridine and selenosemicarbazide Antiproliferative activity of the synthesized complexes and related selenosemicarbazone complexes", Journal of Inorganic Biochemistry 104, 673-682 (2010).

Chhabra, N, et al., "A review of drug isomerism and its significance", Int J Appl Basic Med Res 3(1), 16-18 (2013).

Khaled, S, et al., "Synthesis and Spectroscopic Characterization of Some NOvel Polypyridine and Phenanthroline Complexes of Mn(II), Fe(II), Co(II) and Zn(II) Incorporating a Bidentate Benzothiazolyl Hydrazone Ligand", Chem Sci Trans 2(4), 1222-1231 (2013).

Kodela, R, et al., "Positional Isomers of Aspirin are Equally Potent in Inhibiting Colon Cancer Cell Growth: Differences in Mode of Cyclooxygenase Inhibition", J Pharmacol Exp Ther 346, 85-94 (2013).

Odashima, T, et al., "Determination of Microamounts of Iron by Extraction-Spectrophotometry with 2-Acetylpyridine-2-benzothiazolylhydrazone and Its Sensitization by Employing an Analog Derivative Technique", Microchemical Journal 33, 138-146 (1986).

Patani, George A., et al., "Bioisosterism: A Rational Approach in Drug Design", Chem Rev 96, 3147-3176 (1996).

Singh, K, et al., "Stereochemistry and Its Role in Drug Design", IJPSR 5(11), 4644-4659 (2014).

\* cited by examiner

HYDRAZONE DERIVATIVES FOR THE TREATMENT OF CANCER

CROSS-REFERENCE TO RELATED APPLICATIONS

This patent application claims the benefit of priority of U.S. application Ser. No. 62/108,415, filed Jan. 27, 2015, and of U.S. application Ser. No. 62/258,256, filed Nov. 20, 2015, which applications are herein incorporated by reference.

BACKGROUND

TP53 is the most commonly mutated gene in human cancer for which no effective targeted anti-cancer drug exists. The majority of TP53 mutations (>70%) are missense mutations that generate a defective protein that is generally found at high levels in cancer cells due to loss of MDM2 negative feedback. Restoring the function of p53 in mouse models of cancer is highly therapeutic. Reactivating mutant p53 using small molecules has been highly sought after, yet remains an elusive goal in the development of cancer therapeutics.

SUMMARY

The invention provides novel compounds, compositions, and methods for treating cancer. More specifically, one aspect of the present invention provides a compound of formula (I):

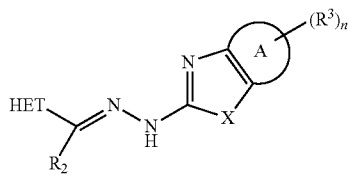

or a salt thereof, wherein:
 the ring A is a fused benzo or heteroaryl ring;
 X is S, O, —CH=CH—, or N—$R^a$;
 HET is selected from the group consisting of:

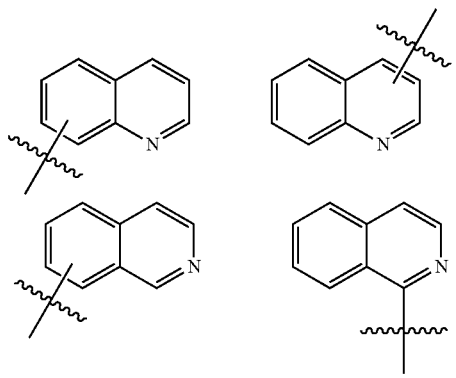

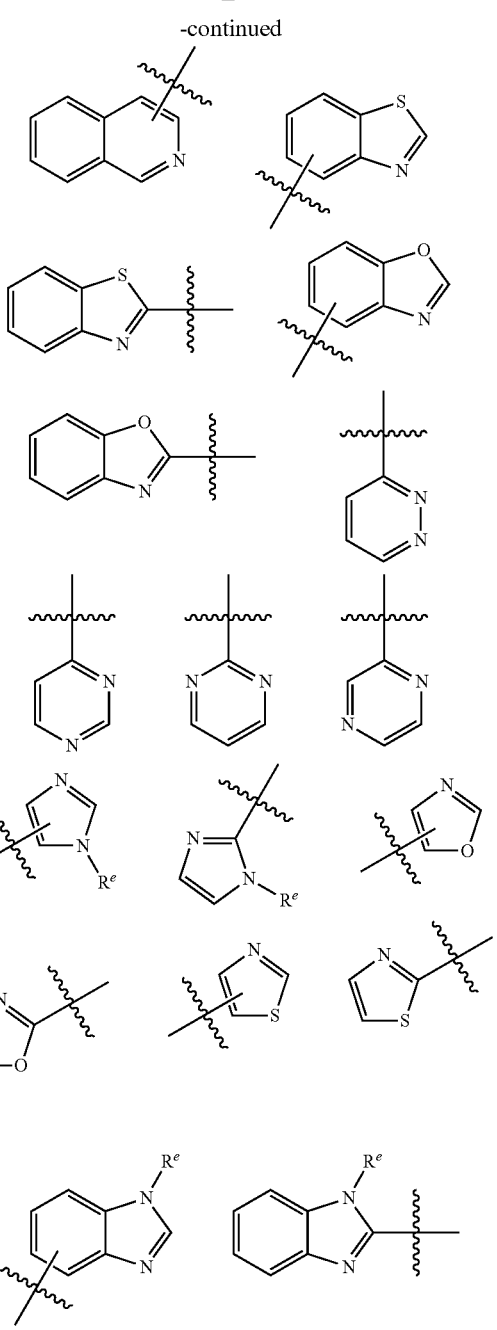

wherein HET is optionally substituted with one or more groups $R^1$ independently selected from halo, cyano, hydroxy, nitro, —N($R^a$)$_2$, carboxy, phenyl, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkoxy, ($C_1$-$C_6$)alkanoyl, ($C_1$-$C_6$)alkoxycarbonyl, ($C_2$-$C_6$)alkanoyloxy,

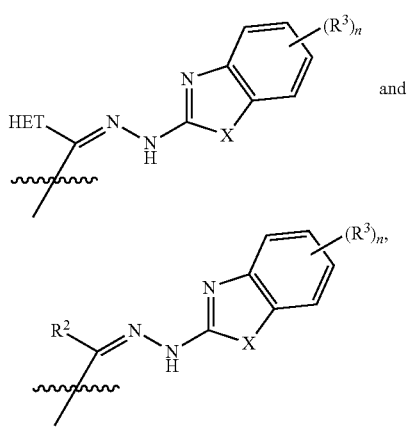

wherein any phenyl, $(C_1-C_6)$alkyl, $(C_1-C_6)$alkoxy, $(C_2-C_6)$alkenyl, $(C_2-C_6)$alkynyl, and $(C_3-C_6)$cycloalkyl, is optionally substituted with one or more groups independently selected from halo, azido, cyano, hydroxy, nitro, —N(R$^b$)$_2$, carboxy, $(C_3-C_6)$cycloalkyl, $(C_1-C_6)$alkanoyl, $(C_1-C_6)$alkoxycarbonyl, $(C_2-C_6)$alkanoyloxy, and $(C_1-C_6)$alkoxy that is optionally substituted with carboxy;

each R$^2$ is independently selected from the group consisting of H, phenyl, $(C_1-C_6)$alkyl, $(C_2-C_6)$alkenyl, $(C_2-C_6)$alkynyl, and $(C_3-C_6)$cycloalkyl, wherein any phenyl, $(C_1-C_6)$alkyl, $(C_2-C_6)$alkenyl, $(C_2-C_6)$alkynyl, and $(C_3-C_6)$ cycloalkyl, is optionally substituted with one or more groups independently selected from halo, —N(R$^c$)$_2$, $(C_3-C_6)$cycloalkyl, $(C_1-C_6)$alkoxy, and $(C_2-C_6)$alkanoyloxy;

n is 0, 1, 2, 3, or 4;

each R$^3$ is independently selected from halo, cyano, hydroxy, nitro, —N(R$^d$)$_2$, carboxy, phenyl, $(C_1-C_6)$alkyl, $(C_2-C_6)$alkenyl, $(C_2-C_6)$alkynyl, $(C_3-C_6)$cycloalkyl, $(C_1-C_6)$alkoxy, $(C_1-C_6)$alkanoyl, $(C_1-C_6)$alkoxycarbonyl, and $(C_2-C_6)$alkanoyloxy, wherein any phenyl, $(C_1-C_6)$alkyl, $(C_2-C_6)$alkenyl, $(C_2-C_6)$alkynyl, $(C_1-C_6)$alkoxy, and $(C_3-C_6)$ cycloalkyl, is optionally substituted with one or more groups independently selected from halo, cyano, hydroxy, nitro, —N(R$^c$)$_2$, carboxy, $(C_3-C_6)$cycloalkyl, $(C_1-C_6)$alkoxy, $(C_1-C_6)$alkanoyl, $(C_1-C_6)$alkoxycarbonyl, and $(C_2-C_6)$alkanoyloxy;

R$^a$ is selected from the group consisting of H, $(C_1-C_6)$ alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, wherein any $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, is optionally substituted with one or more groups independently selected from halo, $(C_3-C_6)$cycloalkyl, —N(R$^g$)$_2$, morpholino, and $(C_1-C_6)$alkoxy; or two R$^a$ taken together with the nitrogen to which they are attached form a azetidino, pyrrolidino, piperidino, or morpholino ring;

each R$^b$ is independently selected from the group consisting of H, $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, wherein any $(C_1-C_6)$alkyl, $(C_2-C_6)$alkenyl, $(C_2-C_6)$ alkynyl, $(C_3-C_6)$cycloalkyl, $(C_1-C_6)$alkanoyl, and $(C_1-C_6)$ alkoxycarbonyl, is optionally substituted with one or more groups independently selected from halo, $(C_3-C_6)$cycloalkyl, heteroaryl, and $(C_1-C_6)$alkoxy; or two R$^b$ taken together with the nitrogen to which they are attached form an azetidino, pyrrolidino, piperidino, or morpholino ring; and each R$^c$ is independently selected from the group consisting of H, $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, wherein any $(C_1-C_6)$alkyl, $(C_2-C_6)$alkenyl, $(C_2-C_6)$ alkynyl, $(C_3-C_6)$cycloalkyl, $(C_1-C_6)$alkanoyl, and $(C_1-C_6)$ alkoxycarbonyl, is optionally substituted with one or more groups independently selected from halo, $(C_3-C_6)$cycloalkyl, and $(C_1-C_6)$alkoxy; or two R$^c$ taken together with the nitrogen to which they are attached form a azetidino, pyrrolidino, piperidino, or morpholino ring;

each R$^d$ is independently selected from the group consisting of H, $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, wherein any $(C_1-C_6)$alkyl, $(C_2-C_6)$alkenyl, $(C_2-C_6)$ alkynyl, $(C_3-C_6)$cycloalkyl, $(C_1-C_6)$alkanoyl, and $(C_1-C_6)$ alkoxycarbonyl, is optionally substituted with one or more groups independently selected from halo, $(C_3-C_6)$cycloalkyl, and $(C_1-C_6)$alkoxy; or two R$^d$ taken together with the nitrogen to which they are attached form a azetidino, pyrrolidino, piperidino, or morpholino ring;

R$^e$ is independently selected from the group consisting of H and $(C_1-C_6)$alkyl that is optionally substituted with one or more groups independently selected from halo, $(C_3-C_6)$ cycloalkyl, —N(R$^f$)$_2$, and $(C_1-C_6)$alkoxy;

each R$^f$ is independently selected from the group consisting of H, $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, wherein any $(C_1-C_6)$alkyl, $(C_2-C_6)$alkenyl, $(C_2-C_6)$ alkynyl, $(C_3-C_6)$cycloalkyl, $(C_1-C_6)$alkanoyl, and $(C_1-C_6)$ alkoxycarbonyl, is optionally substituted with one or more groups independently selected from halo, $(C_3-C_6)$cycloalkyl, and $(C_1-C_6)$alkoxy; or two R$^f$ taken together with the nitrogen to which they are attached form a azetidino, pyrrolidino, piperidino, or morpholino ring; and each R$^g$ is independently selected from the group consisting of H, $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, wherein any $(C_1-C_6)$alkyl, $(C_2-C_6)$alkenyl, $(C_2-C_6)$ alkynyl, $(C_3-C_6)$cycloalkyl, $(C_1-C_6)$alkanoyl, and $(C_1-C_6)$ alkoxycarbonyl, is optionally substituted with one or more groups independently selected from halo, $(C_3-C_6)$cycloalkyl, and $(C_1-C_6)$alkoxy; or two R$^g$ taken together with the nitrogen to which they are attached form a azetidino, pyrrolidino, piperidino, or morpholino ring;

wherein if HET is not substituted with one or more (e.g. 1, 2, 3, or 4) groups R$^1$, then R$^2$ is not H, methyl, ethyl, propyl, isopropyl, butyl, tert-butyl, cyclopropyl, cyclohexyl, phenyl, benzyl or 2-pyridyl.

Another aspect of the present invention provides a pharmaceutical composition, comprising, a compound of formula I or a pharmaceutically acceptable salt thereof, and a pharmaceutically acceptable carrier.

Another aspect of the present invention provides a method of inhibiting cancer cell growth, comprising contacting the cancer cell with an effective amount of a compound of formula I or a salt thereof.

Another aspect of the present invention provides a method of treating cancer in an animal (e.g. a human), comprising administering to the animal a compound of formula I or a pharmaceutically acceptable salt thereof.

The invention further includes methods of preparing, methods of separating, and methods of purifying the compounds described herein.

Additional advantages and novel features of this invention shall be set forth in part in the description that follows, and in part will become apparent to those skilled in the art upon examination of the following specification, or may be learned by the practice of the invention. The advantages of the invention may be realized and attained by means of the instrumentalities, combinations, compositions, and methods particularly pointed out in the appended claims.

DETAILED DESCRIPTION

Figure 1:
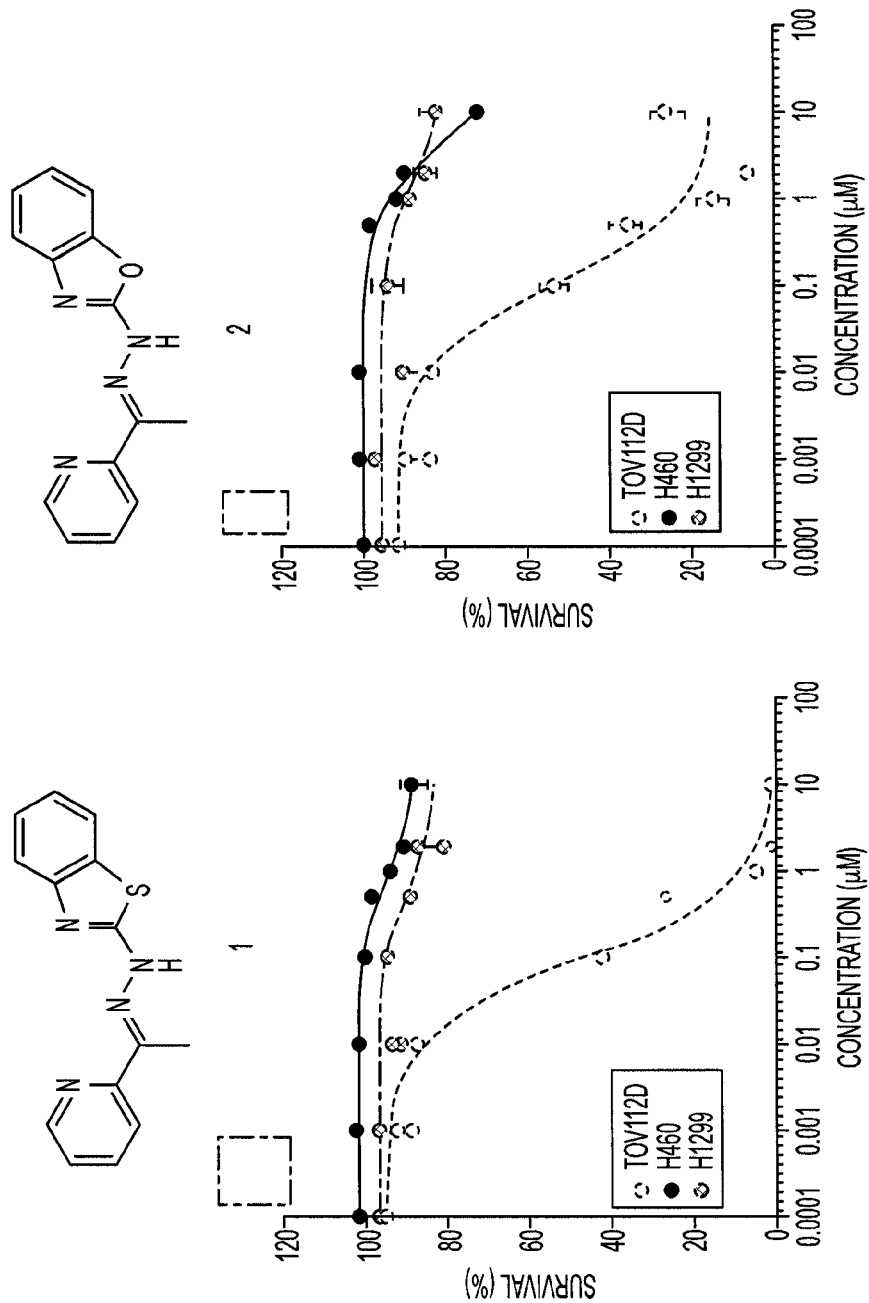
FIG. 1 illustrates the three day cell growth inhibition assays comparing compounds 1 and 2 tested against three human tumor cell lines, TOV112D (p53-R175H), H460 (p53-WT), and H1299 (p53-null).
Figure 2:
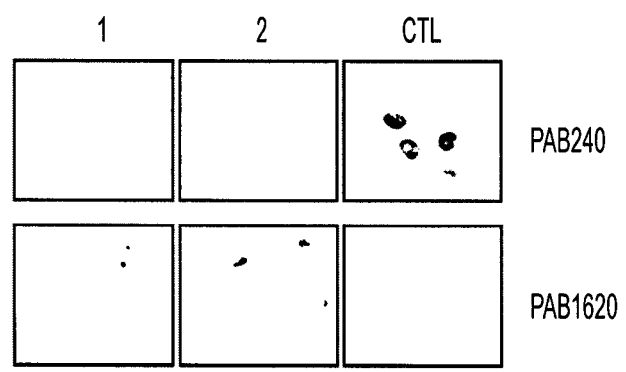
FIG. 2 shows PAB1620 antibody recognition of wildtype conformation after treatment of mutant p53 with compounds 1 and 2.

The following definitions are used, unless otherwise described: halo is fluoro, chloro, bromo, or iodo. Alkyl, alkoxy, alkenyl, alkynyl, etc. denote both straight and branched groups; but reference to an individual radical such as propyl embraces only the straight chain radical, a branched chain isomer such as isopropyl being specifically referred to.

The term allyl as used herein refers to a substituent, molecular fragment, or radical having the chemical formula —$CH_2$—CH═$CH_2$.

The term "benzyl" as used herein refers to a substituent, molecular fragment, or radical having the chemical formula —$CH_2CH_5$.

The term "butyl" as used herein refers to a four-carbon alkyl radical, substituent, or molecular fragment having the chemical formula —$C_4H_9$.

The term "cyclopropyl" as used herein refers to a radical, substituent, or molecular fragment having a chemical structure derived from cyclopropane and having the chemical formula $C_3H_5$.

The term "ethyl" as used herein refers to an alkyl substituent, radical, or molecular fragment having the chemical formula —$C_2H_5$.

The term "isopropyl" as used herein refers to a propyl with a group attached to the secondary carbon.

The term "methyl" as used herein refers to an alkyl derived from methane and containing one carbon atom bonded to three hydrogen atoms and having the chemical formula —$CH_3$.

The term "propyl" as used herein refers to a linear three-carbon alkyl substituent, molecular fragment, or radical having the chemical formula —$C_3H_7$.

The term "phenyl" refers to a cyclic group of atoms, radical, substituent, or molecular fragment having the chemical formula —$C_6H_5$.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

Specific values listed below for radicals, substituents, and ranges, are for illustration only; they do not exclude other defined values or other values within defined ranges for the radicals and substituents.

Specifically, ($C_1$-$C_6$)alkyl can be methyl, ethyl, propyl, isopropyl, butyl, iso-butyl, sec-butyl, pentyl, 3-pentyl, or hexyl; ($C_3$-$C_6$)cycloalkyl can be cyclopropyl, cyclobutyl, cyclopentyl, or cyclohexyl; ($C_1$-$C_6$)alkoxy can be methoxy, ethoxy, propoxy, isopropoxy, butoxy, iso-butoxy, sec-butoxy, pentoxy, 3-pentoxy, or hexyloxy; ($C_2$-$C_6$)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; ($C_2$-$C_6$)alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$-$C_6$)alkanoyl can be acetyl, propanoyl or butanoyl; ($C_1$-$C_6$)alkoxycarbonyl can be methoxycarbonyl, ethoxycarbonyl, propoxycarbonyl, isopropoxycarbonyl, butoxycarbonyl, pentoxycarbonyl, or hexyloxycarbonyl; and ($C_2$-$C_6$)alkanoyloxy can be acetoxy, propanoyloxy, butanoyloxy, isobutanoyloxy, pentanoyloxy, or hexanoyloxy.

In one embodiment of the invention, when HET is optionally substituted 2-pyridinyl, 2-pyrazinyl, 2-pyrimidinyl, 4-pyrimidinyl, 2-pyridazinyl, 2-quinolinyl, 2-isoquinolinyl, 3-isoquinolinyl, then $R^1$ is not $CH_3$, $OCH_3$, OH, Cl, Br, F, $CF_3$, $NO_2$, $NH_2$, $NHCOCH_3$, $N(CH_3)_2$, Phenyl, CN, C═NH($NH_2$), C═NH(NHOH), COOH, or COO-alkyl.

In one embodiment the compound of formula (I) is a compound of formula (Ia):

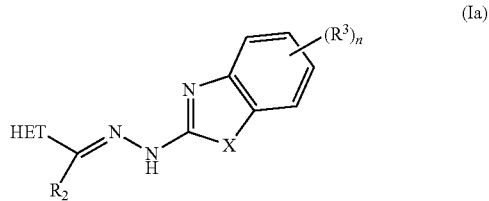

or a salt thereof, wherein:

X is S, O, N—H, or N—$R^a$;

HET is selected from the group consisting of:

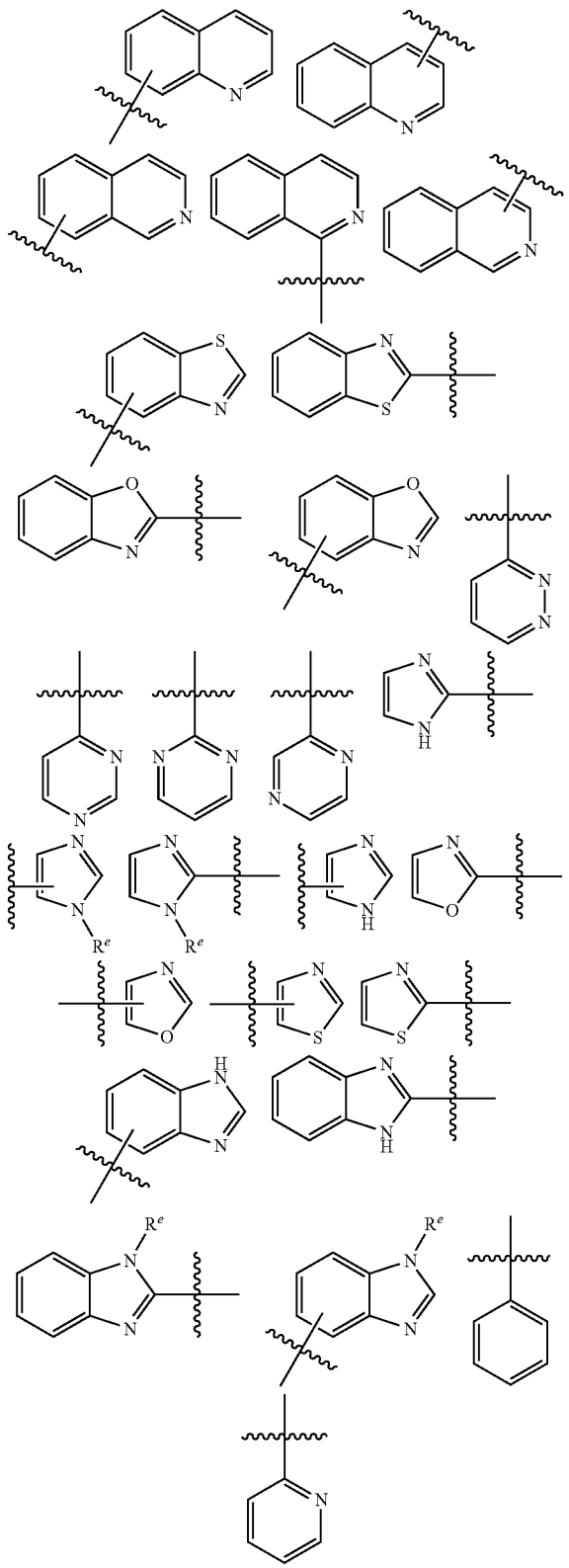

wherein HET is optionally substituted with one or more (e.g. 1, 2, 3, or 4) groups $R^1$ independently selected from halo, cyano, hydroxy, nitro, —N($R^a$)$_2$, carboxy, phenyl, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkoxy, ($C_1$-$C_6$)alkanoyl, ($C_1$-$C_6$)alkoxycarbonyl, ($C_2$-$C_6$)alkanoyloxy, and

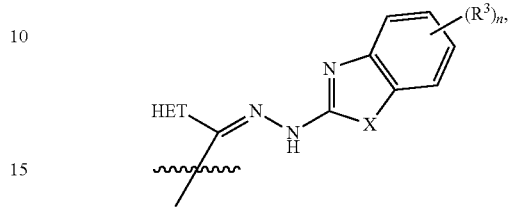

wherein any phenyl, ($C_1$-$C_6$)alkyl, ($C_1$-$C_6$)alkoxy, ($C_2$-$C_6$)alkenyl, ($C_2$-$C_6$)alkynyl, and ($C_3$-$C_6$)cycloalkyl, is optionally substituted with one or more groups independently selected from halo, cyano, hydroxy, nitro, —N($R^b$)$_2$, carboxy, ($C_3$-$C_6$)cycloalkyl, ($C_1$-$C_6$)alkoxy, ($C_1$-$C_6$)alkanoyl, ($C_1$-$C_6$)alkoxycarbonyl, and ($C_2$-$C_6$)alkanoyloxy;

$R^2$ is selected from the group consisting of H, phenyl, ($C_1$-$C_6$)alkyl, ($C_2$-$C_6$)alkenyl, ($C_2$-$C_6$)alkynyl, and ($C_3$-$C_6$)cycloalkyl, wherein any phenyl, ($C_1$-$C_6$)alkyl, ($C_2$-$C_6$)alkenyl, ($C_2$-$C_6$)alkynyl, and ($C_3$-$C_6$)cycloalkyl, is optionally substituted with one or more groups independently selected from halo, —N($R^c$)$_2$, ($C_3$-$C_6$)cycloalkyl, ($C_1$-$C_6$)alkoxy, and ($C_2$-$C_6$)alkanoyloxy;

n is 1, 2, 3, or 4;

each $R^3$ is independently selected from halo, cyano, hydroxy, nitro, —N($R^d$)$_2$, carboxy, phenyl, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkoxy, ($C_1$-$C_6$)alkanoyl, ($C_1$-$C_6$)alkoxycarbonyl, and ($C_2$-$C_6$)alkanoyloxy, wherein any phenyl, ($C_1$-$C_6$)alkyl, ($C_2$-$C_6$)alkenyl, ($C_2$-$C_6$)alkynyl, ($C_1$-$C_6$)alkoxy, and ($C_3$-$C_6$)cycloalkyl, is optionally substituted with one or more groups independently selected from halo, cyano, hydroxy, nitro, —N($R^c$)$_2$, carboxy, ($C_3$-$C_6$)cycloalkyl, ($C_1$-$C_6$)alkoxy, ($C_1$-$C_6$)alkanoyl, ($C_1$-$C_6$)alkoxycarbonyl, and ($C_2$-$C_6$)alkanoyloxy;

$R^a$ is selected from the group consisting of H, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, wherein any ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, is optionally substituted with one or more groups independently selected from halo, ($C_3$-$C_6$)cycloalkyl, and ($C_1$-$C_6$)alkoxy; or two $R^a$ taken together with the nitrogen to which they are attached form a azetidino, pyrrolidino, piperidino, or morpholino ring;

each $R^b$ is independently selected from the group consisting of H, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, wherein any ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, is optionally substituted with one or more groups independently selected from halo, ($C_3$-$C_6$)cycloalkyl, heteroaryl, and ($C_1$-$C_6$)alkoxy; or two $R^b$ taken together with the nitrogen to which they are attached form an azetidino, pyrrolidino, piperidino, or morpholino ring; and each $R^c$ is independently selected from the group consisting of H, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, wherein any (C₁-C₆)alkyl, (C₂-C₆)alkenyl, (C₂-C₆)alkynyl, (C₃-C₆)cycloalkyl, (C₁-C₆)alkanoyl, and (C₁-C₆)alkoxycarbonyl, is optionally substituted with one or more groups independently selected from halo, (C₃-C₆)cycloalkyl, and (C₁-C₆)alkoxy; or two $R^c$ taken together with the nitrogen to which they are attached form a azetidino, pyrrolidino, piperidino, or morpholino ring;

each $R^d$ is independently selected from the group consisting of H, (C₁-C₆)alkyl, (C₂-C₆)alkenyl, (C₂-C₆)alkynyl, (C₃-C₆)cycloalkyl, (C₁-C₆)alkanoyl, and (C₁-C₆)alkoxycarbonyl, wherein any (C₁-C₆)alkyl, (C₂-C₆)alkenyl, (C₂-C₆)alkynyl, (C₃-C₆)cycloalkyl, (C₁-C₆)alkanoyl, and (C₁-C₆)alkoxycarbonyl, is optionally substituted with one or more groups independently selected from halo, (C₃-C₆)cycloalkyl, and (C₁-C₆)alkoxy; or two $R^d$ taken together with the nitrogen to which they are attached form a azetidino, pyrrolidino, piperidino, or morpholino ring;

$R^e$ is independently selected from the group consisting of H and (C₁-C₆)alkyl that is optionally substituted with one or more groups independently selected from halo, (C₃-C₆)cycloalkyl, —N($R^f$)₂, and (C₁-C₆)alkoxy; and each $R^f$ is independently selected from the group consisting of H, (C₁-C₆)alkyl, (C₂-C₆)alkenyl, (C₂-C₆)alkynyl, (C₃-C₆)cycloalkyl, (C₁-C₆)alkanoyl, and (C₁-C₆)alkoxycarbonyl, wherein any (C₁-C₆)alkyl, (C₂-C₆)alkenyl, (C₂-C₆)alkynyl, (C₃-C₆)cycloalkyl, (C₁-C₆)alkanoyl, and (C₁-C₆)alkoxycarbonyl, is optionally substituted with one or more groups independently selected from halo, (C₃-C₆)cycloalkyl, and (C₁-C₆)alkoxy; or two $R^f$ taken together with the nitrogen to which they are attached form a azetidino, pyrrolidino, piperidino, or morpholino ring;

wherein if HET is not substituted with one or more (e.g. 1, 2, 3, or 4) groups $R^1$, then $R^2$ is not H, methyl, ethyl, propyl, isopropyl, butyl, tert-butyl, cyclopropyl, cyclohexyl, phenyl, benzyl or 2-pyridyl.

In one embodiment HET is selected from the group consisting of:

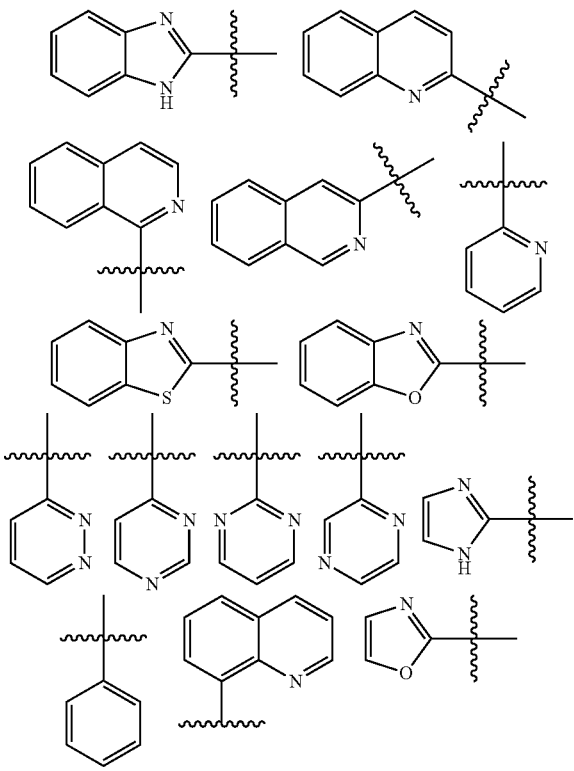

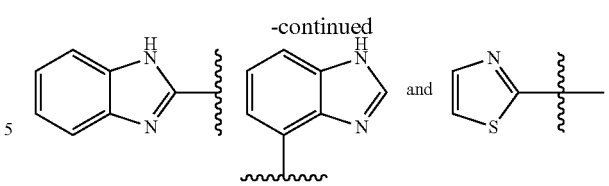

wherein HET is optionally substituted with one or more groups independently selected from halo, cyano, hydroxy, nitro, —N($R^a$)₂, carboxy, phenyl, (C₁-C₆)alkyl, (C₂-C₆)alkenyl, (C₂-C₆)alkynyl, (C₃-C₆)cycloalkyl, (C₁-C₆)alkoxy, (C₁-C₆)alkanoyl, (C₁-C₆)alkoxycarbonyl, and (C₂-C₆)alkanoyloxy, wherein any phenyl, (C₁-C₆)alkyl, (C₂-C₆)alkenyl, (C₂-C₆)alkynyl, and (C₃-C₆)cycloalkyl, is optionally substituted with one or more groups independently selected from halo, cyano, hydroxy, nitro, —N($R^a$)₂, carboxy, (C₃-C₆)cycloalkyl, (C₁-C₆)alkoxy, (C₁-C₆)alkanoyl, (C₁-C₆)alkoxycarbonyl, and (C₂-C₆)alkanoyloxy;

$R^2$ is selected from the group consisting of H, phenyl, (C₁-C₆)alkyl, (C₂-C₆)alkenyl, (C₂-C₆)alkynyl, and (C₃-C₆)cycloalkyl, wherein any phenyl, (C₁-C₆)alkyl, (C₂-C₆)alkenyl, (C₂-C₆)alkynyl, and (C₃-C₆)cycloalkyl, is optionally substituted with one or more groups independently selected from halo, —N($R^b$)₂, (C₃-C₆)cycloalkyl, (C₁-C₆)alkoxy, and (C₂-C₆)alkanoyloxy;

or $R^1$ and $R^2$ taken together with the carbon to which they are attached form a bicyclic 9- or 10-membered nitrogen ring system comprising 1, 2, 3, or 4 nitrogen atoms and at least one aromatic ring;

n is 1, 2, 3, or 4;

each $R^3$ is independently selected from halo, cyano, hydroxy, nitro, —N($R^d$)₂, carboxy, phenyl, (C₁-C₆)alkyl, (C₂-C₆)alkenyl, (C₂-C₆)alkynyl, (C₃-C₆)cycloalkyl, (C₁-C₆)alkoxy, (C₁-C₆)alkanoyl, (C₁-C₆)alkoxycarbonyl, and (C₂-C₆)alkanoyloxy, wherein any phenyl, (C₁-C₆)alkyl, (C₂-C₆)alkenyl, (C₂-C₆)alkynyl, (C₁-C₆)alkoxy, and (C₃-C₆)cycloalkyl, is optionally substituted with one or more groups independently selected from halo, cyano, hydroxy, nitro, —N($R^c$)₂, carboxy, (C₃-C₆)cycloalkyl, (C₁-C₆)alkoxy, (C₁-C₆)alkanoyl, (C₁-C₆)alkoxycarbonyl, and (C₂-C₆)alkanoyloxy;

each $R^a$ is independently selected from the group consisting of H, (C₁-C₆)alkyl, (C₂-C₆)alkenyl, (C₂-C₆)alkynyl, (C₃-C₆)cycloalkyl, (C₁-C₆)alkanoyl, and (C₁-C₆)alkoxycarbonyl, wherein any (C₁-C₆)alkyl, (C₂-C₆)alkenyl, (C₂-C₆)alkynyl, (C₃-C₆)cycloalkyl, (C₁-C₆)alkanoyl, and (C₁-C₆)alkoxycarbonyl, is optionally substituted with one or more groups independently selected from halo, (C₃-C₆)cycloalkyl, and (C₁-C₆)alkoxy; or two $R^a$ taken together with the nitrogen to which they are attached form a azetidino, pyrrolidino, piperidino, or morpholino ring; and each $R^b$ is independently selected from the group consisting of H, (C₁-C₆)alkyl, (C₂-C₆)alkenyl, (C₂-C₆)alkynyl, (C₃-C₆)cycloalkyl, (C₁-C₆)alkanoyl, and (C₁-C₆)alkoxycarbonyl, wherein any (C₁-C₆)alkyl, (C₂-C₆)alkenyl, (C₂-C₆)alkynyl, (C₃-C₆)cycloalkyl, (C₁-C₆)alkanoyl, and (C₁-C₆)alkoxycarbonyl, is optionally substituted with one or more groups independently selected from halo, (C₃-C₆)cycloalkyl, and (C₁-C₆)alkoxy; or two $R^b$ taken together with the nitrogen to which they are attached form a azetidino, pyrrolidino, piperidino, or morpholino ring.

each $R^c$ is independently selected from the group consisting of H, (C₁-C₆)alkyl, (C₂-C₆)alkenyl, (C₂-C₆)alkynyl, (C₃-C₆)cycloalkyl, (C₁-C₆)alkanoyl, and (C₁-C₆)alkoxycarbonyl, wherein any (C₁-C₆)alkyl, (C₂-C₆)alkenyl, (C₂-C₆)

alkynyl, (C₃-C₆)cycloalkyl, (C₁-C₆)alkanoyl, and (C₁-C₆)alkoxycarbonyl, is optionally substituted with one or more groups independently selected from halo, (C₃-C₆)cycloalkyl, and (C₁-C₆)alkoxy; or two R$^c$ taken together with the nitrogen to which they are attached form a azetidino, pyrrolidino, piperidino, or morpholino ring; and each R$^d$ is independently selected from the group consisting of H, (C₁-C₆)alkyl, (C₂-C₆)alkenyl, (C₂-C₆)alkynyl, (C₃-C₆)cycloalkyl, (C₁-C₆)alkanoyl, and (C₁-C₆)alkoxycarbonyl, wherein any (C₁-C₆)alkyl, (C₂-C₆)alkenyl, (C₂-C₆)alkynyl, (C₃-C₆)cycloalkyl, (C₁-C₆)alkanoyl, and (C₁-C₆)alkoxycarbonyl, is optionally substituted with one or more groups independently selected from halo, (C₃-C₆)cycloalkyl, and (C₁-C₆)alkoxy; or two R$^d$ taken together with the nitrogen to which they are attached form a azetidino, pyrrolidino, piperidino, or morpholino ring.

In one embodiment the compound of formula (I) is a compound of formula (Ia):

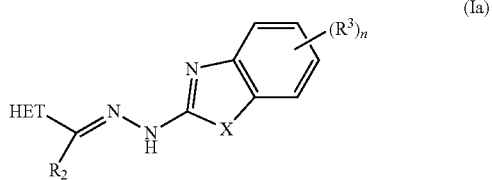

(Ia)

or a salt thereof, wherein:

X is S, O, N—H, or N-Me;

HET is selected from the group consisting of:

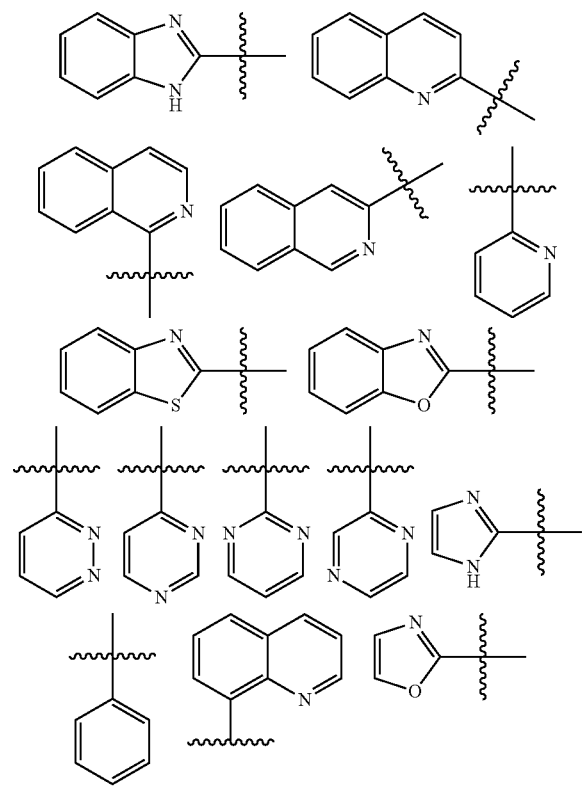

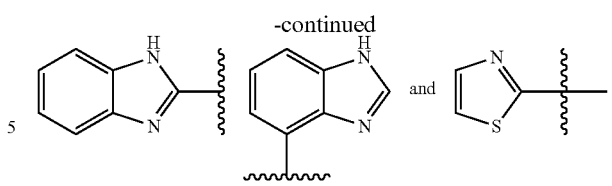

wherein HET is optionally substituted with one or more groups independently selected from halo, cyano, hydroxy, nitro, —N(R$^a$)₂, carboxy, phenyl, (C₁-C₆)alkyl, (C₂-C₆)alkenyl, (C₂-C₆)alkynyl, (C₃-C₆)cycloalkyl, (C₁-C₆)alkoxy, (C₁-C₆)alkanoyl, (C₁-C₆)alkoxycarbonyl, and (C₂-C₆)alkanoyloxy, wherein any phenyl, (C₁-C₆)alkyl, (C₂-C₆)alkenyl, (C₂-C₆)alkynyl, and (C₃-C₆)cycloalkyl, is optionally substituted with one or more groups independently selected from halo, cyano, hydroxy, nitro, —N(R$^a$)₂, carboxy, (C₃-C₆)cycloalkyl, (C₁-C₆)alkoxy, (C₁-C₆)alkanoyl, (C₁-C₆)alkoxycarbonyl, and (C₂-C₆)alkanoyloxy;

R² is selected from the group consisting of H, phenyl, (C₁-C₆)alkyl, (C₂-C₆)alkenyl, (C₂-C₆)alkynyl, and (C₁-C₆)cycloalkyl, wherein any phenyl, (C₁-C₆)alkyl, (C₂-C₆)alkenyl, (C₂-C₆)alkynyl, and (C₃-C₆)cycloalkyl, is optionally substituted with one or more groups independently selected from halo, —N(R$^b$)₂, (C₃-C₆)cycloalkyl, (C₁-C₆)alkoxy, and (C₂-C₆)alkanoyloxy;

n is 0, 1, 2, 3, or 4;

each R³ is independently selected from halo, cyano, hydroxy, nitro, —N(R$^c$)₂, carboxy, phenyl, (C₁-C₆)alkyl, (C₂-C₆)alkenyl, (C₂-C₆)alkynyl, (C₃-C₆)cycloalkyl, (C₁-C₆)alkoxy, (C₁-C₆)alkanoyl, (C₁-C₆)alkoxycarbonyl, and (C₂-C₆)alkanoyloxy, wherein any phenyl, (C₁-C₆)alkyl, (C₂-C₆)alkenyl, (C₂-C₆)alkynyl, (C₁-C₆)alkoxy, and (C₃-C₆)cycloalkyl, is optionally substituted with one or more groups independently selected from halo, cyano, hydroxy, nitro, —N(R$^c$)₂, carboxy, (C₃-C₆)cycloalkyl, (C₁-C₆)alkoxy, (C₁-C₆)alkanoyl, (C₁-C₆)alkoxycarbonyl, and (C₂-C₆)alkanoyloxy;

each R$^a$ is independently selected from the group consisting of H, (C₁-C₆)alkyl, (C₂-C₆)alkenyl, (C₂-C₆)alkynyl, (C₃-C₆)cycloalkyl, (C₁-C₆)alkanoyl, and (C₁-C₆)alkoxycarbonyl, wherein any (C₁-C₆)alkyl, (C₂-C₆)alkenyl, (C₂-C₆)alkynyl, (C₃-C₆)cycloalkyl, (C₁-C₆)alkanoyl, and (C₁-C₆)alkoxycarbonyl, is optionally substituted with one or more groups independently selected from halo, (C₃-C₆)cycloalkyl, and (C₁-C₆)alkoxy; or two R$^a$ taken together with the nitrogen to which they are attached form a azetidino, pyrrolidino, piperidino, or morpholino ring;

each R$^b$ is independently selected from the group consisting of H, (C₁-C₆)alkyl, (C₂-C₆)alkenyl, (C₂-C₆)alkynyl, (C₃-C₆)cycloalkyl, (C₁-C₆)alkanoyl, and (C₁-C₆)alkoxycarbonyl, wherein any (C₁-C₆)alkyl, (C₂-C₆)alkenyl, (C₂-C₆)alkynyl, (C₃-C₆)cycloalkyl, (C₁-C₆)alkanoyl, and (C₁-C₆)alkoxycarbonyl, is optionally substituted with one or more groups independently selected from halo, (C₃-C₆)cycloalkyl, and (C₁-C₆)alkoxy; or two R$^b$ taken together with the nitrogen to which they are attached form a azetidino, pyrrolidino, piperidino, or morpholino ring; and each R$^c$ is independently selected from the group consisting of H, (C₁-C₆)alkyl, (C₂-C₆)alkenyl, (C₂-C₆)alkynyl, (C₃-C₆)cycloalkyl, (C₁-C₆)alkanoyl, and (C₁-C₆)alkoxycarbonyl, wherein any (C₁-C₆)alkyl, (C₂-C₆)alkenyl, (C₂-C₆)alkynyl, (C₃-C₆)cycloalkyl, (C₁-C₆)alkanoyl, and (C₁-C₆)alkoxycarbonyl, is optionally substituted with one or more groups independently selected from halo, (C₃-C₆)cycloalkyl, and (C₁-C₆)alkoxy; or two R$^c$ taken together with the nitrogen to which they are attached form a azetidino, pyrrolidino, piperidino, or morpholino ring.

In one embodiment each HET is independently selected from the group consisting of:

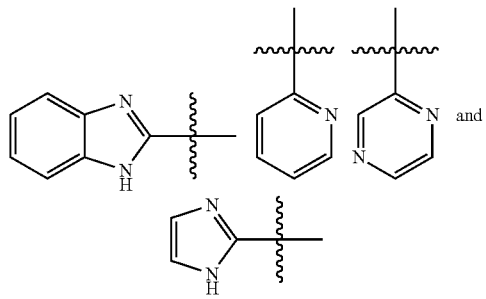

wherein HET is optionally substituted with one or more groups independently selected from halo, cyano, hydroxy, nitro, —N($R^a$)$_2$, carboxy, phenyl, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkoxy, ($C_1$-$C_6$)alkanoyl, ($C_1$-$C_6$)alkoxycarbonyl, and ($C_2$-$C_6$)alkanoyloxy, wherein any phenyl, ($C_1$-$C_6$)alkyl, ($C_2$-$C_6$)alkenyl, ($C_2$-$C_6$)alkynyl, and ($C_3$-$C_6$)cycloalkyl, is optionally substituted with one or more groups independently selected from halo, cyano, hydroxy, nitro, —N($R^a$)$_2$, carboxy, ($C_3$-$C_6$)cycloalkyl, ($C_1$-$C_6$)alkoxy, ($C_1$-$C_6$)alkanoyl, ($C_1$-$C_6$)alkoxycarbonyl, and ($C_2$-$C_6$)alkanoyloxy.

In one embodiment each HET is independently selected from the group consisting of:

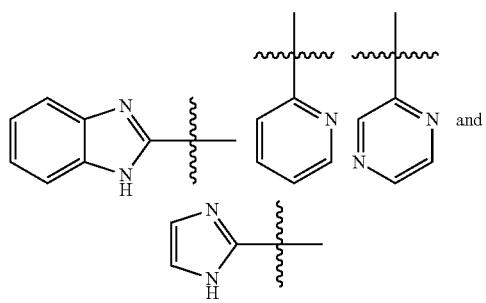

wherein HET is optionally substituted with one or more groups independently selected from ($C_1$-$C_6$)alkyl and —N($R^a$)$_2$.

In one embodiment each $R^2$ is selected from the group consisting of H, methyl, ethyl, propyl, isopropyl, butyl, tert-butyl, allyl, cyclopropyl, phenyl, benzyl, $CH_2CH_2OCH_3$, and $CH_2CH_2$—$N(CH_3)_2$.

In one embodiment each $R^2$ is selected from the group consisting of methyl, ethyl, isopropyl, and tert-butyl.

In one embodiment the compound is selected from the group consisting of:

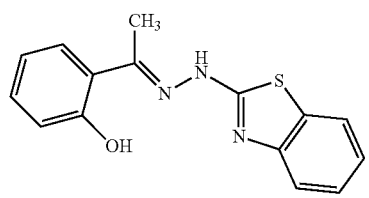

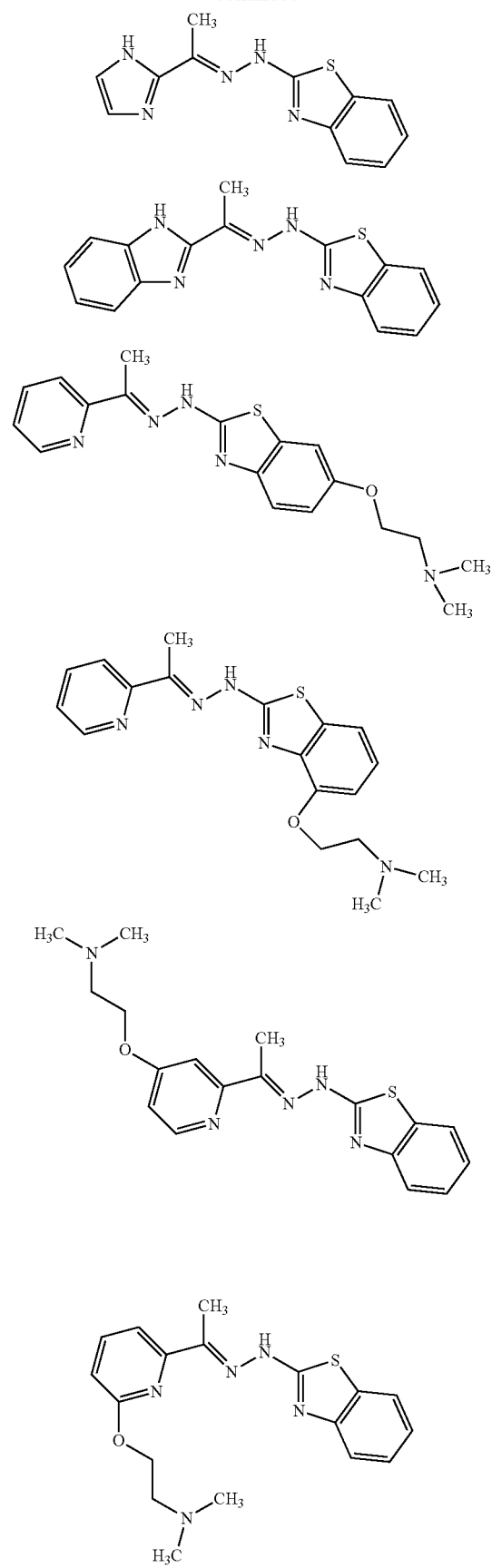

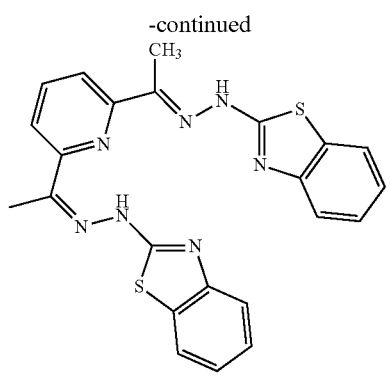
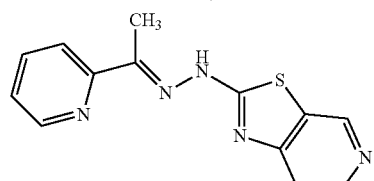
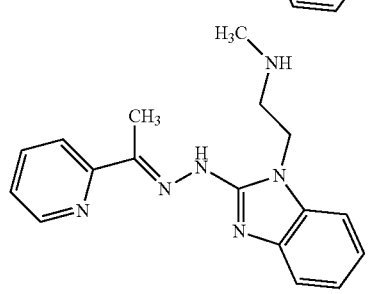
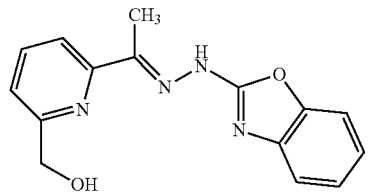
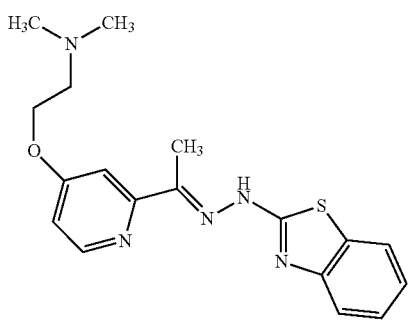
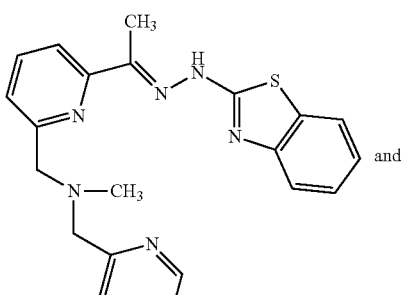
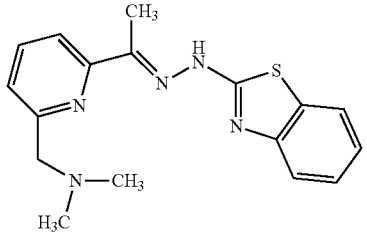
and salts thereof.
In one embodiment the compound is selected from the group consisting of:
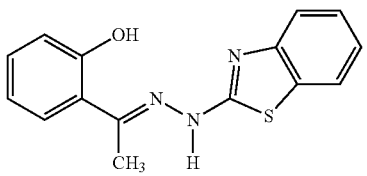
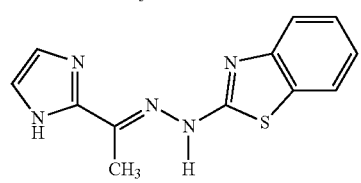
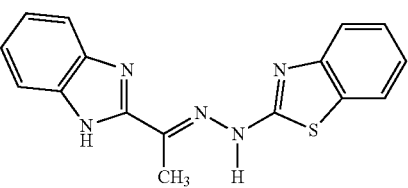
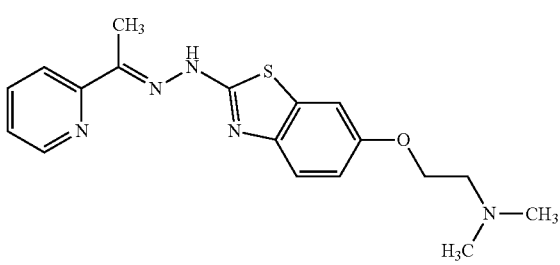

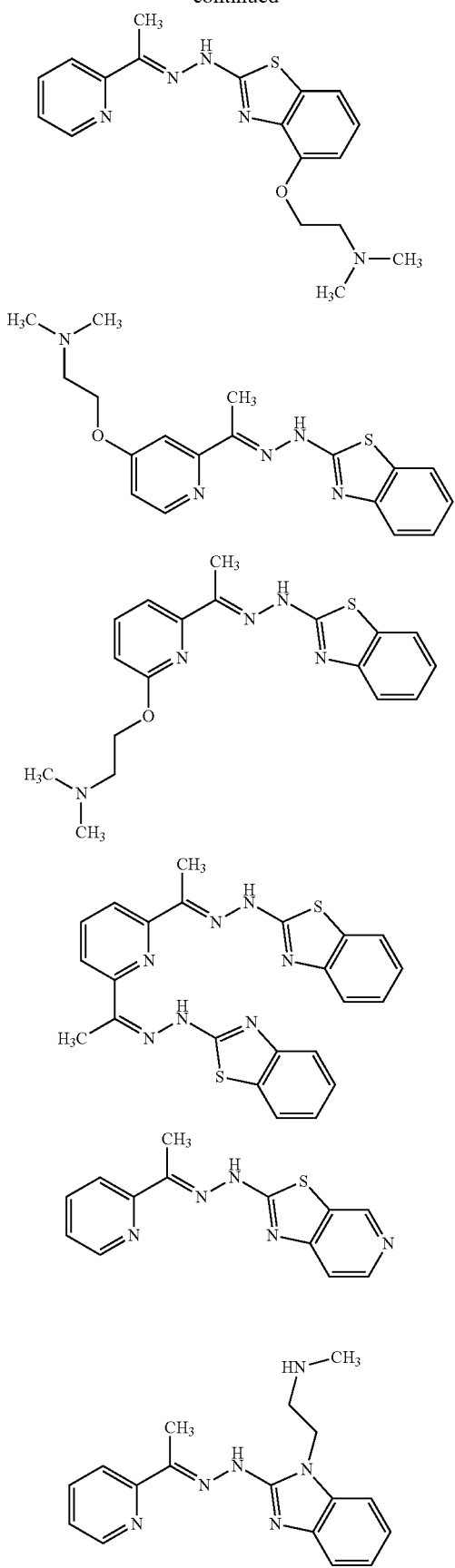
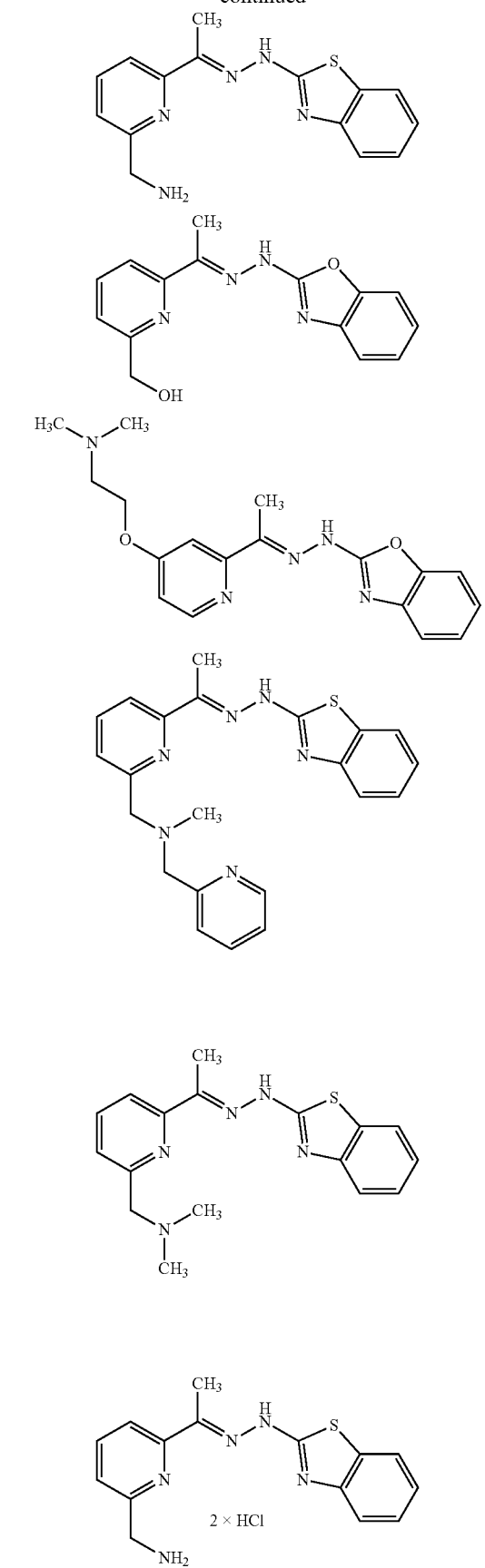

-continued
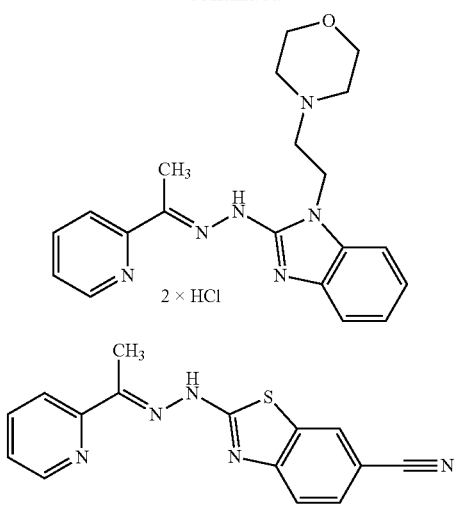
2 × HCl
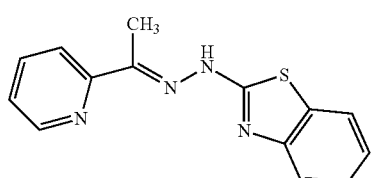
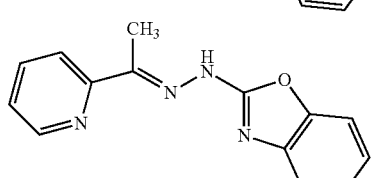
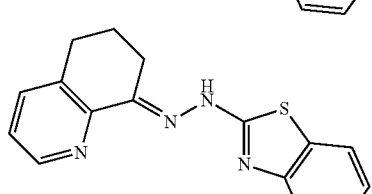
and salts thereof.
In one embodiment the invention provides a compound selected from the group consisting of:
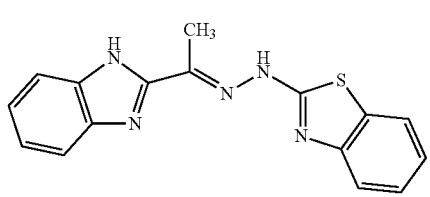
-continued
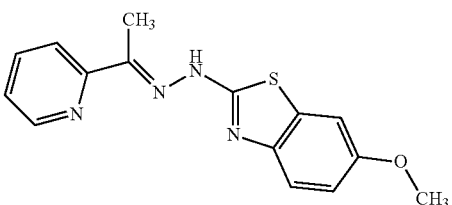
and
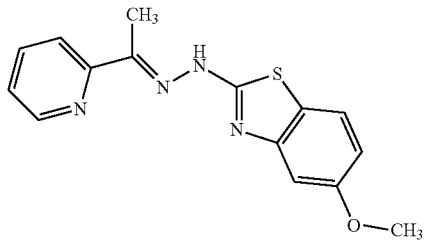
In one embodiment the compound is selected from the group consisting of:
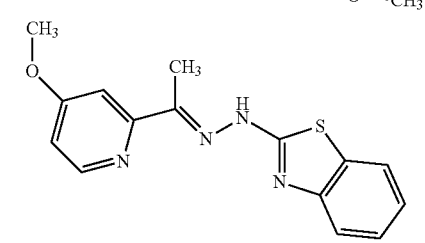
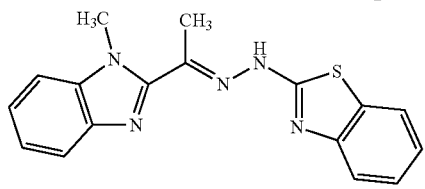
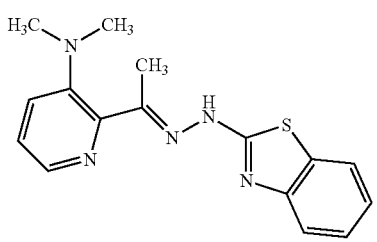

-continued
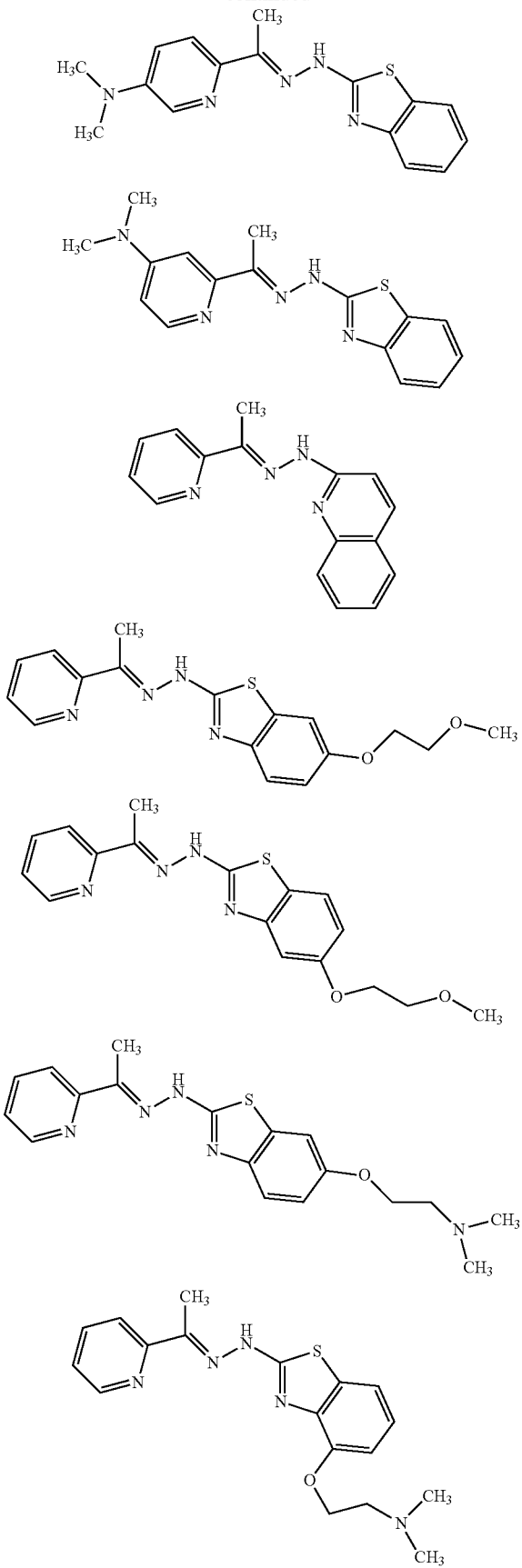
-continued
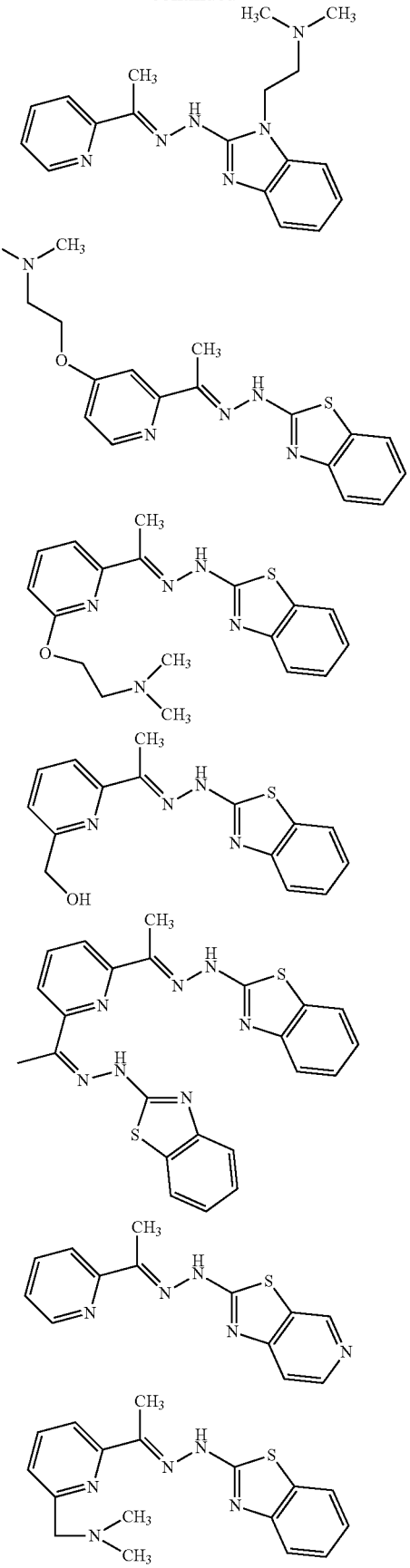

-continued
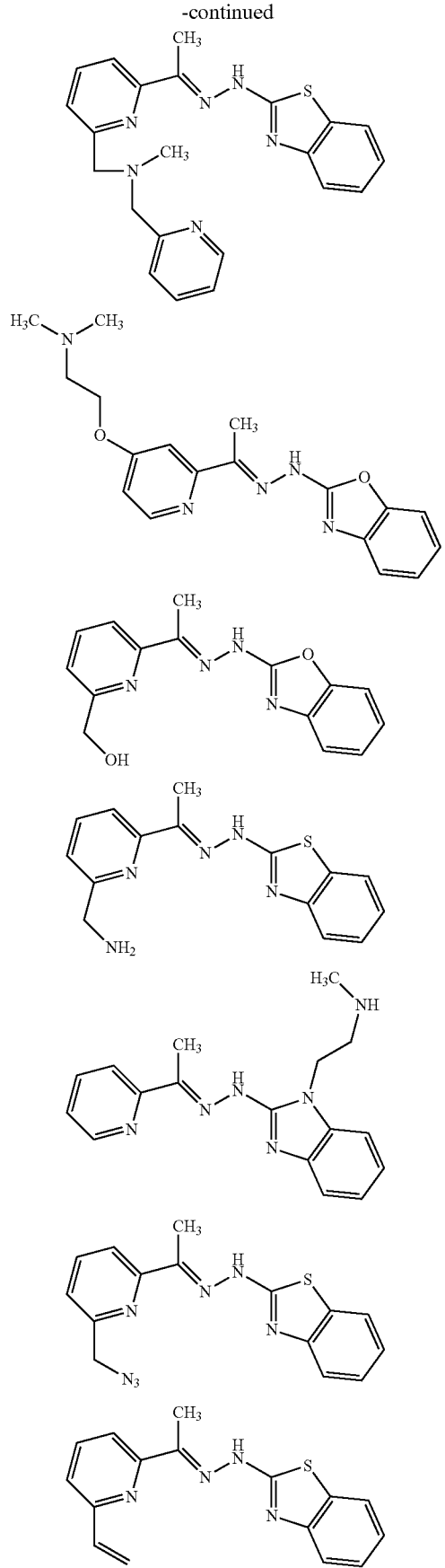
-continued
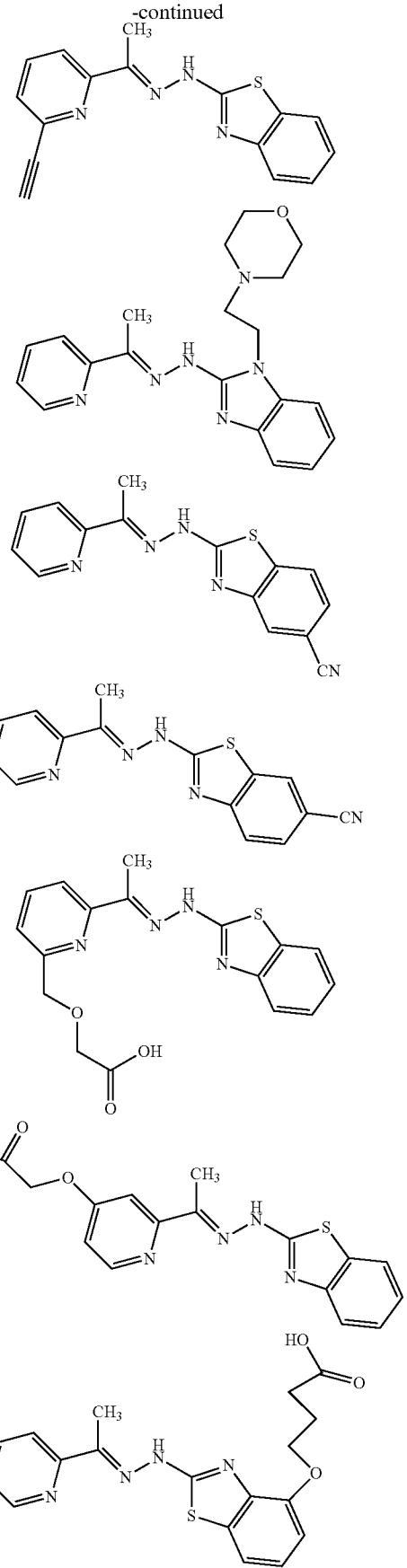

-continued

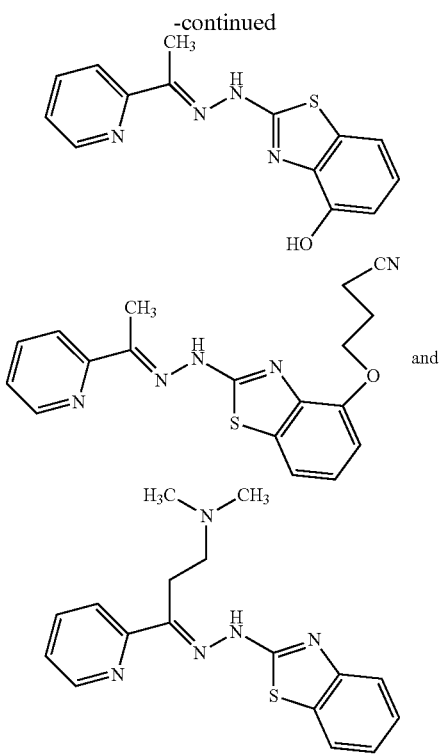

and salts thereof.

The ability of ZMC1, NTA ($Zn^{2+}$-binding homolog), and A6 (structural homolog) to increase intracellular $[Zn^{2+}]_{free}$ was evaluated by treating cells with the fluorescent $Zn^{2+}$ indicator FluoZin-3-AM (FZ3-AM) in complete media and imaging them using confocal microscopy. In both HEK293 (non-cancer, p53-WT) and TOV112D (ovarian cancer, p53-R175H) cells, ZMC1 increased intracellular $[Zn^{2+}]_{free}$ as indicated by increased fluorescence, but NTA and A6 did not. This result is consistent with the metallochaperone (MC) model for ZMC1 function and explains the inability of NTA and A6 to reactivate p53-R175H at micromolar concentrations.

Of the two control compounds, A6 shuttled $Zn^{2+}$ into the liposomes, but NTA did not.

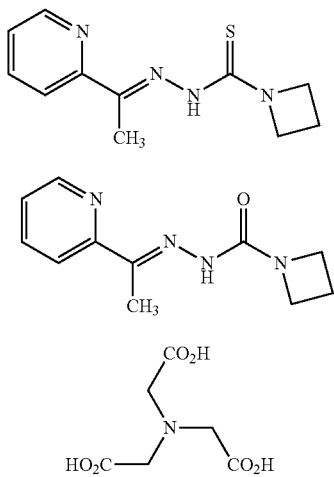

ZMC1

A6

NTA

NTA binds $Zn^{2+}$ with an affinity similar to that of ZMC1, but it cannot cross either liposomal or cellular membranes, likely because it possesses negative charges. A6, on the other hand, lacks charges and is similar in structure to ZMC1, but binds $Zn^{2+}$ weakly ($K_d$=1.1 µM). It can function as an ionophore in conditions of the liposome experiments where external $[Zn^{2+}]_{free}$ was 10 µM. However, in complete media containing 10% fetal bovine serum (FBS), $Zn^{2+}$-binding proteins from the serum (e.g. albumin) necessarily compete for $Zn^{2+}$ with any putative MC, making the effective $[Zn^{2+}]_{free}$ much lower than $[Zn^{2+}]_{total}$. A6 therefore likely does not increase intracellular $[Zn^{2+}]_{free}$ in culture because $K_{d,A6}$ is greater than extracellular $[Zn^{2+}]_{free}$. Thus, both an appropriate $Zn^{2+}$ $K_d$ and ionophore activity influence ZMC1 activity.

To determine whether ZMC1 can traverse lipid bilayers as a free compound, the $[Zn^{2+}]_{free}$ gradient was reversed by adding a large excess of metal ion chelator EDTA to the solution outside of the liposomes; fluorescence was monitored in the presence and absence of ZMC1. EDTA alone did not cause a significant decrease in RZ-3 fluorescence as the liposomal membranes are impermeable to EDTA. After subsequent addition of ZMC1, there was a time dependent decrease in RZ-3 fluorescence. This result indicates that free ZMC1 crossed the liposomal membranes, bound internal $Zn^{2+}$, and transported it back outside the liposome where the metal was then bound by the much stronger chelator EDTA. Thus, ZMC1 can cross biological membranes both as free drug and drug-$Zn^{2+}$ complex, and therefore can transport $Zn^{2+}$ into cells without becoming trapped as either species.

To ensure that the fluorescence results were due to $Zn^{2+}$ transport and not to non-specific disruption of liposomal membranes, a liposomal leakage assay was performed using the self-quenching fluorophore calcein. When calcein is encapsulated at concentrations above 4 mM its fluorescence is decreased via self-quenching. Leakage is detected by a fluorescence increase as the dye dilutes and its fluorescence dequenches. At the highest concentrations of ZMC1 and $ZnCl_2$ a significant fluorescence increase was not detected. Disruption of liposomes can also be detected by alteration of their size distribution. The size distribution of liposomes treated with the highest concentrations of $ZnCl_2$ and ZMC1 was identical to that of untreated liposomes. Together, these data indicate the liposomal membranes remained intact upon ZMC1 treatment, and therefore the RZ-3 fluorescence changes are attributable only to specific $Zn^{2+}$ transport.

Characterization of ZMC1-Mediated $Zn^{2+}$ Transport in Live Cells

To extend the investigation of ZMC1 as an ionophore to living systems, ZMC1-mediated $Zn^{2+}$ transport was quantified in cells. The kinetics of intracellular $[Zn^{2+}]_{free}$ increase was measured by loading HEK293 and TOV112D cells with FZ3-AM, treating the cells with ZMC1 and $ZnCl_2$, and monitoring fluorescence by time-lapse microscopy. To minimize the potential for $Zn^{2+}$ contamination and contributions from poorly defined elements in complete media (e.g. FBS), cells were treated and imaged in $Ca^{2+}$ and $Mg^{2+}$-free Earle's Balanced Salt Solution supplemented with 10 mM HEPES pH 7.4 (EBSS/H (−)Ca/Mg). Excess $ZnCl_2$ with the $Zn^{2+}$ ionophore pyrithione (PYR) was used as a positive control. Excess membrane-permeable $Zn^{2+}$ chelator N,N,N',N'-tetrakis(2-pyridylmethyl)ethane-1,2-diamine (TPEN) was used as a negative control. When treated with $ZnCl_2$ alone or ZMC1 alone, neither cell type showed an increase in intracellular $[Zn^{2+}]_{free}$. When treated with both ZMC1 and $ZnCl_2$, both cell lines showed a time dependent increase at two different $ZnCl_2$ concentrations, demonstrating that both ZMC1 and extracellular $Zn^{2+}$ are required. When the fluorescence increases were fit to first-order exponentials, both concentrations of ZnCl$_2$ yielded identical half-lives in their respective cell types, which we combine to report $t_{1/2}$ (HEK293)=124±20 s and $t_{1/2}$ (TOV112D)=156±50 s (mean±SD, n=4).

The steady-state intracellular [Zn$^{2+}$] of both cell types was then quantified after treatment with the 2:1 ratio of ZMC1:ZnCl$_2$. Cells were again loaded with FZ3-AM, treated with 1 μM ZMC1 and 0.5 μM ZnCl$_2$ in EBSS/H (−)Ca/Mg, and imaged as above. To normalize for differential dye loading, cells were then sequentially treated with excess PYR/ZnCl$_2$, imaged, treated with TPEN, and imaged again. PYR/ZnCl$_2$ and TPEN served to saturate and apoize the intracellular FZ3, respectively. In the absence of drug an intracellular [Zn$^{2+}$]$_{free}$ of 0.69±0.25 nM was measured for HEK293 cells and 0.71±0.19 nM was measured for TOV112D cells. These values reflect the lower limit of detection by FZ3-AM and are likely overestimates. Upon treatment with ZMC1 and ZnCl$_2$ intracellular [Zn$^{2+}$]$_{free}$ rose to 18.1±4.7 nM for HEK293 cells and 15.8±2.5 nM for TOV112D cells. These concentrations are theoretically sufficient to reactivate ~90% of p53-R175H based on the $K_{d1}$ value of 2.1 nM measured for DBD-R175H.

Materials and Methods

Reagents

FZ3-AM, RZ-3 (K$^+$ salt), and cell culture media were purchased from Life Technologies. DOPC was purchased from Avanti Polar Lipids. ZMC1 and A6 were similarly obtained. Zn$^{2+}$ (ZMC1)$_2$ was synthesized and crystallized. HEK293 and TOV112D cells were purchased from ATCC and maintained in DMEM+GlutaMAX with 10% FBS and 1 mg/mL penicillin-streptomycin under a 5% CO$_2$ atmosphere at 37° C. All non-cell based experiments were conducted in 50 mM Tris pH 7.2, 0.1 M NaCl at 25° C.

Liposome Import Assay

DOPC-liposomes were prepared by film rehydration and extrusion followed by gel filtration and diluted to an OD$_{600}$=0.06 in buffer. The size distribution of the liposomes was determined by dynamic light scattering (DLS) using a Malvern Zetasizer Nano ZS. Fluorescence measurements were taken on a Horiba Fluoromax-4 spectrofluorimeter in a 5×5 mm quartz cuvette with $\lambda_{ex}/\lambda_{em}$=550/572 nm for RZ-3 and 490/515 nm for calcein. Initial Zn$^{2+}$ import/export was quantified by fitting the first 10-30 s of data after each treatment to a line and converted to units of flux using the following Eqn 1:

$$J_i = \frac{\Delta F}{\Delta t} \cdot \left(\frac{F_{max} - F_{min}}{[RZ3]}\right) \cdot \left(\frac{SA}{Vol}\right) \quad \text{Eqn 1}$$

where $J_i$ is the initial flux, $\Delta F/\Delta t$ is the slope of the fit line, $F_{max}$ is RZ-3 fluorescence in the presence of saturating Zn$^{2+}$ and 1% TritonX-100, $F_{min}$ is RZ-3 fluorescence in the presence of excess EDTA and 1% TritonX-100, [RZ3] is the concentration of encapsulated RZ-3, and SA/Vol is the surface area to volume ratio calculated assuming hollow spheres of the mean diameter determined by DLS.

Intracellular [Zn$^{2+}$]$_{free}$ Imaging

TOV112D or HEK293 cells (40,000 cells/well) were plated on either 8-well BD Falcon chambered culture slides (Corning Life Sciences) or 8-chambered #1.5 Nunc Lab-Tek II chambered coverglasses (Thermo Scientific) treated with poly-L-lysine. After 48 h, cells were washed 2×5 m in serum-free media and incubated with 1 μM FZ3-AM for 40 m at 37° C. Cells were then washed 2×5 m in either EBSS/H (−)Ca/Mg or phenol-red free DMEM+10% FBS containing the indicated treatments for 20 m before imaging. For nuclear colocalization, 1 μg/mL Hoechst 33342 was also included. Cells were imaged using a Zeiss LSM510 META NLO confocal microscope equipped with 37° C. environmental control chamber. FZ3 and Hoechst 33342 were excited at 488 nm (argon laser) and 790 nm (Chameleon Ti:sapphire laser), respectively. To determine the kinetics of fluorescence change, each background-subtracted image in the time-lapse series was integrated in ImageJ and normalized to the integrated fluorescence of the first frame after treatment. For quantification of intracellular [Zn$^{2+}$]$_{free}$, each cell was analyzed in the treated, 50 μM PYR/ZnCl$_2$ (1:1), and 100 μM TPEN images by taking the mean fluorescence of an ROI inside the cell subtracted by an ROI immediately outside the cell measured in ImageJ. The [Zn$^{2+}$]$_{free}$ for each cell was then calculated by Eqn 2:

$$[Zn^{2+}]_{free} = \frac{F - F_{min}}{F_{max} - F} \cdot K_d \quad \text{Eqn 2}$$

Where F, $F_{max}$, and $F_{min}$ are fluorescence in the treatment, PYR/ZnCl$_2$, and TPEN images, respectively, and $K_d$ is that of FZ3 for Zn$^{2+}$ (15 nM) (31). To minimize the effects of outliers the lowest and highest 5% of cells in each series were rejected, and the remaining values averaged to give the value from that experiment. The number of cells analyzed in each trial ranged from 54-163. For nuclear colocalization, treated, PYR/ZnCl$_2$, and TPEN treated images costained with Hoechst 33342 were aligned and each pixel subjected to Eqn. 2 in MATLAB (MathWorks). The resultant images were Gaussian mean filtered and false-colored by calculated [Zn$^{2+}$]$_{free}$.

p53-R175H Immunofluorescence

DMEM+10% FBS was treated with 5 g Chelex 100 resin per 100 mL media for 1 hour with gentle shaking. The media was then decanted and filtered through 0.2 μm sterile filter. TOV112D cells were then incubated with 1 μM ZMC1 in untreated media, Chelex-treated media, or media+10 μM TPEN at 37° C. for 2 h, fixed, and stained with PAB240 and PAB1640.

Assays:

Cell growth inhibition assay using human tumor cell lines with different p53 status (wildtype, null, p53-R175H) were employed to determine if wildtype structure is restored to mutant p53 after treatment with a zinc metallochaperone. Compounds 1 and 2 shown in FIG. 1 selectively killed the p53-R175H tumor cell line (TOV112D) while leaving the p53 wildtype (H460) and p53 null (H1299) cell lines undisturbed.

An immunofluorescence assay using conformation specific antibodies was used to determine if a test compound could induce a wildtype conformation of mutant p53.

The invention will now be illustrated by the following non-limiting Examples.

EXAMPLES

Chemistry: General Method for the Synthesis of Monomers

A general synthetic approach to the preparation of molecules with structural features that contribute to optimal zinc binding Kd, potency, and efficacy in the TOV112D cell line is shown in Scheme 1. The chemistry shown in Scheme 1 may also be used to make the corresponding benzoxazole or N-methylbenzimidazole-substituted target as well. (Easmon, J., Heinisch G., Hofman, J., Langer, T., Gunicke, H H., Fink, J., Pürstinger G. (1997) Thiazolyl and benzothiazolyl hyrdrazones derived from α-(N)-acetylpyridines and diazines: synthesis, antiproliferative activity and CoMFA studies. *European Journal of Medicinal Chemistry* 32, 397-408; Easmon, J., Purstinger, G., Thies, K. S., Heinisch, G., and Hofmann, J. (2006) Synthesis, structure-activity relationships, and antitumor studies of 2-benzoxazolyl hydrazones derived from alpha-(N)-acyl heteroaromatics. *Journal of Medicinal Chemistry* 49, 6343-6350; Purstinger, G., Heinisch, G., Easmon, J., Hofmann, J., Heinz-Herbert, F. (2002) Heterocyclic Hydrazones for Use as Anti-cancer agents. (Office, C. I. P. ed.)

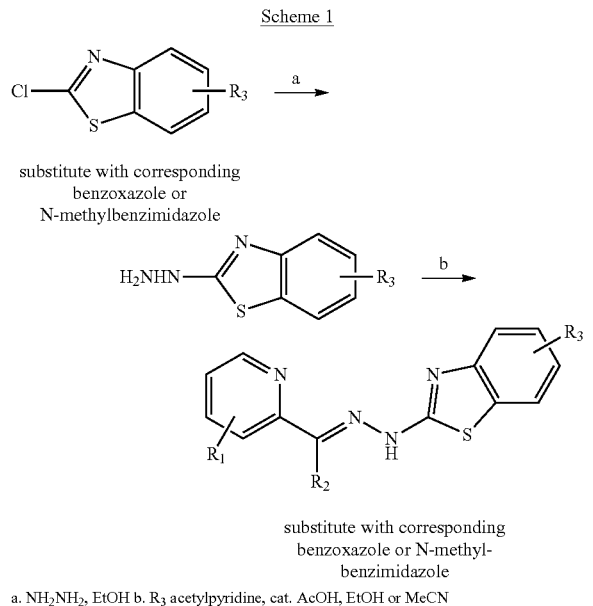

substitute with corresponding benzoxazole or N-methylbenzimidazole substitute with corresponding benzoxazole or N-methylbenzimidazole a. NH$_2$NH$_2$, EtOH b. R$_3$ acetylpyridine, cat. AcOH, EtOH or MeCN Example 1 (Method A) (E)-2-(2-(1-(pyridin-2-yl) ethylidene)hydrazinyl)benzo[d]thiazole

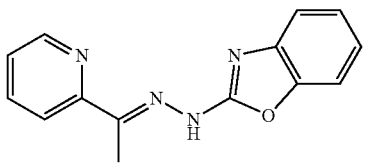 [SMILES: C/C(=N\Nc1nc2ccccc2o1)c1ccccn1]

2-Acetylpyridine (2.00 g, 16.5 mmol, 1 equiv.) was dissolved in DCM (50 mL) and stirred at ambient temperature. 2-Hydrazinylbenzo[d]thiazole (2.73 g, 16.5 mmol, 1 equiv.) was added in a single portion. Acetic acid (catalytic, 4 drops) and MeOH (3 mL) were added and the reaction mixture stirred at ambient temperature overnight. The reaction was concentrated to dryness and the resulting residue was recrystallized from MeOH to give (E)-2-(2-(1-(pyridin-2-yl)ethylidene)hydrazinyl)benzo[d]thiazole (0.520 g, 1.94 mmol, 12% yield) as a white solid. $^1$H-NMR (400 MHz, CDCl$_3$) δ 2.44 (s, 3H), 7.19 (dt, J=7.2 Hz, 1.01 Hz, 1H), 7.26 (m, 1H), 7.36 (dt, J=7.2 Hz, 1.01 Hz, 1H), 7.62 (d, J=7.96 Hz, 1H), 7.71 (d, J=7.08 Hz, 1H), 7.74 (dt, J=7.76 Hz, 1.76 Hz, 1H), 8.18 (d, J=8.12 Hz, 1H), 8.60 (br. d, J=4.32 Hz, 1H), 9.14 (br. s, 1H, NH). MS: 269.0 [M+H]$^+$.

Example 2

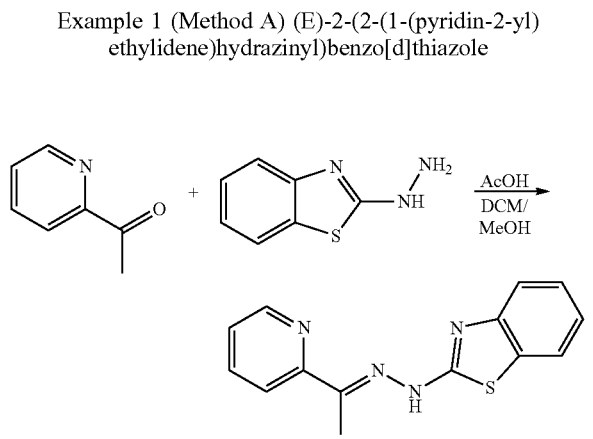

(E)-2-(2-(1-(pyridin-2-yl)ethylidene)hydrazinyl) benzo[d]oxazole (2)

Following Method A for the condensation of 2-hydrazinylbenzo[d]oxazole and 1-(pyridin-2-yl)ethan-1-one the title compound 2 was isolated as a white solid after recrystallization from MeOH. $^1$H-NMR (400 MHz, CDCl$_3$) δ 2.48 (s, 3H), 7.16 (br. t, J=7.28 Hz, 1H), 7.28 (m, 2H), 7.44 (br. d, J=7.28 Hz, 1H), 7.51 (br. d, J=7.04 Hz), 7.73 (t, J=7.40 Hz, 1H), 8.27 (br. d, J=7.28 Hz, 1H), 8.60, (d, J=4.72 Hz, 1H), 8.85 (br. s, 1H, NH). MS: 253.1 [M+H]$^+$.

Example 3

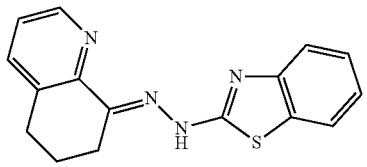 [SMILES: c1cnc2c(c1)CCC/C2=N\Nc1nc2ccccc2s1]

(E)-2-(2-(6,7-dihydroquinolin-8(5H)-ylidene)hydrazinyl)benzo[d]thiazole (3)

Following Method A for the condensation of 2-hydrazinylbenzo[d]thiazole and 6,7-dihydroquinolin-8(5H)-one the title compound 3 was isolated as a white solid after recrystallization from MeOH. $^1$H-NMR (400 MHz, CDCl$_3$) δ 1.98 (m, 2H), 2.72 (br. t, J=6.48 Hz, 2H), 2.81 (br. t, J=5.88 Hz, 2H), 7.18 (m, 2H), 7.34 (t, J=7.40 Hz, 1H), 7.47 (d, J=7.44 Hz, 1H), 7.59 (d, J=7.92 Hz, 1H), 7.70 (d, J=7.72 Hz, 1H), 8.65 (d, J=3.92 Hz, 1H), 9.37 (br. s, 1H, NH). MS: 295.0 [M+H]$^+$.

Example 4

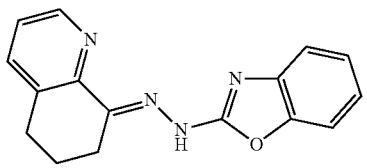 [SMILES: c1cnc2c(c1)CCC/C2=N\Nc1nc2ccccc2o1]

(E)-2-(2-(6,7-dihydroquinolin-8(5H)-ylidene)hydrazinyl)benzo[d]oxazole (4)

Following Method A for the condensation of 2-hydrazinylbenzo[d]oxazole and 6,7-dihydroquinolin-8(5H)-one the title compound 4 was isolated as a white solid after recrystallization from MeOH. $^{1}$H-NMR (400 MHz, CDCl$_3$) δ 2.02 (m, 2H), 2.88 (t, J=6.00 Hz, 2H), 3.00 (br. t, J=5.64 Hz, 2H), 7.09 (m, 1H), 7.19 (m, 2H), 7.31 (m, 2H), 7.61 (d, J=7.60 Hz, 1H), 8.81 (br. s, 1H). MS: 279.1 [M+H]$^{+}$.

Example 5

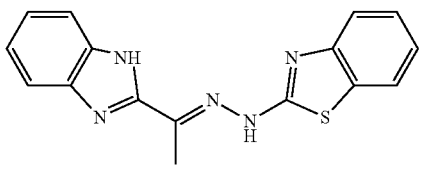 [SMILES: C/C(=N\Nc1nc2ccccc2s1)c1nc2ccccc2[nH]1]

(E)-2-((1-(1H-benzo[d]imidazol-2-yl)ethyl)diazenyl)benzo[d]thiazole (5)

Following Method A for the condensation of 2-hydrazinylbenzo[d]thiazole and 1-(1H-benzo[d]imidazol-2-yl)ethan-1-one the title compound 5 was isolated as a white solid after recrystallization from MeOH. $^{1}$H-NMR (400 MHz, MeOD) δ 2.51 (s, 3H), 7.15 (t, J=7.60 Hz, 1H), 7.28 (m, 2H), 7.33 (t, J=7.28 Hz, 1H), 7.47 (s, 1H), 7.65 (m, 3H). MS: 308.1 [M+H]$^{+}$.

Example 6

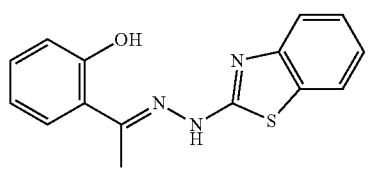 [SMILES: C/C(=N\Nc1nc2ccccc2s1)c1ccccc1O]

(E)-2-(1-(benzo[d]thiazol-2-yldiazenyl)ethyl)phenol (6)

Following Method A for the condensation of 2-hydrazinylbenzo[d]thiazole and 1-(2-hydroxyphenyl)ethan-1-one the title compound 6 was isolated as a white solid after recrystallization from MeOH. $^{1}$H-NMR (400 MHz, CDCl$_3$) δ 2.49 (s, 3H), 6.91 (dt, J=8.04 Hz, 1.16 Hz, 1H), 7.04 (dd, J=8.20 Hz, 1.0 Hz, 1H), 7.13 (dt, J=7.72 Hz, 1.16 Hz, 1H), 7.25 (m, 1H), 7.30 (m, 2H), 7.52 (m, 2H), 12.42 (s, 1H, NH). MS: 284.0 [M+H]$^{+}$.

Example 7

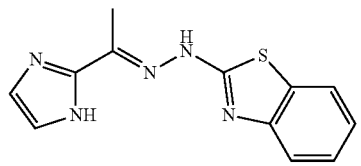 [SMILES: C/C(=N\Nc1nc2ccccc2s1)c1ncc[nH]1]

(E)-2-(2-(1-(1H-imidazol-2-yl)ethylidene)hydrazinyl)benzo[d]thiazole 1(7)

Following Method A for the condensation of 2-hydrazinylbenzo[d]thiazole and 1-(1H-imidazol-2-yl)ethan-1-one the title compound 7 was isolated as a white solid after recrystallization from MeOH. $^{1}$H-NMR (400 MHz, CDCl$_3$) δ 2.42 (s, 3H), 7.17 (m, 3H), 7.34 (t, J=7.36 Hz, 1H), 7.53 (d, I=7.92 Hz, 1H), 7.66 (d, J=7.84 Hz, 1H), 9.89 (br. s, 1H, NH). MS: 258.2 [M+H]$^{+}$.

Methods B-Q

Method B.

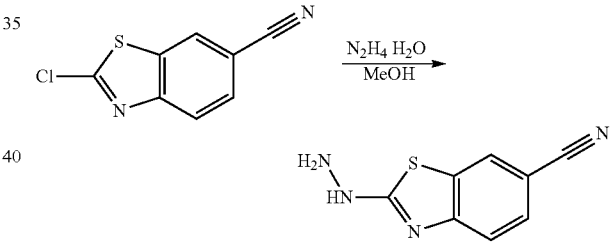

2-Hydrazinylbenzo[d]thiazole-6-carbonitrile

To a solution of 2-chlorobenzo[d]thiazole-6-carbonitrile (100 mg, 0.51 mmol, 1 eq) in MeOH (1 ml) was added hydrazine hydrate (1 ml). The reaction was stirred for 1 hour, and the white precipitate was filtered and washed with MeOH to give 2-hydrazinylbenzo[d]thiazole-6-carbonitrile as a white solid (88 mg, 90% yield).

Method C.

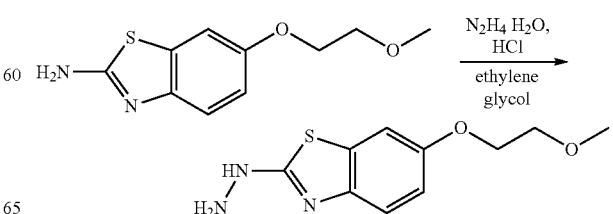

2-Hydrazinyl-6-(2-methoxyethoxy)benzo[d]thiazole 6-(2-methoxyethoxy)benzo[d]thiazol-2-amine (120 mg, 0.54 mmol, 1 eq) was added to a solution of hydrazine hydrate (156 ul, 1.87 mmol, 3.5 eq) and conc. HCl (156 ul, 3.21 mmol, 6 eq) in ethylene glycol (3 ml) and heated overnight at 130° C. The reaction was partitioned in DCM/water, extracted 3×DCM, dried over sodium sulfate and concentrated under reduced pressure. The residue was purified by column chromatography to give 2-hydrazinyl-6-(2-methoxyethoxy)benzo[d]thiazole (78 mg, 61% yield) as a brown solid.

Method D.

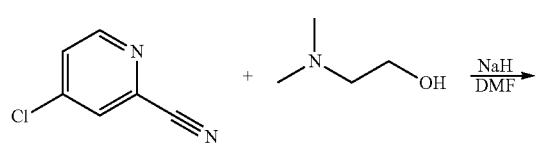

4-(2-(dimethylamino)ethoxy)picolinonitrile

A solution of NaH (60% in mineral oil, 0.867 g, 21.65 mmol, 1.2 equiv.) in DMF (75 mL) was cooled to 0° C. 2-Dimethylaminoethanol (1.61 g, 18 mmol, 1 equiv) was added dropwise and the solution was allowed to warm to ambient temperature. The mixture was allowed to stir at ambient temperature for 45 minutes. The reaction was cooled to 0° C. and 4-chloro-2-pyridinecarbonitrile (2.50 g, 18 mmol, 1 equiv.) was added in one portion and the reaction stirred overnight. The reaction was poured into brine and the resulting solution was diluted with water. The mixture was extracted with EtOAc (3×), the combined extracts were washed with water (2×) and brine (1×), dried over Na$_2$SO$_4$ and concentrated. The resulting oil was purified by column chromatography (2% TEA/5% MeOH/DCM) to give 4-(2-(dimethylamino)ethoxy)picolinonitrile as a pale yellow oil (2.85 g, 14.9 mmol, 83%).

Method E.

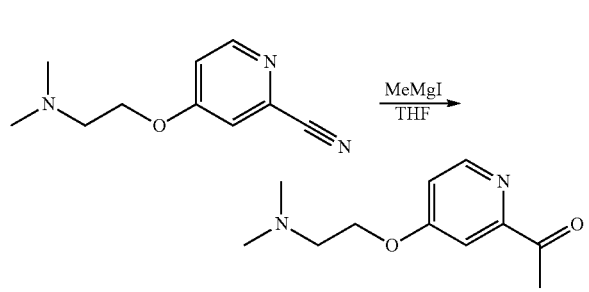

1-(4-(2-(dimethylamino)ethoxy)pyridin-2-yl)ethan-1-one 4-(2-(dimethylamino)ethoxy)picolinonitrile (2.85 g, 14.9 mmol, 1 equiv.) was dissolved in dry THF (30 mL). A solution of MeMgI (3M in ether, 7.45 mL, 22.4 mmol, 1.5 equiv) was added dropwise and the mixture continued to stir at 0° C. for 8 hours. The reaction was quenched with water (50 mL) and acidified to pH 1-2 with 1M aqueous HCl. The mixture was extracted with EtOAc and the organic layer was discarded. The mixture was basified to pH 9-11 with 1M aqueous NaOH and extracted with of EtOAc (5×). The combined extracts were dried over Na$_2$SO$_4$ and concentrated to give 1-(4-(2-(dimethylamino)ethoxy)pyridin-2-yl)ethan-1-one (2.68 g, 12.9 mmol, 86%) as a yellow oil, which was used crude without further purification.

Method F.

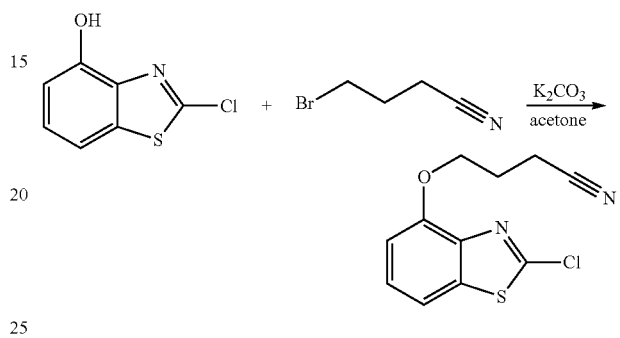

4-((2-chlorobenzo[d]thiazol-4-yl)oxy)butanenitrile 2-chlorobenzo[d]thiazol-4-ol (0.305 g, 1.64 mmol, 1 equiv.) was dissolved in acetone (5.5 mL) and the mixture stirred at ambient temperature. 4-Bromobutyronitrile (0.267 g, 1.81 mmol, 1.1 equiv.) and K$_2$CO$_3$ (1.14 g, 8.22 mmol, 5 equiv.) were added and the resulting solution was heated to 60° C. for 3 hours. The reaction was cooled to ambient temperature and filtered through a thin pad of celite. The filtrate was concentrated and the resulting residue was dissolved in chloroform and filtered. The filtrate was concentrated and the resulting solid was triturated with hexanes to give 4-((2-chlorobenzo[d]thiazol-4-yl)oxy)butanenitrile (0.227 g, 0.898 mmol, 55%) as a pale off-white solid which was used without further purification.

Method G.

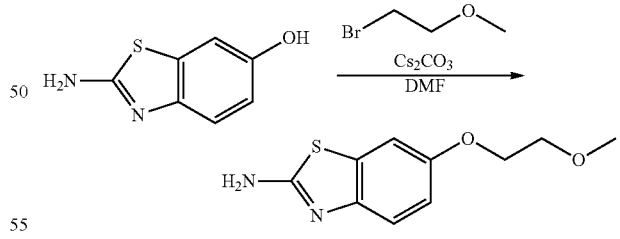

To a solution of 2-aminobenzo[d]thiazol-6-ol (500 mg, 3.0 mmol, 1 eq) in DMF (30 ml) was added cesium carbonate (4.9 g, 15.0 mmol, 5 eq), and 1-bromo-2-methoxyethane (310 ul, 3.3 mmol, 1.1 eq). The reaction was stirred overnight at room temperature and subsequently taken up in EtOAc. The EtOAc layer was washed 2×water, 1×brine, dried over sodium sulfate and concentrated. The residue was purified by column chromatography and recrystallized from EtOAc to give 6-(2-methoxyethoxy)benzo[d]thiazol-2-amine (251 mg, 37% yield) as a white solid.

Method H.

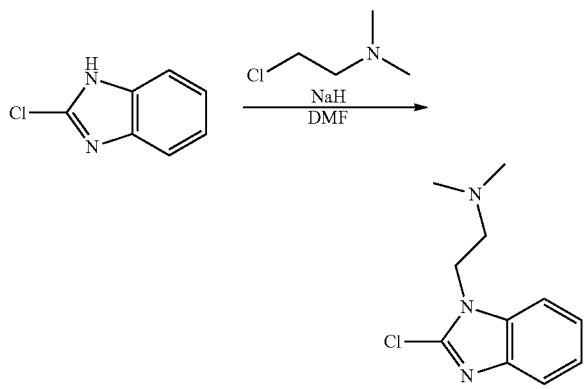

2-(2-chloro-1H-benzo[d]imidazol-1-yl)-N,N-dimethylethan-1-amine

To a solution of 2-chloro-1H-benzo[d]imidazole (500 mg, 3.2 mmol, 1 eq) in DMF (7 ml) at 0° C., was added sodium hydride (60% dispersion, 394 mg, 9.84 mmol, 3.0 eq). After stirring for 5 min at 0° C., 2-chloro-N,N-dimethylethan-1-amine hydrochloride (709 mg, 4.92 mmol, 1.5 eq) was added, and the reaction was stirred overnight at room temperature. The reaction was quenched with water and partitioned in a mixture of ethyl acetate and water. The organic layer was washed 2× water, 1× brine, dried over sodium sulfate and concentrated under reduced pressure. The residue was purified by silica gel chromatography and isolated 2-(2-chloro-1H-benzo[d]imidazol-1-yl)-N,N-dimethylethan-1-amine (311 mg, 1.4 mmol, 42% yield) as a white solid.

Method I.

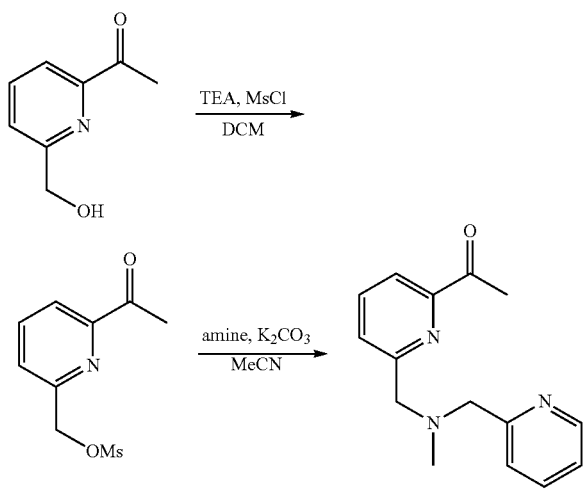

1-(6-((methyl(pyridin-2-ylmethyl)amino)methyl)pyridin-2-yl)ethan-1-one

To a solution of 1-(6-(hydroxymethyl)pyridin-2-yl)ethan-1-one (500 mg, 3.3 mmol, 1 eq) in DCM (20 ml) was added TEA (693 ul, 4.97 mmol, 1.5 eq) followed by mesyl chloride (256 ul, 3.3 mmol, 1 eq). The reaction was partitioned in DCM/water, washed 2×water, 1×brine, dried over sodium sulfate and concentrated under reduced pressure to give (6-acetylpyridin-2-yl)methyl methanesulfonate (663 mg, 87% yield) as a waxy orange solid. To a solution of (6-acetylpyridin-2-yl)methyl methanesulfonate (100 mg, 0.44 mmol, 1 eq) in MeCN (4 ml) was added N-methyl-1-(pyridin-2-yl)methanamine (54 ul, 0.44 mmol, 1 eq) and potassium carbonate (241 mg, 1.7 mmol, 4 eq). The reaction was stirred overnight at room temperature, partitioned in EtOAc/water, washed 2×water, dried over sodium sulfate and concentrated to afford 1-(6-((methyl(pyridin-2-ylmethyl)amino)methyl)pyridin-2-yl)ethan-1-one (97 mg, 87% yield) as a yellow oil that was used without further purification.

Method J (Example 30).

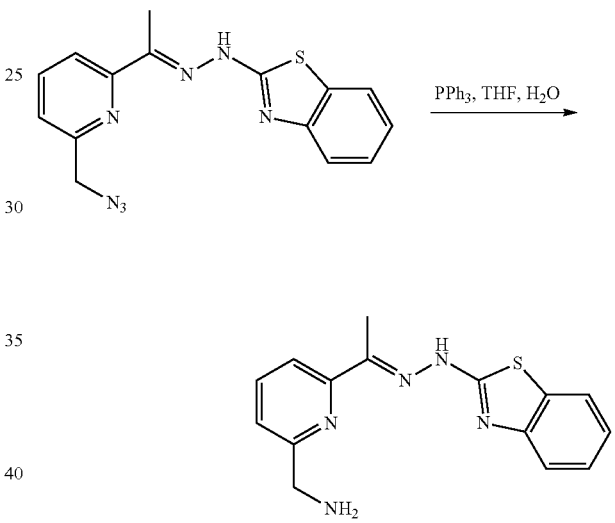

(E)(6-(1-(2-(benzo[d]thiazol-2-yl)hydrazono)ethyl)pyridin-2-yl)methanamine (E)-2-(2-(1-(6-(azidomethyl)pyridin-2-yl)ethylidene)hydrazinyl)benzo[d]thiazole was Synthesized Using General Method F and General Method a as Described To a solution of (E)-2-(2-(1-(6-(azidomethyl)pyridin-2-yl)ethylidene)hydrazinyl) benzo[d]thiazole (60 mg, 0.186 mmol, 1 eq) in THF (4 ml) and water (0.20 ml) was added triphenylphosphine (58.5 mg, 0.223 mmol, 1.2 eq). The reaction was stirred overnight at room temperature and partitioned in dilute aqueous HCl and DCM. The aqueous layer was washed 2×DCM to remove non-basic impurities, and then made basic with 1N NaOH. The basic aqueous layer was extracted 3×DCM, dried over sodium sulfate and concentrated. The residue was further purified by Prep HPLC to yield (E)-(6-(1-(2-(benzo[d]thiazol-2-yl)hydrazono)ethyl)pyridin-2-yl)methanamine (10.0 mg) as a yellow solid.

Method K.

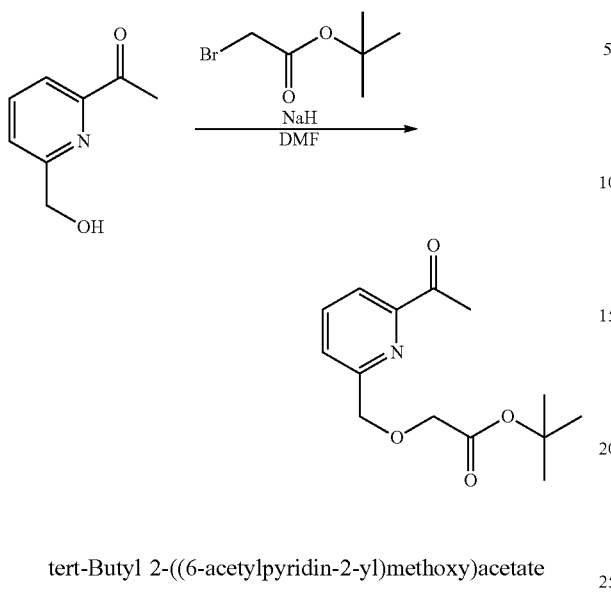

tert-Butyl 2-((6-acetylpyridin-2-yl)methoxy)acetate

To a solution of 1-(6-(hydroxymethyl)pyridin-2-yl)ethan-1-one (100 mg, 0.66 mmol, 1 eq) in DMF (2 ml) at 0° C. was added NaH (60% dispersion, 32 mg, 0.79 mmol, 1.2 eq). After stirring for 2 min at 0° C., tert-butyl 2-bromoacetate (117 ul, 0.79 mmol, 1.2 eq) was added, and the reaction was allowed to stir 1 hour the same temperature. The reaction was quenched with water and partitioned in EtOAc/water. The organic layer was washed 3×water, dried over sodium sulfate and concentrated. The crude product was purified by silica gel chromatography to yield tert-butyl 2-((6-acetylpyridin-2-yl)methoxy)acetate (75 mg, 43% yield) as a clear oil.

Method L.

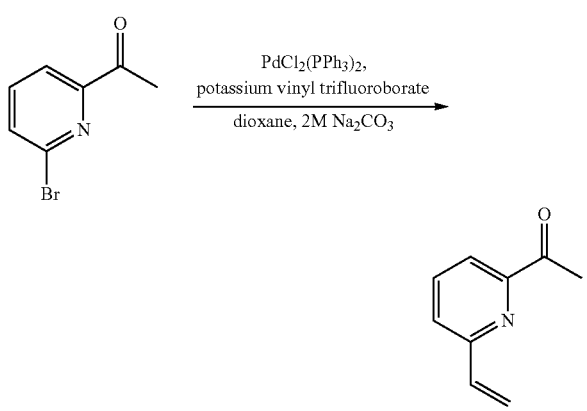

1-(6-vinylpyridin-2-yl)ethan-1-one 1-(6-bromopyridin-2-yl)ethan-1-one (250 mg, 1.25 mmol, 1 eq), potassium vinyl trifluoroborate (335 mg, 2.5 mmol, 2 eq), PdCl$_2$(PPh$_3$)$_2$ (44 mg, 0.063 mmol, 0.05 eq) in dioxane (3 ml) and 2M Na$_2$CO$_3$ (2 ml) were heated in a microwave reactor for 10 minutes at 120° C. The reaction was partitioned in EtOAc/water, extracted 2×EtOAc, dried over sodium sulfate and concentrated. The crude product was purified by silica gel chromatography to give 1-(6-vinylpyridin-2-yl)ethan-1-one (140 mg, 76% yield) as a clear oil.

Method M.

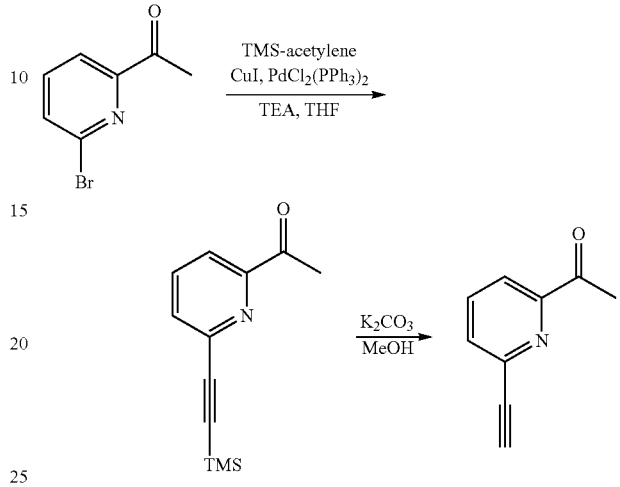

1-(6-ethynylpyridin-2-yl)ethan-1-one 1-(6-bromopyridin-2-yl)ethan-1-one (1.0 g. 5.0 mmol, 1 eq), CuI (38 mg, 0.2 mmol, 0.04 eq), PdCl$_2$(PPh$_3$)$_2$ (140 mg, 0.2 mmol, 0.04 eq) in THF (10 ml), TEA (1.5 ml) was degassed under bubbling nitrogen for 10 min. To this solution was added TMS-acetylene (1.42 ml, 10 mmol, 2 eq) and the reaction was stirred for 2 hours at RT. The reaction was diluted in hexanes and filtered over a plug of silica gel to remove the majority of impurities. The eluent was concentrated under reduced pressure and further purified by silica gel chromatography (5% EtOAc/Hexanes) to afford 1-(6-(((trimethylsilyl)ethynyl)pyridin-2-yl)ethan-1-one (1.09 g) as a yellow oil that was used without further purification. To a solution of 1-(6-(((trimethylsilyl)ethynyl)pyridin-2-yl)ethan-1-one (crude from previous reaction) in methanol (20 ml) was added a large excess of potassium carbonate. The reaction was stirred 2 hours at RT and concentrated under reduced pressure. The concentrate was partitioned in DCM/water, extracted 2×DCM, dried over sodium sulfate and concentrated. The crude product was purified by silica gel chromatography to give 1-(6-ethynylpyridin-2-yl)ethan-1-one (402 mg, 55% yield over 2 steps) as a white solid.

Method N.

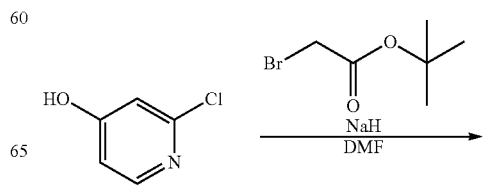

Method O.

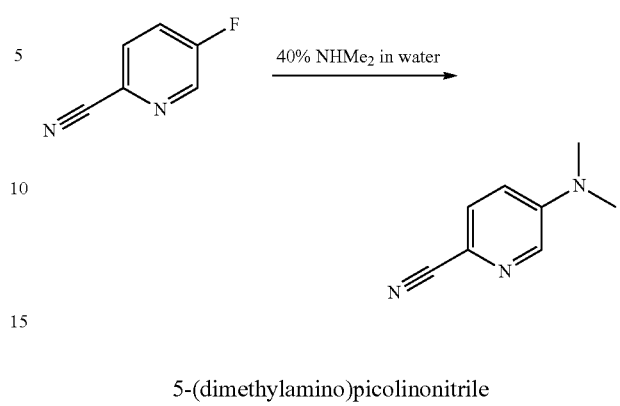

5-(dimethylamino)picolinonitrile 5-fluoropicolinonitrile (500 mg, 4.09 mmol, 1 eq) was taken up in a solution of dimethylamine (40% in water, 4 ml) and heated overnight at 100° C. in sealed reaction vial. The reaction was then concentrated to dryness under reduced pressure and purified by silica gel chromatography (25%→50% EtOAc/Hex) to afford 5-(dimethylamino)picolinonitrile (336 mg, 56% yield) as a white solid.

Method P (Example 39).

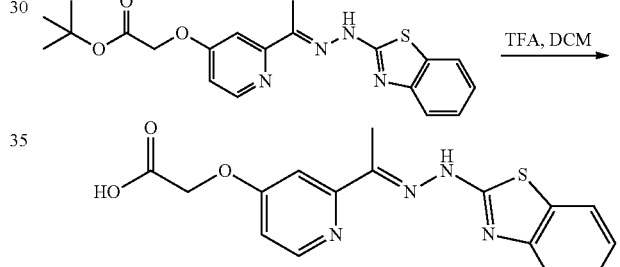

(E)-2-((2-(1-(2-(benzo[d]thiazol-2-yl)hydrazono) ethyl)pyridin-4-yl)oxy)acetic acid To a solution of tert-butyl (E)-2-((2-(1-(2-(benzo[d]thiazol-2-yl)hydrazono)ethyl)pyridin-4-yl)oxy)acetate (60 mg, 0.151 mmol, 1 eq) in DCM (3 ml) was added TFA (500 uL). The reaction was stirred overnight at RT and concentrated under reduced pressure and dried under high vacuum to afford (E)-2-((2-(1-(2-(benzo[d]thiazol-2-yl)hydrazono) ethyl)pyridin-4-yl)oxy)acetic acid (49 mg, 95% yield) as a yellow solid.

Method Q (Example 40).

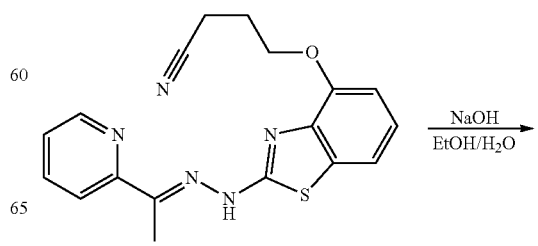

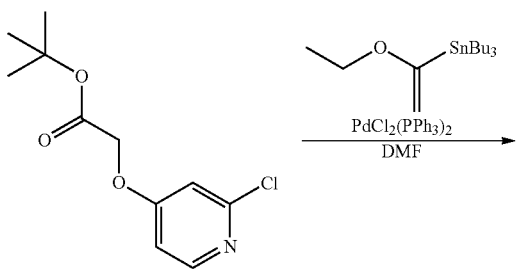

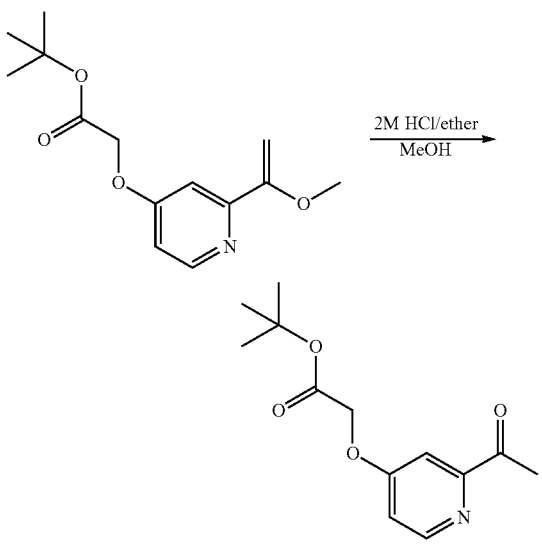

tert-Butyl 2-((2-acetylpyridin-4-yl)oxy)acetate

To a solution of 2-chloropyridin-4-ol (500 mg, 3.9 mmol, 1 eq) in DMF (10 ml) at 0° C., was added NaH (60%, 188 mg, 4.7 mmol, 1.2 eq). After stirring 10 min at 0° C., tert-butyl 2-bromoacetate (694 ul, 4.7 mmol, 1.2 eq) was added, and the reaction was stirred an additional 20 minutes. The reaction was quenched with saturated aqueous ammonium chloride and partitioned in EtOAc/water. The organic was washed 2×water, 1×brine, dried over sodium sulfate and concentrated. The crude product was purified by silica gel chromatography to yield tert-butyl 2-((2-chloropyridin-4-yl) oxy)acetate (793 mg, 83% yield) as a clear oil.

2-chloropyridin-4-ol (100 mg, 0.41 mmol, 1 eq), tributyl (1-ethoxyvinyl)stannane (166 ul, 0.49 mmol, 1.2 eq), PdCl$_2$(PPh$_3$)$_2$ (14 mg, 0.021 mmol, 0.05 eq), in DMF (1 ml) was degassed under bubbling nitrogen and heated in a microwave reactor for 10 minutes at 140° C. The reaction was partitioned in EtOAc/water, extracted 3×EtOAc, washed 3×water, 1×brine, dried over sodium sulfate and concentrated. The product was purified by silica gel chromatography to afford tert-butyl 2-((2-(1-methoxyvinyl)pyridin-4-yl) oxy)acetate (65 mg, 57% yield) as a light orange oil.

tert-butyl 2-((2-(1-methoxyvinyl)pyridin-4-yl)oxy)acetate (230 mg, 0.824 mmol, 1 eq) was dissolved in DCM (10 ml). To this solution was added HCl/ether (2M, 2 ml). The reaction was stirred 3 hours at RT and concentrated under reduced pressure. tert-Butyl 2-((2-acetylpyridin-4-yl)oxy) acetate (110 mg, 53% yield) was isolated as a white solid after purification by silica gel chromatography.

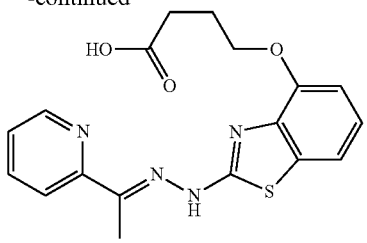

(E)-4-((2-(2-(1-(pyridin-2-yl)ethylidene)hydrazinyl)
benzo[d]thiazol-4-yl)oxy)butanoic acid (E)-4-((2-(2-(1-(pyridin-2-yl)ethylidene)hydrazinyl)
benzo[d]thiazol-4-yl)oxy)butanenitrile (0.076 g, 0.216 mmol, 1 equiv.) was dissolved in ethanol (4.5 mL) and water (1.5 mL) was added as the mixture stirred. NaOH (0.043 g, 1.08 mmol, 5 equiv.) was added and the mixture was heated to 75° C. for 72 hours. The mixture was cooled to ambient temperature and the solvent was removed via rotovap. The resulting residue was dissolved in water and acidified with 1M HCl$_{(aq)}$ to pH 5. The orange solid that precipitated was filtered and washed with methanol and ether to give (E)-4-((2-(2-(1-(pyridin-2-yl)ethylidene)hydrazinyl)benzo[d]thiazol-4-yl)oxy)butanoic acid (0.024 g, 0.065 mmol, 30%) as a red-orange solid.

Examples 8-43

The compounds of Examples 8-43 were prepared using the methods identified below. The structures, names, NMR data and mass spectral data for the compounds of Examples 8-43 are shown in Table 1.

TABLE 1

| Ex | Structure and Name | Methods | $^1$H NMR MS |
|----|-------|---------|-----|
| 8 | (E)-6-methoxy-2-(2-(1-(pyridin-2-yl)ethylidene)hydrazinyl)benzo[d]thiazole | B, A | $^1$H NMR (400 MHz, Chloroform-d) δ 8.95 (s, 1H), 8.59 (ddd, J = 5.0, 1.9, 1.1 Hz, 1H), 8.16 (dt, J = 8.2, 1.1 Hz, 1H), 7.78-7.66 (m, 1H), 7.53 (d, J = 8.7 Hz, 1H), 7.30-7.19 (m, 2H), 6.96 (ddd, J = 8.9, 2.7, 0.9 Hz, 1H), 3.86 (s, 3H), 2.42 (s, 3H). (MS + H)+ 298.85. |
| 9 | (E)-5-methoxy-2-(2-(1-(pyridin-2-yl)ethylidene)hydrazinyl)benzo[d]thiazole | B, A | $^1$H NMR (400 MHz, Chloroform-d) δ 8.94 (s, 1H), 8.59 (ddd, J = 4.9, 1.8, 1.0 Hz, 1H), 8.17 (dt, J = 8.2, 1.1 Hz, 1H), 7.73 (ddd, J = 8.1, 7.4, 1.8 Hz, 1H), 7.55 (d, J = 8.6 Hz, 1H), 7.31-7.20 (m, 2H), 7.17 (d, J = 2.5 Hz, 1H), 6.82 (dd, J = 8.6, 2.5 Hz, 1H), 3.87 (s, 3H), 2.44 (s, 3H). (MS + H)+ 298.85. |
| 10 | (E)-2-(2-(1-(4-methoxypyridin-2-yl)ethylidene)hydrazinyl)benzo[d]thiazole | A | $^1$H NMR (400 MHz, Chloroform-d) δ 9.02 (s, 1H), 8.41 (dd, J = 5.7, 1.7 Hz, 1H), 7.74-7.66 (m, 2H), 7.62 (d, J = 8.1 Hz, 1H), 7.36 (dddd, J = 8.1, 7.2, 2.1, 1.1 Hz, 1H), 7.24-7.15 (m, 1H), 6.83 (dt, J = 5.7, 2.2 Hz, 1H), 3.95 (s, 3H), 2.43 (s, 3H). (MS + H)+ 298.95 |
| 11 | (E)-2-(2-(1-(1-methyl-1H-benzo[d]imidazol-2-yl)ethylidene)hydrazinyl)benzo[d]thiazole | A | $^1$H NMR (400 MHz, Chloroform-d) δ 9.10 (s, 1H), 7.81 (dt, J = 7.9, 1.0 Hz, 1H), 7.71 (ddd, J = 7.9, 1.3, 0.6 Hz, 1H), 7.62 (ddd, J = 8.1, 1.2, 0.6 Hz, 1H), 7.47-7.38 (m, 1H), 7.40-7.34 (m, 2H), 7.31 (ddd, J = 8.3, 7.0, 1.3 Hz, 1H), 7.26-7.17 (m, 1H), 4.22 (s, 3H), 2.63 (s, 3H). (MS + H)+ 321.95 |

TABLE 1-continued

| Ex | Structure and Name | Methods | ¹H NMR MS |
|---|---|---|---|
| 12 | 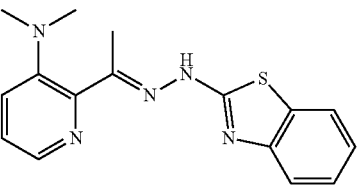 [SMILES: C/C(=N\Nc1nc2ccccc2s1)c1ncccc1N(C)C]<br>(E)-2-(1-(2-(benzo[d]thiazol-2-yl)hydrazono)ethyl)-N,N-dimethylpyridin-3-amine | O, E, A | ¹H NMR (400 MHz, Chloroform-d) δ 8.87 (s, 1H), 8.21 (dd, J = 4.5, 1.4 Hz, 1H), 7.70-7.63 (m, 1H), 7.60 (d, J = 8.0 Hz, 1H), 7.37-7.30 (m, 2H), 7.23-7.13 (m, 2H), 2.83 (s, 6H), 2.38 (s, 3H). (MS + H)+ 311.9 |
| 13 | 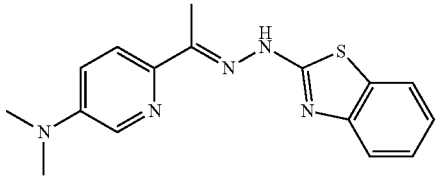 [SMILES: C/C(=N\Nc1nc2ccccc2s1)c1ccc(N(C)C)cn1]<br>(E)-6-(1-(2-(benzo[d]thiazol-2-yl)hydrazono)ethyl)-N,N-dimethylpyridin-4-amine | O, E, A | ¹H NMR (400 MHz, Chloroform-d) δ 8.70 (s, 1H), 8.07 (dd, J = 3.7, 1.9 Hz, 1H), 7.73-7.65 (m, 1H), 7.63-7.57 (m, 1H), 7.43-7.28 (m, 2H), 7.23-6.98 (m, 2H), 3.06 (s, 6H), 2.40 (s, 3H). (MS + H)+ 311.95 |
| 14 | 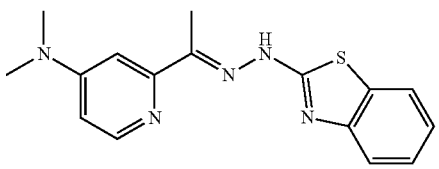 [SMILES: C/C(=N\Nc1nc2ccccc2s1)c1cc(N(C)C)ccn1]<br>(E)-2-(1-(2-(benzo[d]thiazol-2-yl)hydrazono)ethyl)-N,N-dimethylpyridin-4-amine | O, E, A | ¹H NMR (400 MHz, Chloroform-d) δ 8.91 (s, 1H), 8.26 (ddd, J = 19.9, 5.9, 1.4 Hz, 1H), 7.69 (t, J = 8.0 Hz, 1H), 7.62 (d, J = 8.3 Hz, 1H), 7.45-7.40 (m, 1H), 7.33 (dt, J = 17.6, 7.7 Hz, 1H), 7.15 (dt, J = 24.9, 7.5 Hz, 1H), 6.53 (ddt, J = 6.1, 4.4 1.8 Hz, 1H), 3.09 (d, J = 11.3 Hz, 6H), 2.42 (s, 3H). (MS + H)+ 311.85 |
| 15 | 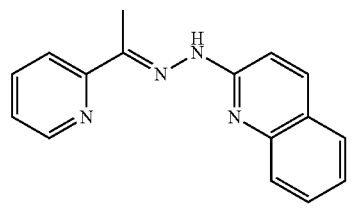 [SMILES: C/C(=N\Nc1ccc2ccccc2n1)c1ccccn1]<br>(E)-2-(2-(1-(pyridin-2-yl)ethylidene)hydrazinyl)quinoline | A | ¹H NMR (400 MHz, Chloroform-d) δ 8.64-8.58 (m, 1H), 8.55 (s, 1H), 8.21 (d, J = 8.0 Hz, 1H), 8.10 (d, J = 8.9 Hz, 1H), 7.85-7.68 (m, 4H), 7.62 (ddt, J = 8.5, 7.1, 1.6 Hz, 1H), 7.41-7.30 (m, 1H), 7.25-7.19 (m, 1H), 2.48 (s, 3H). (MS + H)+ 262.9 |
| 16 | 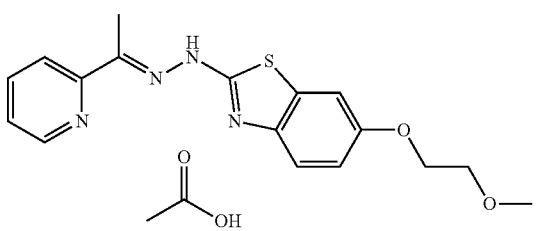<br>(E)-6-(2-methoxyethoxy)-2-(2-(1-(pyridin-2-yl)ethylidene)hydrazinyl)benzo[d]thiazole | G, C, A | ¹H NMR (acetate salt) (400 MHz, Chloroform-d) δ 8.68-8.56 (m, 1H), 8.15 (d, J = 8.3 Hz, 1H), 7.72 (td, J = 7.7, 1.8 Hz, 1H), 7.45 (d, J = 8.8 Hz, 1H), 7.27-7.22 (m, 2H), 6.99 (dd, J = 8.8, 2.5 Hz, 1H), 4.26-4.11 (m, 2H), 3.88-3.71 (m, 2H), 3.47 (s, 3H), 2.48 (s, 3H), 2.14 (s, 3H). (MS + H)+ 342.95 |

TABLE 1-continued

| Ex | Structure and Name | Methods | ¹H NMR MS |
|---|---|---|---|
| 17 | 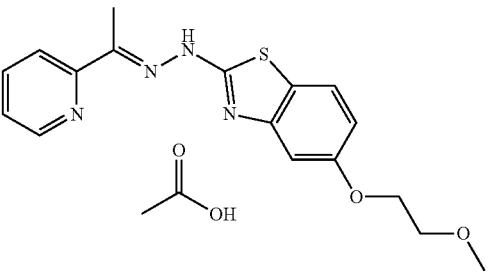<br>(E)-5-(2-methoxyethoxy)-2-(2-(1-(pyridin-2-yl)ethylidene)hydrazinyl)benzo[d]thiazole | G, C, A | ¹H NMR (acetate salt) (400 MHz, Chloroform-d) δ 8.66-8.56 (m, 1H), 8.16 (dp, J = 8.1, 0.9 Hz, 1H), 7.73 (tt, J = 6.4, 1.5 Hz, 1H), 7.52 (dd, J = 8.6, 1.9 Hz, 1H), 7.30-7.23 (m, 1H), 7.10 (t, J = 2.3 Hz, 1H), 6.85 (dt, J = 8.6, 2.3 Hz, 1H), 4.22-4.14 (m, 2H), 3.83-3.75 (m, 2H), 3.47 (s, 3H), 2.50 (s, 3H), 2.14 (s, 3H). (MS + H)+ 342.95 |
| 18 | 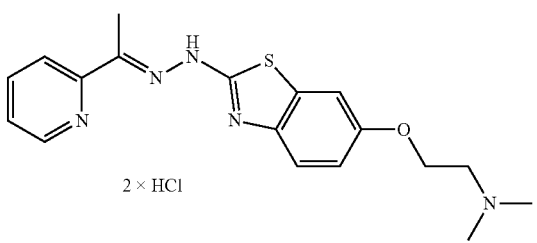 [SMILES: C/C(=N\Nc1nc2ccc(OCCN(C)C)cc2s1)c1ccccn1]<br>(E)-N,N-dimethyl-2-((2-(2-(1-(pyridin-2-yl)ethylidene)hydrazinyl)benzo[d]thiazol-6-yl)oxy)ethan-1-amine | G, C, A | ¹H NMR (HCl salt) (500 MHz, DMSO-$d_6$) δ 10.46 (s, 1H), 8.65 (d, J = 5.2 Hz, 1H), 8.14 (d, J = 7.9 Hz, 1H), 8.07 (s, 1H), 7.55 (s, 1H), 7.50 (d, J = 2.6 Hz, 1H), 7.38 (d, J = 9.1 Hz, 1H), 7.00 (dd, J = 8.7, 2.6 Hz, 1H), 4.40-4.33 (m, 2H), 3.49 (q, J = 5.3, 2H), 2.83 (d, J = 4.9 Hz, 6H), 2.42 (s, 3H). (MS + H)+ 356.1 |
| 19 | 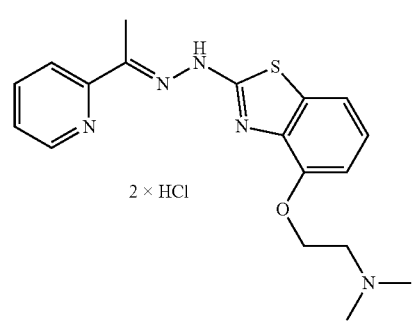 [SMILES: C/C(=N\Nc1nc2c(OCCN(C)C)cccc2s1)c1ccccn1]<br>(E)-N,N-dimethyl-2-((2-(2-(1-(pyridin-2-yl)ethylidene)hydrazinyl)benzo[d]thiazol-4-yl)oxy)ethan-1-amine | G, C, A | ¹H NMR (HCl salt) (500 MHz, DMSO-$d_6$) δ 10.34 (s, 1H), 8.64 (d, J = 5.3 Hz, 1H), 8.15 (d, J = 7.9 Hz, 1H), 8.03 (s, 1H), 7.53 (s, 1H), 7.36 (d, J = 7.8 Hz, 1H), 7.10 (t, J = 8.0 Hz, 1H), 7.01 (dd, J = 8.1, 1.0 Hz, 1H), 4.48 (t, J = 5.0 Hz, 2H), 3.54 (q, J = 5.2 Hz, 2H), 2.89 (d, J = 4.8 Hz, 6H), 2.44 (s, 3H). (MS + H)+ 356.05 |
| 20 | 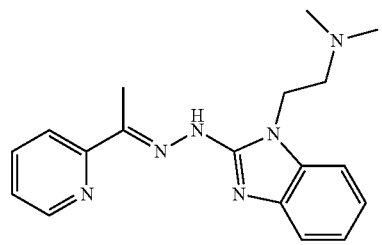<br>(E)-N,N-dimethyl-2-(2-(2-(1-(pyridin-2-yl)ethylidene)hydrazinyl)-1H-benzo[d]imidazol-1-yl)ethan-1-amine | H, C, A | ¹H NMR (HCl salt) (500 MHz, DMSO-$d_6$) δ 13.24 (s, 1H), 10.28 (s, 1H), 8.78 (dd, J = 6.0, 1.6 Hz, 1H), 8.52 (t, J = 7.9 Hz, 1H), 8.22 (d, J = 8.3 Hz, 1H), 7.82 (t, J = 6.6 Hz, 1H), 7.56-7.49 (m, 1H), 7.30 (dt, J = 7.6, 3.1 Hz, 1H), 7.21-7.13 (m, 2H), 4.63-4.51 (m, 2H), 3.54 (q, J = 5.7 Hz, 2H), 2.91 (d, J = 3.8 Hz, 6H), 2.42 (s, 3H). (MS + H)+ 323.1 |

TABLE 1-continued

| Ex | Structure and Name | Methods | $^1$H NMR MS |
|---|---|---|---|
| 21 | 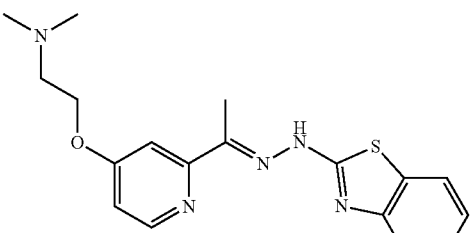

(E)-2-((2-(1-(2-(benzo[d]thiazol-2-yl)hydrazono)ethyl)pyridin-4-yl)oxy)-N,N-dimethylethan-1-amine | D, E, A | $^1$H NMR (HCl salt) (500 MHz, Methanol-d$_4$) δ 8.69 (d, J = 6.9 Hz, 1H), 7.82 (d, J = 2.6 Hz, 1H), 7.71-7.65 (m, 1H), 7.55 (dd, J = 6.9, 2.6 Hz, 1H), 7.46 (d, J = 8.1 Hz, 1H), 7.43-7.37 (m, 1H), 7.24 (td, J = 7.6, 1.2 Hz, 1H), 4.84-4.83 (m, 2H), 3.82-3.70 (m, 2H), 3.06 (s, 6H), 2.53 (s, 3H). (MS + H)+ 356.1 |
| 22 | 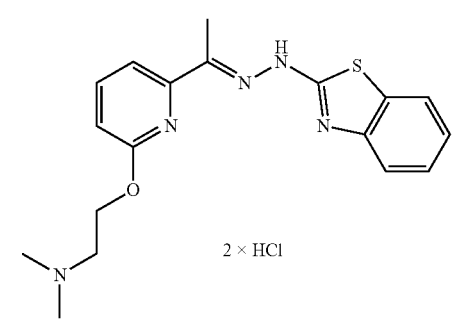 [SMILES: C/C(=N\Nc1nc2ccccc2s1)c1cccc(OCCN(C)C)n1]

(E)-2-((6-(1-(2-(benzo[d]thiazol-2-yl)hydrazono)ethyl)pyridin-2-yl)oxy)-N,N-dimethylethan-1-amine | D, E, A | $^1$H NMR (HCl salt) (500 MHz, DMSO-d$_6$) δ 10.35 (s, 1H), 7.88-7.79 (m, 1H), 7.80-7.70 (m, 2H), 7.41 (d, J = 8.6 Hz, 1H), 7.31 (td, J = 7.6, 1.3 Hz, 1H), 7.12 (td, J = 7.6, 1.2 Hz, 1H), 6.88 (dd, J = 8.1, 0.8 Hz, 1H), 4.73-4.66 (m, 2H), 3.59-3.51 (m, 2H), 2.85 (d, J = 4.9 Hz, 6H), 2.43 (s, 3H). (MS + H)+ 356 |
| 23 | 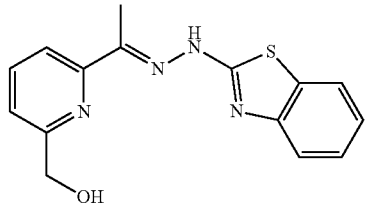 [SMILES: C/C(=N\Nc1nc2ccccc2s1)c1cccc(CO)n1]

(E)-(6-(1-(2-(benzo[d]thiazol-2-yl)hydrazono)ethyl)pyridin-2-yl)methanol | A | $^1$H NMR (500 MHz, Methanol-d$_4$) δ 8.04 (dd, J = 7.9, 1.0 Hz, 1H), 7.81 (t, J = 7.8 Hz, 1H), 7.68 (s, 1H), 7.59-7.41 (m, 2H), 7.31 (t, J = 7.4 Hz, 1H), 7.14 (t, J = 7.6 Hz, 1H), 4.72 (s, 2H), 2.46 (s, 3H). (MS + H)+ 298.85 |
| 24 | 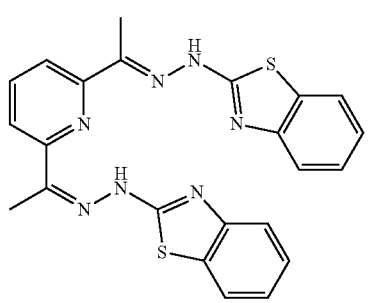

2-((E)-1-(2-(benzo[d]thiazol-2-yl)hydrazono)ethyl)-6-((Z)-1-(2-(benzo[d]thiazol-2-yl)hydrazono)ethyl)pyridine | A | 1H NMR (HCl salt) (500 MHz, DMSO-d6) δ 8.06 (d, J = 7.8 Hz, 2H), 7.92 (t, J = 7.8 Hz, 1H), 7.74 (d, J = 7.8 Hz, 2H), 7.40 (d, J = 8.1 Hz, 2H), 7.30 (td, J = 7.6, 1.3 Hz, 2H), 7.11 (td, J = 7.5, 1.2 Hz, 2H), 2.48 (s, 6H). (MS + H)+ 457.85 |

TABLE 1-continued

| Ex | Structure and Name | Methods | ¹H NMR MS |
|---|---|---|---|
| 25 | (E)-2-(2-(1-(pyridin-2-yl)ethylidene)hydrazinyl)thiazolo[5,4-c]pyridine | C, A | ¹H NMR (500 MHz, DMSO-$d_6$) δ 12.34 (s, 1H), 8.78 (s, 1H), 8.59 (dt, J = 4.6, 1.4 Hz, 1H), 8.31 (s, 1H), 8.08 (dt, J = 8.0, 1.1 Hz, 1H), 7.86 (td, J = 7.8, 1.8 Hz, 1H), 7.39 (ddd, J = 7.4, 4.8, 1.2 Hz, 1H), 7.29 (s, 1H), 2.43 (s, 3H). (MS + H)+ 269.9 |
| 26 | (E)-1-(6-(1-(2-(benzo[d]thiazol-2-yl)hydrazono)ethyl)pyridin-2-yl)-N,N-dimethylmethanamine (2 × HCl) | I, A | ¹H NMR (HCl salt) (500 MHz, DMSO-$d_6$) δ 10.35 (s, 1H), 8.10 (d, J = 8.1 Hz, 1H), 7.95 (t, J = 7.8 Hz, 1H), 7.73 (d, J = 7.8 Hz, 1H), 7.55 (dd, J = 7.6, 1.0 Hz, 1H), 7.39 (s, 1H), 7.30 (td, J = 7.7, 1.3 Hz, 1H), 7.15-7.07 (m, 1H), 4.46 (d, J = 5.3 Hz, 2H), 2.83 (d, J = 4.8 Hz, 6H), 2.47 (s, 3H). (MS + H)+ 325.85 |
| 27 | (E)-1-(6-(1-(2-(benzo[d]thiazol-2-yl)hydrazono)ethyl)pyridin-2-yl)-N-methyl-N-(pyridin-2-ylmethyl)methanamine (2 × HCl) | I, A | ¹H NMR (HCl salt) (500 MHz, DMSO-$d_6$) δ 8.67 (dt, J = 4.7, 1.4 Hz, 1H), 8.10 (d, J = 8.1 Hz, 1H), 7.98-7.90 (m, 2H), 7.73 (d, J = 7.8 Hz, 1H), 7.59 (d, J = 7.9 Hz, 1H), 7.54 (d, J = 7.4 Hz, 1H), 7.48 (ddd, J = 7.5, 4.8, 1.1 Hz, 1H), 7.40 (d, J = 8.1 Hz, 1H), 7.33-7.26 (m, 1H), 7.11 (t, J = 7.4 Hz, 1H), 4.61 (s, 2H), 4.57 (s, 2H), 2.90 (s, 3H), 2.42 (s, 3H). (MS + H)+ 402.75 |
| 28 | (E)-2-((2-(1-(2-(benzo[d]oxazol-2-yl)hydrazono)ethyl)pyridin-4-yl)oxy)-N,N-dimethylethan-1-amine (2 × HCl) | D, E, A | ¹H NMR (HCl salt) (500 MHz, Methanol-$d_4$) δ 8.75 (d, J = 6.8 Hz, 1H), 7.84 (d, J = 2.6 Hz, 1H), 7.56 (dd, J = 6.8, 2.6 Hz, 1H), 7.51-7.44 (m, 2H), 7.34 (td, J = 7.7, 1.1 Hz, 1H), 7.26 (td, J = 7.8, 1.3 Hz, 1H), 4.85-4.82 (m, 2H), 3.82-3.74 (m, 2H), 3.06 (s, 6H), 2.50 (s, 3H). (MS + H)+ 339.80 |

TABLE 1-continued

| Ex | Structure and Name | Methods | ¹H NMR MS |
|---|---|---|---|
| 29 | (E)-(6-(1-(2-(benzo[d]oxazol-2-yl)hydrazono)ethyl)pyridin-2-yl)methanol | A | 1H NMR (500 MHz, DMSO-d6) δ 11.39 (d, J = 109.0 Hz, 1H), 7.95 (s, 1H), 7.83 (t, J = 7.9 Hz, 1H), 7.61-7.27 (m, 3H), 7.15 (d, J = 46.7 Hz, 2H), 5.48-5.34 (m, 1H), 4.58 (d, J = 5.8 Hz, 2H), 2.38 (s, 3H). (MS + H)+ 283 |
| 30 | (E)-(6-(1-(2-(benzo[d]thiazol-2-yl)hydrazono)ethyl)pyridin-2-yl)methanamine | I, A, J | ¹H NMR (HCl salt) (400 MHz, Methanol-d₄) δ 8.46 (d, J = 7.9 Hz, 1H), 8.05-7.92 (m, 2H), 7.76 (d, J = 8.2 Hz, 1H), 7.66-7.54 (m, 2H), 7.48 (t, J = 7.7 Hz, 1H), 4.39 (s, 2H), 2.70 (s, 3H). (MS + H)+ 297.85 |
| 31 | (E)-N-methyl-2-(2-(2-(1-(pyridin-2-yl)ethylidene)hydrazinyl)-1H-benzo[d]imidazol-1-yl)ethan-1-amine | H, C, A | ¹H NMR (HCl salt) (500 MHz, DMSO-d₆) δ 13.13 (s, 1H), 8.94 (s, 2H), 8.77 (d, J = 5.1 Hz, 1H), 8.48 (s, 1H), 8.23 (d, J = 8.2 Hz, 1H), 7.79 (s, 1H), 7.53 (s, 1H), 7.32 (s, 1H), 7.22-7.12 (m, 2H), 4.48 (d, J = 7.2 Hz, 2H), 3.37 (p, J = 5.9 Hz, 2H), 2.62 (t, J = 5.3 Hz, 3H), 2.44 (s, 3H). (MS + H)+ 309.1 |
| 32 | (E)-2-(2-(1-(6-(azidomethyl)pyridin-2-yl)ethylidene)hydrazinyl)benzo[d]thiazole | I, A | ¹H NMR (500 MHz, DMSO-d₆) δ 11.90 (s, 1H), 8.03 (dd, J = 8.1, 1.0 Hz, 1H), 7.88 (t, J = 7.8 Hz, 1H), 7.73 (d, J = 7.7 Hz, 1H), 7.42-7.33 (m, 2H), 7.28 (td, J = 7.6, 1.3 Hz, 1H), 7.13-7.07 (m, 1H), 4.50 (s, 2H), 2.42 (s, 3H). (MS + H)+ 323.95 |
| 33 | (E)-2-(2-(1-(6-vinylpyridin-2-yl)ethylidene)hydrazinyl)benzo[d]thiazole | L, A | ¹H NMR (500 MHz, Chloroform-d) δ 9.03 (s, 1H), 8.05 (dd, J = 7.9, 0.9 Hz, 1H), 7.75-7.66 (m, 2H), 7.62 (ddd, J = 8.1, 1.2, 0.6 Hz, 1H), 7.36 (ddd, J = 8.0, 7.3, 1.3 Hz, 1H), 7.29-7.26 (m, 1H), 7.19 (ddd, J = 7.9, 7.3, 1.2 Hz, 1H), 6.83 (dd, J = 17.3, 10.7 Hz, 1H), 6.32 (dd, J = 17.3, 1.5 Hz, 1H), 5.49 (dd, J = 10.7, 1.5 Hz, 1H), 2.47 (s, 3H). (MS + H)+ 294.95 |

TABLE 1-continued

| Ex | Structure and Name | ¹H NMR Methods | MS |
|---|---|---|---|
| 34 | (E)-2-(2-(1-(6-ethynylpyridin-2-yl)ethylidenehydrazinyl)benzo[d]thiazole | M, A | ¹H NMR (500 MHz, Chloroform-d) δ 8.15 (dd, J = 8.1, 1.0 Hz, 1H), 7.74-7.69 (m, 2H), 7.62 (ddd, J = 8.1, 1.1, 0.6 Hz, 1H), 7.47 (dd, J = 7.6, 1.0 Hz, 1H), 7.39 (ddd, J = 8.1, 7.3, 1.2 Hz, 1H), 7.22 (ddd, J = 7.9, 7.3, 1.1 Hz, 1H), 3.17 (s, 1H), 2.48 (s, 3H). (MS + H)+ 292.8 |
| 35 | (E)-4-(2-(2-(2-(1-(pyridin-2-yl)ethylidene)hydrazinyl)-1H-benzo[d]imidazol-1-yl)ethyl)morpholine | H, C, A | ¹H NMR (HCl salt) (400 MHz, Methanol-$d_4$) δ 8.79 (ddd, J = 5.9, 1.6, 0.7 Hz, 1H), 8.61 (ddd, J = 8.2, 7.7, 1.6 Hz, 1H), 8.32-8.27 (m, 1H), 7.94 (ddd, J = 7.6, 5.8, 1.1 Hz, 1H), 7.55 (dd, J = 5.9, 3.2 Hz, 1H), 7.48-7.42 (m, 1H), 7.28 (dd, J = 5.9, 3.1 Hz, 2H), 4.81 (t, J = 6.4 Hz, 2H), 3.97 (s, 4H), 3.76 (t, J = 6.4 Hz, 2H), 3.59 (s, 4H), 2.57 (s, 3H). (MS + H)+ 364.95 (437.37) |
| 36 | (E)-2-(2-(1-(pyridin-2-yl)ethylidene)hydrazinyl)benzo[d]thiazole-5-carbonitrile | B, A | ¹H NMR (500 MHz, DMSO-$d_6$) δ 12.09 (s, 1H), 8.65-8.55 (m, 1H), 8.22-7.80 (m, 4H), 7.52 (d, J = 7.9 Hz, 1H), 7.39 (ddd, J = 7.3, 4.8, 1.2 Hz, 1H), 2.43 (s, 3H).<br>(MS + H)+ 293.85 |
| 37 | (E)-2-(2-(1-(pyridin-2-yl)ethylidene)hydrazinyl)benzo[d]thiazole-6-carbonitrile | B, A | ¹H NMR (500 MHz, DMSO-$d_6$) ? 12.16 (s, 1H), 8.60 (ddd, J = 4.8, 1.8, 0.9 Hz, 1H), 8.30 (s, 1H), 8.06 (dt, J = 8.2, 1.1 Hz, 1H), 7.87 (td, J = 7.8, 1.8 Hz, 1H), 7.71 (dd, J = 8.4, 1.8 Hz, 1H), 7.53 (s, 1H), 7.40 (ddd, J = 7.5, 4.8, 1.2 Hz, 1H), 2.44 (s, 3H). (MS + H)+ 293.85 |

TABLE 1-continued

| Ex | Structure and Name | Methods | ¹H NMR MS |
|---|---|---|---|
| 38 | (E)-2-((6-(1-(2-(benzo[d]thiazol-2-yl)hydrazono)ethyl)pyridin-2-yl)methoxy)acetic acid | K, A, P | ¹H NMR (500 MHz, DMSO-d₆) ? 12.28 (s, 1H), 7.98 (d, J = 8.0 Hz, 1H), 7.86 (t, J = 7.8 Hz, 1H), 7.73 (d, J = 7.9 Hz, 1H), 7.44 (d, J = 7.5 Hz, 1H), 7.38 (s, 1H), 7.28 (t, J = 7.3 Hz, 1H), 7.10 (t, J = 7.6 Hz, 1H), 4.66 (s, 2H), 4.18 (s, 2H), 2.39 (s, 3H). (MS + H)+ 356.95 |
| 39 | (E)-2-((2-(1-(2-(benzo[d]thiazol-2-yl)hydrazono)ethyl)pyridin-4-yl)oxy)acetic acid | N, A, P | ¹H NMR (400 MHz, DMSO-d₆) δ 8.40 (d, J = 5.7 Hz, 1H), 7.73 (s, 1H), 7.53 (d, J = 2.6 Hz, 1H), 7.38 (s, 1H), 7.29 (t, J = 7.6 Hz, 1H), 7.10 (t, J = 7.6 Hz, 1H), 6.98 (dd, J = 5.7, 2.6 Hz, 1H), 4.83 (s, 2H), 2.39 (s, 3H). (MS + H)+ 343 |
| 40 | (E)-4-((2-(2-(1-(pyridin-2-yl)ethylidene)hydrazinyl)benzo[d]thiazol-4-ol)oxy)butanoic acid | F, A, Q | ¹H NMR (HCl salt) (500 MHz, DMSO-d₆) δ 12.03 (bs, 2H), 8.62-8.57 (m, 1H), 8.07 (d, J = 8.1 Hz, 1H), 7.86 (td, J = 7.7, 1.8 Hz, 1H), 7.41-7.33 (m, 2H), 7.07 (t, J = 7.9 Hz, 1H), 6.92 (d, J = 8.0 Hz, 1H), 4.11 (t, J = 6.2 Hz, 2H), 2.48-2.46 (m, 2H), 2.42 (s, 3H), 1.99 (p, J = 7.0 Hz, 2H). (MS + H)+ 370.80 |
| 41 | (E)-2-(2-(1-(pyridin-2-yl)ethylidene)hydrazinyl)benzo[d]thiazol-4-ol | A | ¹H NMR (500 MHz, DMSO-d₆) δ 11.69 (bs, 1H), 9.59 (bs, 1H), 8.59 (ddd, J = 4.8, 1.8, 1.0 Hz, 1H), 8.07 (d, J = 8.1 Hz, 1H), 7.85 (td, J = 7.8, 1.8 Hz, 1H), 7.38 (ddd, J = 7.4, 4.8, 1.2 Hz, 1H), 7.21 (bs, 1H), 6.95 (t, J = 7.9 Hz, 1H), 6.76 (dd, J = 7.9, 1.1 Hz, 1H), 2.42 (s, 3H). (MS + H)+ 285.00 |

TABLE 1-continued

| Ex | Structure and Name | Methods | $^1$H NMR MS |
|----|---|---|---|
| 42 | 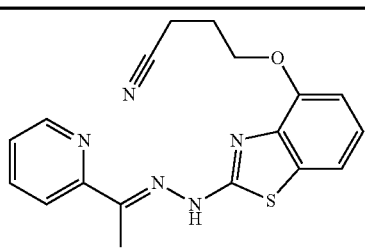<br>(E)-4-((2-(2-(1-(pyridin-2-yl)ethylidene)hydrazinyl)benzo[d]thiazol-4-yl)oxy)butanenitrile | F, A | $^1$H NMR (500 MHz, DMSO-d$_6$) δ 8.59 (ddd, J = 4.8, 1.8, 1.0 Hz, 1H), 8.07 (dt, J = 8.1, 1.1 Hz, 1H), 7.86 (ddd, J = 8.1, 7.4, 1.8 Hz, 1H), 7.44-7.32 (m, 2H), 7.08 (t, J = 8.0 Hz, 1H), 6.95 (dd, J = 8.2, 1.0 Hz, 1H), 4.16 (t, J = 6.0 Hz, 2H), 2.76 (t, J = 7.3 Hz, 2H), 2.43 (s, 3H), 2.08 (tt, J = 7.3, 5.9 Hz, 2H).<br>(MS + H)+ 352.20 |
| 43 | 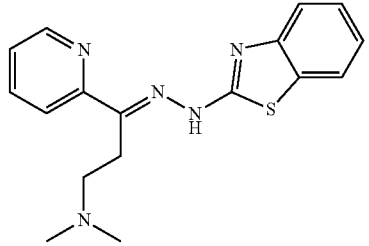 [SMILES: CN(C)CC/C(=N\Nc1nc2ccccc2s1)c1ccccn1]<br>(E)-3-(2-(benzo[d]thiazol-2-yl)hydrazono)-N,N-dimethyl-3-(pyridin-2-yl)propan-1-amine | A | $^1$H NMR (HCl salt) (500 MHz, Methanol-d$_4$) δ 8.83-8.77 (m, 1H), 8.57 (t, J = 8.0 Hz, 1H), 8.39 (dt, J = 8.4, 1.0 Hz, 1H), 7.94 (t, J = 6.7 Hz, 1H), 7.64 (dd, J = 7.9, 1.0 Hz, 1H), 7.44-7.33 (m, 2H), 7.23 (ddd, J = 7.8, 7.1, 1.4 Hz, 1H), 3.56-3.50 (m, 2H), 3.49-3.44 (m, 2H), 3.06 (s, 6H).<br>(MS + H)+ 326.25 |

Cell-based TOV112D activity and zinc binding for representative compounds is shown in Table 2.

TABLE 2

| Example | Structure | TOV112D IC$_{50}$* | Zinc Binding** |
|---|---|---|---|
| 5 | 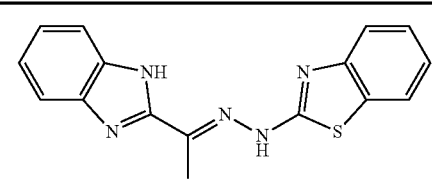 | | |
| 6 | 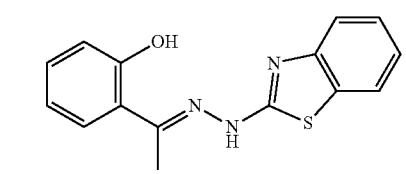 [SMILES: C/C(=N\Nc1nc2ccccc2s1)c1ccccc1O] | | |
| 7 | 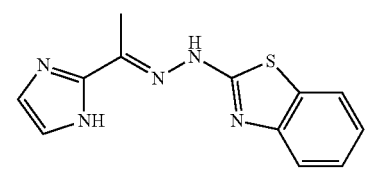 [SMILES: C/C(=N\Nc1nc2ccccc2s1)c1ncc[nH]1] | + | |

TABLE 2-continued
| Example | Structure | TOV112D IC$_{50}$* | Zinc Binding** |
|---|---|---|---|
| 18 | 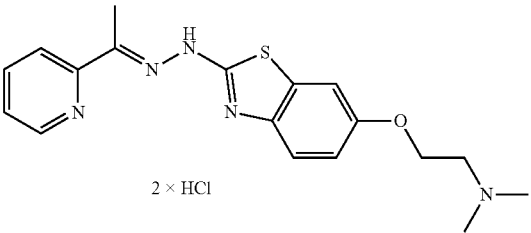 [SMILES: C/C(=N\Nc1nc2ccc(OCCN(C)C)cc2s1)c1ccccn1] 2 × HCl | ++ | + |
| 21 | 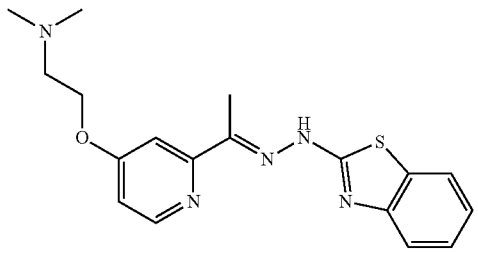 2 × HCl | ++ | ++ |
| 22 | 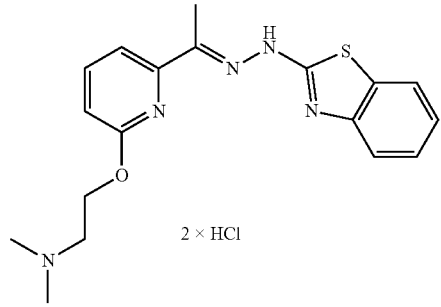 [SMILES: C/C(=N\Nc1nc2ccccc2s1)c1cccc(OCCN(C)C)n1] 2 × HCl | − | − |
| 23 | 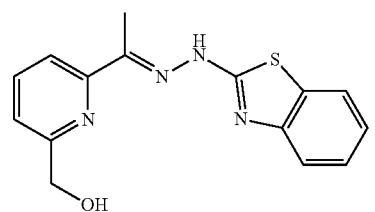 [SMILES: C/C(=N\Nc1nc2ccccc2s1)c1cccc(CO)n1] | + | + |
| 25 | 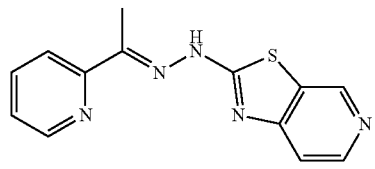 [SMILES: C/C(=N\Nc1nc2ccncc2s1)c1ccccn1] | + | + |
| 27 | 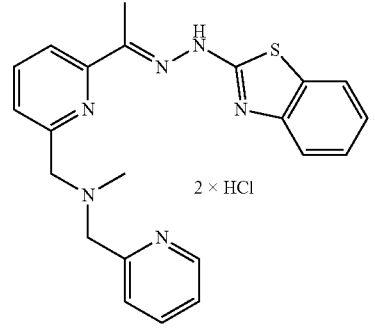 [SMILES: C/C(=N\Nc1nc2ccccc2s1)c1cccc(CN(C)Cc2ccccn2)n1] 2 × HCl | − | +++ |

TABLE 2-continued
| Example | Structure | TOV112D IC$_{50}$* | Zinc Binding** |
|---|---|---|---|
| 28 | 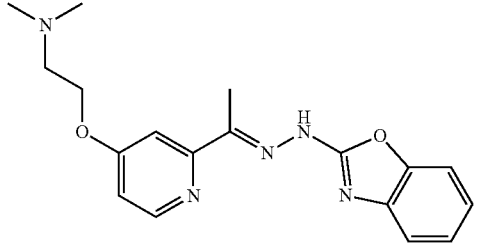 2 × HCl | +++ | ++ |
| 29 | 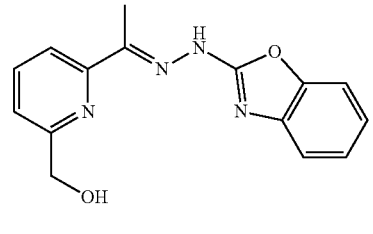 | + | + |
| 31 | 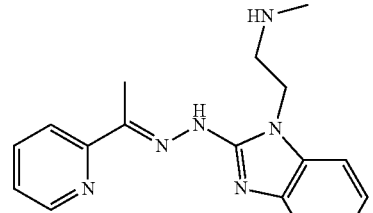 2 × HCl | +++ | ++ |
| 35 | 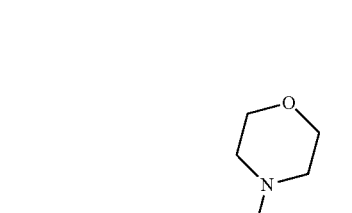 2 × HCl | +++ | ++ |
*+++, most active;
++, moderately active;
+, less active
− no measureable activity
**+++, tight binding;
++, moderately binding;
+, weaker binding;
− no measureable binding All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula (I):

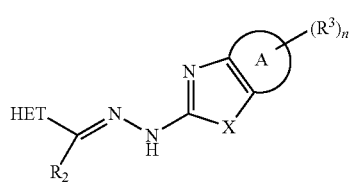

or a salt thereof, wherein:
the ring A is a fused benzo;
X is S, O, —CH=CH—, or N—R$^a$;
HET is selected from the group consisting of:

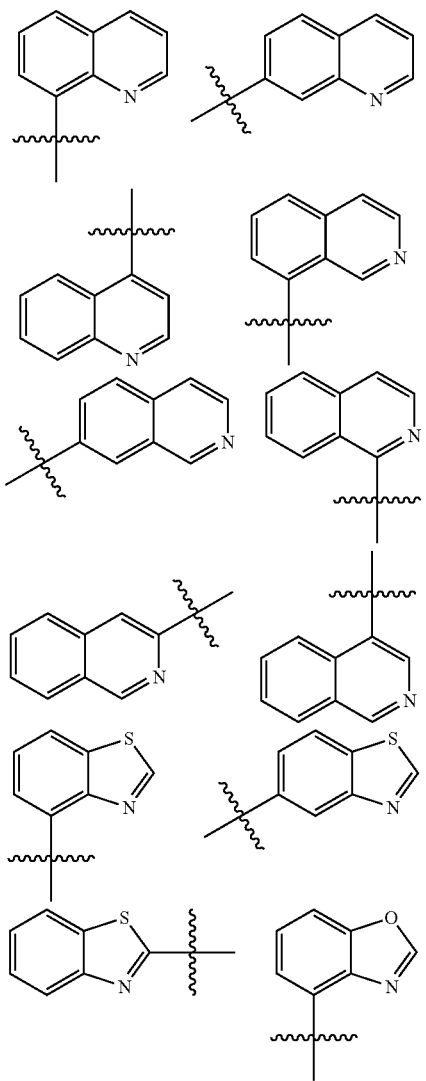

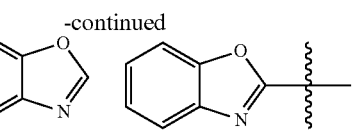

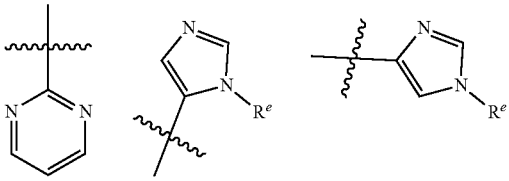

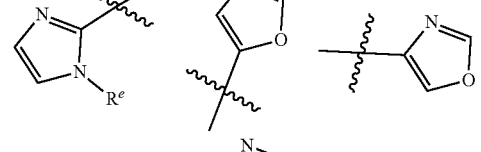

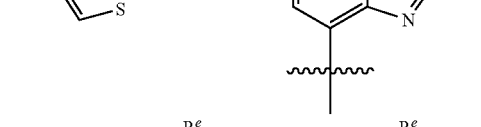

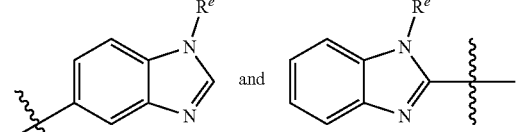

and wherein HET is optionally substituted with one or more groups R$^1$ independently selected from halo, cyano, hydroxy, nitro, —N(R$^a$)$_2$, carboxy, phenyl, (C$_1$-C$_6$)alkyl, (C$_2$-C$_6$)alkenyl, (C$_2$-C$_6$)alkynyl, (C$_3$-C$_6$)cycloalkyl, (C$_1$-C$_6$)alkoxy, (C$_1$-C$_6$)alkanoyl, (C$_1$-C$_6$)alkoxycarbonyl, (C$_2$-C$_6$)alkanoyloxy,

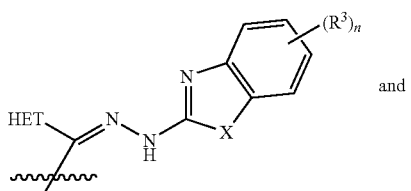

and

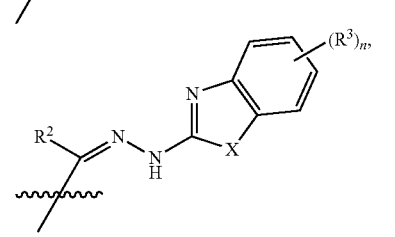

wherein any phenyl, $(C_1-C_6)$alkyl, $(C_1-C_6)$alkoxy, $(C_2-C_6)$alkenyl, $(C_2-C_6)$alkynyl, and $(C_3-C_6)$cycloalkyl, is optionally substituted with one or more groups independently selected from halo, azido, cyano, hydroxy, nitro, —N(R$^b$)$_2$, carboxy, $(C_3-C_6)$cycloalkyl, $(C_1-C_6)$alkanoyl, $(C_1-C_6)$alkoxycarbonyl, $(C_2-C_6)$alkanoyloxy, and $(C_1-C_6)$alkoxy that is optionally substituted with carboxy;

each R$^2$ is independently selected from the group consisting of H, phenyl, $(C_1-C_6)$alkyl, $(C_2-C_6)$alkenyl, $(C_2-C_6)$alkynyl, and $(C_3-C_6)$cycloalkyl, wherein any phenyl, $(C_1-C_6)$alkyl, $(C_2-C_6)$alkenyl, $(C_2-C_6)$alkynyl, and $(C_3-C_6)$cycloalkyl, is optionally substituted with one or more groups independently selected from halo, —N(R$^c$)$_2$, $(C_3-C_6)$cycloalkyl, $(C_1-C_6)$alkoxy, and $(C_2-C_6)$alkanoyloxy;

n is 0, 1, 2, 3, or 4;

each R$^3$ is independently selected from halo, cyano, hydroxy, —N(R$^d$)$_2$, carboxy, phenyl, $(C_1-C_6)$alkyl, $(C_2-C_6)$alkenyl, $(C_2-C_6)$alkynyl, $(C_3-C_6)$cycloalkyl, $(C_1-C_6)$alkoxy, $(C_1-C_6)$alkanoyl, $(C_1-C_6)$alkoxycarbonyl, and $(C_2-C_6)$alkanoyloxy, wherein any phenyl, $(C_1-C_6)$alkyl, $(C_2-C_6)$alkenyl, $(C_2-C_6)$alkynyl, $(C_1-C_6)$alkoxy, and $(C_3-C_6)$cycloalkyl, is optionally substituted with one or more groups independently selected from halo, cyano, hydroxy, nitro, —N(R$^e$)$_2$, carboxy, $(C_3-C_6)$cycloalkyl, $(C_1-C_6)$alkoxy, $(C_1-C_6)$alkanoyl, $(C_1-C_6)$alkoxycarbonyl, and $(C_2-C_6)$alkanoyloxy;

R$^a$ is selected from the group consisting of H, $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, wherein any $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, is optionally substituted with one or more groups independently selected from halo, $(C_3-C_6)$cycloalkyl, —N(R$^g$)$_2$, morpholino, and $(C_1-C_6)$alkoxy; or two R$^a$ taken together with the nitrogen to which they are attached form a azetidino, pyrrolidino, piperidino, or morpholino ring;

each R$^b$ is independently selected from the group consisting of H, $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, wherein any $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, is optionally substituted with one or more groups independently selected from halo, $(C_3-C_6)$cycloalkyl, heteroaryl, and $(C_1-C_6)$alkoxy; or two R$^b$ taken together with the nitrogen to which they are attached form an azetidino, pyrrolidino, piperidino, or morpholino ring; and each R$^c$ is independently selected from the group consisting of H, $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, wherein any $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, is optionally substituted with one or more groups independently selected from halo, $(C_3-C_6)$cycloalkyl, and $(C_1-C_6)$alkoxy; or two R$^c$ taken together with the nitrogen to which they are attached form a azetidino, pyrrolidino, piperidino, or morpholino ring;

each R$^d$ is independently selected from the group consisting of H, $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, wherein any $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, is optionally substituted with one or more groups independently selected from halo, $(C_3-C_6)$cycloalkyl, and $(C_1-C_6)$alkoxy; or two R$^d$ taken together with the nitrogen to which they are attached form a azetidino, pyrrolidino, piperidino, or morpholino ring;

R$^e$ is independently selected from the group consisting of H and $(C_1-C_6)$alkyl that is optionally substituted with one or more groups independently selected from halo, $(C_3-C_6)$cycloalkyl, —N(R$^f$)$_2$, and $(C_1-C_6)$alkoxy;

each R$^f$ is independently selected from the group consisting of H, $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, wherein any $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, is optionally substituted with one or more groups independently selected from halo, $(C_3-C_6)$cycloalkyl, and $(C_1-C_6)$alkoxy; or two R$^f$ taken together with the nitrogen to which they are attached form a azetidino, pyrrolidino, piperidino, or morpholino ring; and each R$^g$ is independently selected from the group consisting of H, $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, wherein any $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, is optionally substituted with one or more groups independently selected from halo, $(C_3-C_6)$cycloalkyl, and $(C_1-C_6)$alkoxy; or two R$^g$ taken together with the nitrogen to which they are attached form a azetidino, pyrrolidino, piperidino, or morpholino ring;

wherein if HET is not substituted with one or more groups R$^1$, then R$^2$ is not H, methyl, ethyl, propyl, isopropyl, butyl, tert-butyl, cyclopropyl, cyclohexyl, phenyl, benzyl or 2-pyridyl; and provided the compound is not:

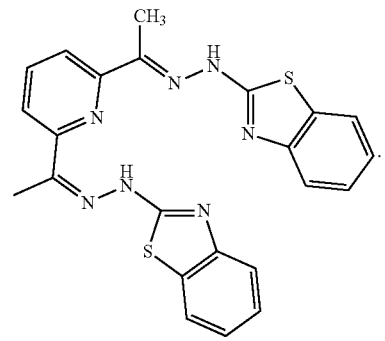 [SMILES: C/C(=N/Nc1nc2ccccc2s1)c1cccc(/C(C)=N/Nc2nc3ccccc3s2)n1]

2. The compound of claim 1 which is a compound of formula (Ia):

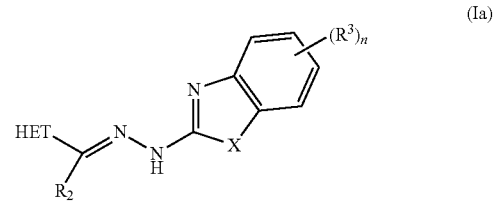

or a salt thereof, wherein:

X is S, O, N—H, or N—$R^a$;

HET is selected from the group consisting of:

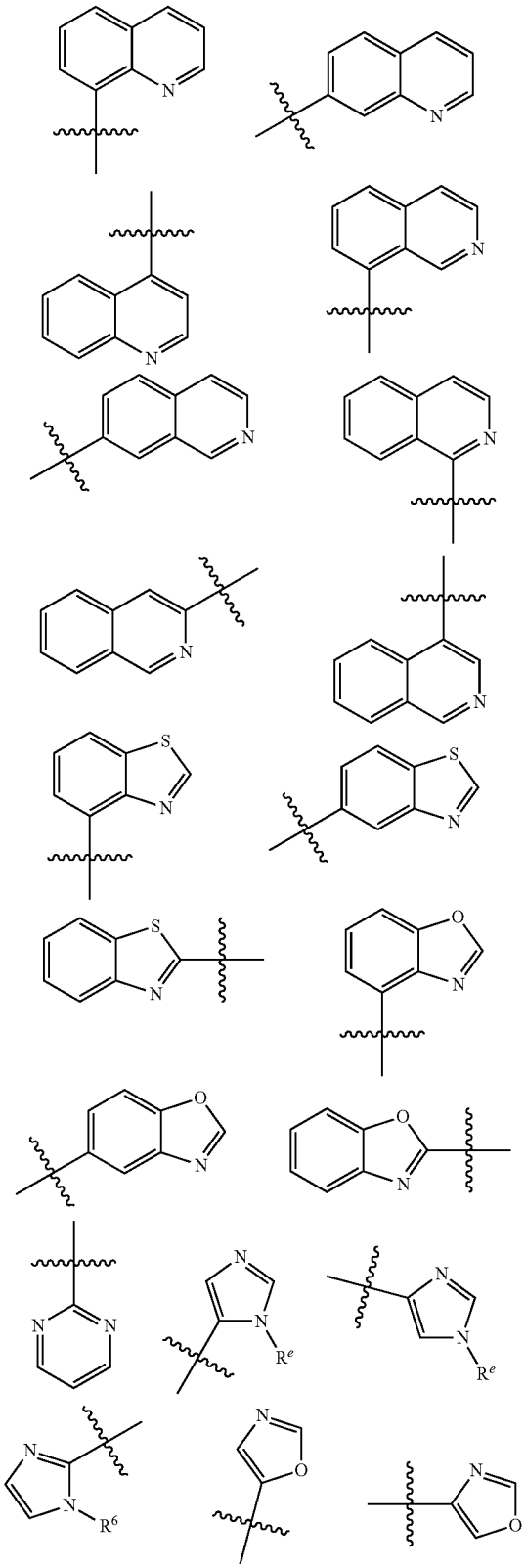

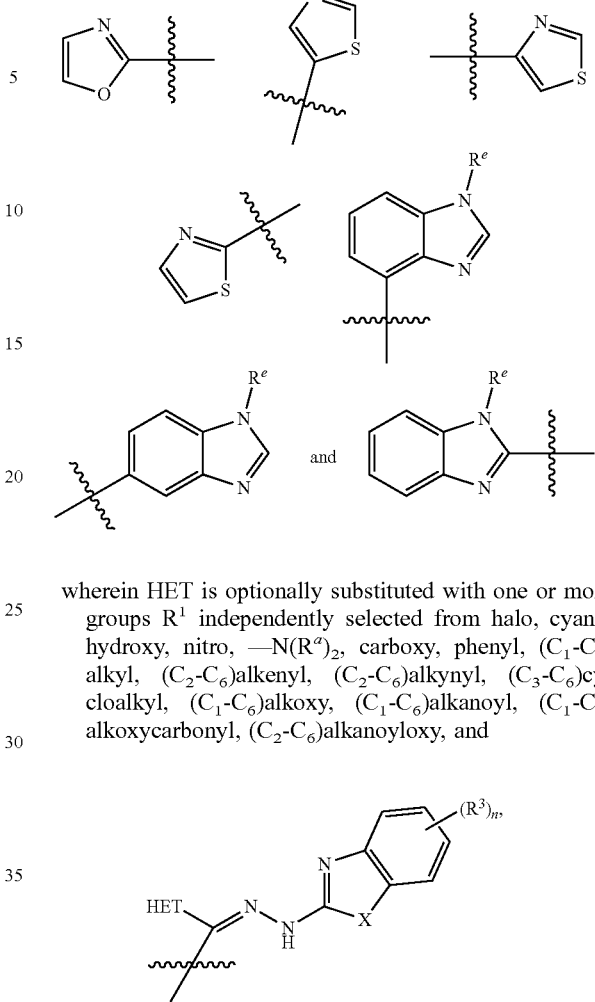

wherein HET is optionally substituted with one or more groups $R^1$ independently selected from halo, cyano, hydroxy, nitro, —N($R^a$)$_2$, carboxy, phenyl, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkoxy, ($C_1$-$C_6$)alkanoyl, ($C_1$-$C_6$)alkoxycarbonyl, ($C_2$-$C_6$)alkanoyloxy, and wherein any phenyl, ($C_1$-$C_6$)alkyl, ($C_1$-$C_6$)alkoxy, ($C_2$-$C_6$)alkenyl, ($C_2$-$C_6$)alkynyl, and ($C_3$-$C_6$)cycloalkyl, is optionally substituted with one or more groups independently selected from halo, cyano, hydroxy, nitro, —N($R^b$)$_2$, carboxy, ($C_3$-$C_6$)cycloalkyl, ($C_1$-$C_6$)alkoxy, ($C_1$-$C_6$)alkanoyl, ($C_1$-$C_6$)alkoxycarbonyl, and ($C_2$-$C_6$)alkanoyloxy;

$R^2$ is selected from the group consisting of H, phenyl, ($C_1$-$C_6$)alkyl, ($C_2$-$C_6$)alkenyl, ($C_2$-$C_6$)alkynyl, and ($C_3$-$C_6$)cycloalkyl, wherein any phenyl, ($C_1$-$C_6$)alkyl, ($C_2$-$C_6$)alkenyl, ($C_2$-$C_6$)alkynyl, and ($C_3$-$C_6$)cycloalkyl, is optionally substituted with one or more groups independently selected from halo, —N($R^c$)$_2$, ($C_3$-$C_6$)cycloalkyl, ($C_1$-$C_6$)alkoxy, and ($C_2$-$C_6$)alkanoyloxy;

n is 1, 2, 3, or 4;

each $R^3$ is independently selected from halo, cyano, hydroxy, —N($R^d$)$_2$, carboxy, phenyl, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkoxy, ($C_1$-$C_6$)alkanoyl, ($C_1$-$C_6$)alkoxycarbonyl, and ($C_2$-$C_6$)alkanoyloxy, wherein any phenyl, ($C_1$-$C_6$)alkyl, ($C_2$-$C_6$)alkenyl, ($C_2$-$C_6$)alkynyl, ($C_1$-$C_6$)alkoxy, and ($C_3$-$C_6$)cycloalkyl, is optionally substituted with one or more groups independently selected from halo, cyano, hydroxy, nitro, —N($R^c$)$_2$, carboxy, ($C_3$-$C_6$)cycloalkyl, ($C_1$-$C_6$)alkoxy, ($C_1$-$C_6$)alkanoyl, ($C_1$-$C_6$)alkoxycarbonyl, and ($C_2$-$C_6$)alkanoyloxy;

$R^a$ is selected from the group consisting of H, $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, wherein any $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, is optionally substituted with one or more groups independently selected from halo, $(C_3-C_6)$cycloalkyl, and $(C_1-C_6)$alkoxy; or two $R^a$ taken together with the nitrogen to which they are attached form a azetidino, pyrrolidino, piperidino, or morpholino ring;

each $R^b$ is independently selected from the group consisting of H, $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, wherein any $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, is optionally substituted with one or more groups independently selected from halo, $(C_3-C_6)$cycloalkyl, heteroaryl, and $(C_1-C_6)$alkoxy; or two $R^b$ taken together with the nitrogen to which they are attached form an azetidino, pyrrolidino, piperidino, or morpholino ring; and each $R^c$ is independently selected from the group consisting of H, $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, wherein any $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, is optionally substituted with one or more groups independently selected from halo, $(C_3-C_6)$cycloalkyl, and $(C_1-C_6)$alkoxy; or two $R^c$ taken together with the nitrogen to which they are attached form a azetidino, pyrrolidino, piperidino, or morpholino ring;

each $R^d$ is independently selected from the group consisting of H, $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, wherein any $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, is optionally substituted with one or more groups independently selected from halo, $(C_3-C_6)$cycloalkyl, and $(C_1-C_6)$alkoxy; or two $R^d$ taken together with the nitrogen to which they are attached form a azetidino, pyrrolidino, piperidino, or morpholino ring;

$R^e$ is independently selected from the group consisting of H and $(C_1-C_6)$alkyl that is optionally substituted with one or more groups independently selected from halo, $(C_3-C_6)$cycloalkyl, —$N(R^f)_2$, and $(C_1-C_6)$alkoxy; and each $R^f$ is independently selected from the group consisting of H, $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, wherein any $(C_1-C_6)$alkyl, $(C_2-C_6)$alkenyl, $(C_2-C_6)$alkynyl, $(C_3-C_6)$cycloalkyl, $(C_1-C_6)$alkanoyl, and $(C_1-C_6)$alkoxycarbonyl, is optionally substituted with one or more groups independently selected from halo, $(C_3-C_6)$cycloalkyl, and $(C_1-C_6)$alkoxy; or two $R^f$ taken together with the nitrogen to which they are attached form a azetidino, pyrrolidino, piperidino, or morpholino ring;

wherein if HET is not substituted with one or more groups $R^1$, then $R^2$ is not H, methyl, ethyl, propyl, isopropyl, butyl, tert-butyl, cyclopropyl, cyclohexyl, phenyl, benzyl or 2-pyridyl.

3. The compound of claim 1 or a salt thereof, wherein:
HET is selected from the group consisting of:

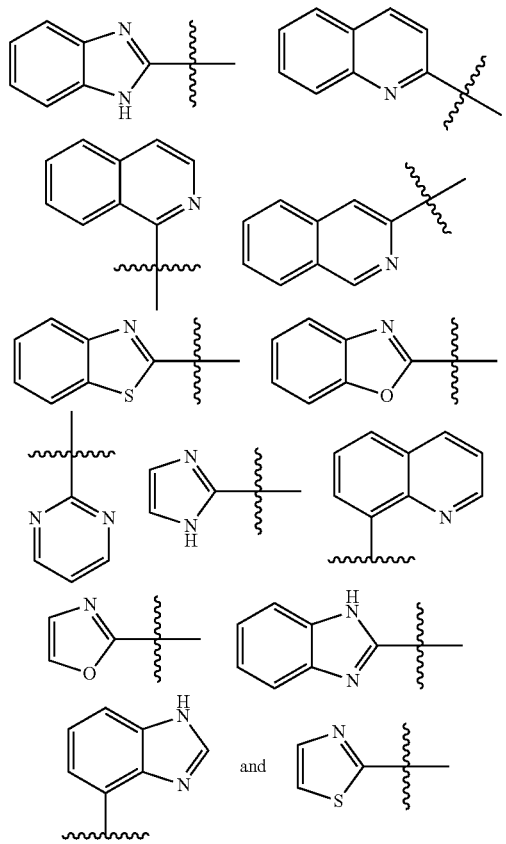

wherein HET is optionally substituted with one or more groups independently selected from halo, cyano, hydroxy, nitro, —$N(R^a)_2$, carboxy, phenyl, $(C_1-C_6)$alkyl, $(C_2-C_6)$alkenyl, $(C_2-C_6)$alkynyl, $(C_3-C_6)$cycloalkyl, $(C_1-C_6)$alkoxy, $(C_1-C_6)$alkanoyl, $(C_1-C_6)$alkoxycarbonyl, and $(C_2-C_6)$alkanoyloxy, wherein any phenyl, $(C_1-C_6)$alkyl, $(C_2-C_6)$alkenyl, $(C_2-C_6)$alkynyl, and $(C_3-C_6)$cycloalkyl, is optionally substituted with one or more groups independently selected from halo, cyano, hydroxy, nitro, —$N(R^a)_2$, carboxy, $(C_3-C_6)$cycloalkyl, $(C_1-C_6)$alkoxy, $(C_1-C_6)$alkanoyl, $(C_1-C_6)$alkoxycarbonyl, and $(C_2-C_6)$alkanoyloxy;

$R^2$ is selected from the group consisting of H, phenyl, $(C_1-C_6)$alkyl, $(C_2-C_6)$alkenyl, $(C_2-C_6)$alkynyl, and $(C_3-C_6)$cycloalkyl, wherein any phenyl, $(C_1-C_6)$alkyl, $(C_2-C_6)$alkenyl, $(C_2-C_6)$alkynyl, and $(C_3-C_6)$cycloalkyl, is optionally substituted with one or more groups independently selected from halo, —$N(R^b)_2$, $(C_3-C_6)$cycloalkyl, $(C_1-C_6)$alkoxy, and $(C_2-C_6)$alkanoyloxy;

or $R^1$ and $R^2$ taken together with the carbon to which they are attached form a bicyclic 9- or 10-membered nitrogen ring system comprising 1, 2, 3, or 4 nitrogen atoms and at least one aromatic ring;

n is 1, 2, 3, or 4;

each $R^3$ is independently selected from halo, cyano, hydroxy, —$N(R^d)_2$, carboxy, phenyl, $(C_1-C_6)$alkyl, $(C_2-C_6)$alkenyl, $(C_2-C_6)$alkynyl, $(C_3-C_6)$cycloalkyl, $(C_1-C_6)$alkoxy, $(C_1-C_6)$alkanoyl, $(C_1-C_6)$alkoxycarbonyl, and $(C_2-C_6)$alkanoyloxy, wherein any phenyl, $(C_1-C_6)$alkyl, $(C_2-C_6)$alkenyl, $(C_2-C_6)$alkynyl, $(C_1-C_6)$alkoxy, and $(C_3-C_6)$cycloalkyl, is optionally substituted with one or more groups independently selected from halo, cyano, hydroxy, nitro, —$N(R^c)_2$, carboxy, $(C_3$-

$C_6$)cycloalkyl, ($C_1$-$C_6$)alkoxy, ($C_1$-$C_6$)alkanoyl, ($C_1$-$C_6$)alkoxycarbonyl, and ($C_2$-$C_6$)alkanoyloxy;

each $R^a$ is independently selected from the group consisting of H, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, wherein any ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, is optionally substituted with one or more groups independently selected from halo, ($C_3$-$C_6$)cycloalkyl, and ($C_1$-$C_6$)alkoxy; or two $R^a$ taken together with the nitrogen to which they are attached form a azetidino, pyrrolidino, piperidino, or morpholino ring; and each $R^b$ is independently selected from the group consisting of H, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, wherein any ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, is optionally substituted with one or more groups independently selected from halo, ($C_3$-$C_6$)cycloalkyl, and ($C_1$-$C_6$)alkoxy; or two $R^b$ taken together with the nitrogen to which they are attached form a azetidino, pyrrolidino, piperidino, or morpholino ring;

each $R^c$ is independently selected from the group consisting of H, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, wherein any ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, is optionally substituted with one or more groups independently selected from halo, ($C_3$-$C_6$)cycloalkyl, and ($C_1$-$C_6$)alkoxy; or two $R^c$ taken together with the nitrogen to which they are attached form a azetidino, pyrrolidino, piperidino, or morpholino ring; and each $R^d$ is independently selected from the group consisting of H, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, wherein any ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, is optionally substituted with one or more groups independently selected from halo, ($C_3$-$C_6$)cycloalkyl, and ($C_1$-$C_6$)alkoxy; or two $R^d$ taken together with the nitrogen to which they are attached form a azetidino, pyrrolidino, piperidino, or morpholino ring.

4. A compound of formula (I):

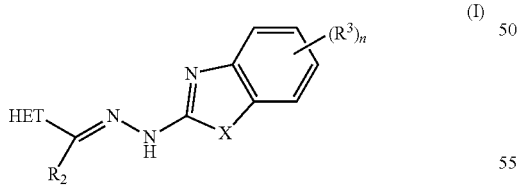

or a salt thereof, wherein:
X is S, O, N—H, or N-Me;
HET is selected from the group consisting of:

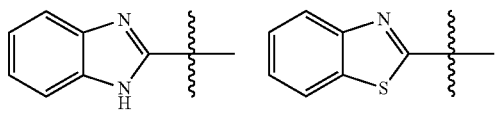

-continued

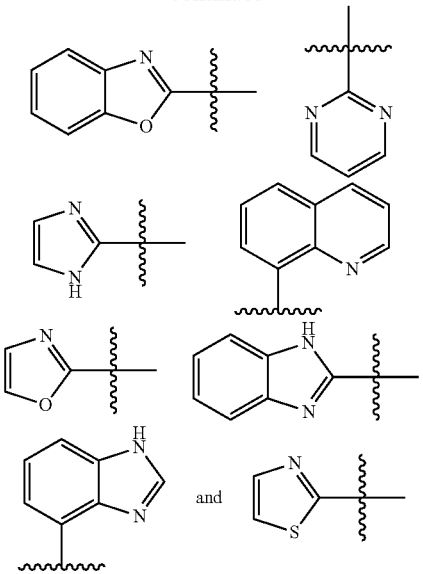

wherein HET is optionally substituted with one or more groups independently selected from halo, cyano, hydroxy, nitro, —N($R^a$)$_2$, carboxy, phenyl, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkoxy, ($C_1$-$C_6$)alkanoyl, ($C_1$-$C_6$)alkoxycarbonyl, and ($C_2$-$C_6$)alkanoyloxy, wherein any phenyl, ($C_1$-$C_6$)alkyl, ($C_2$-$C_6$)alkenyl, ($C_2$-$C_6$)alkynyl, and ($C_3$-$C_6$)cycloalkyl, is optionally substituted with one or more groups independently selected from halo, cyano, hydroxy, nitro, —N($R^a$)$_2$, carboxy, ($C_3$-$C_6$)cycloalkyl, ($C_1$-$C_6$)alkoxy, ($C_1$-$C_6$)alkanoyl, ($C_1$-$C_6$)alkoxycarbonyl, and ($C_2$-$C_6$)alkanoyloxy;

$R^2$ is selected from the group consisting of H, phenyl, ($C_1$-$C_6$)alkyl, ($C_2$-$C_6$)alkenyl, ($C_2$-$C_6$)alkynyl, and ($C_3$-$C_6$)cycloalkyl, wherein any phenyl, ($C_1$-$C_6$)alkyl, ($C_2$-$C_6$)alkenyl, ($C_2$-$C_6$)alkynyl, and ($C_3$-$C_6$)cycloalkyl, is optionally substituted with one or more groups independently selected from halo, —N($R^b$)$_2$, ($C_3$-$C_6$)cycloalkyl, ($C_1$-$C_6$)alkoxy, and ($C_2$-$C_6$)alkanoyloxy;

n is 0, 1, 2, 3, or 4;

each $R^3$ is independently selected from halo, cyano, hydroxy, —N($R^c$)$_2$, carboxy, phenyl, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkoxy, ($C_1$-$C_6$)alkanoyl, ($C_1$-$C_6$)alkoxycarbonyl, and ($C_2$-$C_6$)alkanoyloxy, wherein any phenyl, ($C_1$-$C_6$)alkyl, ($C_2$-$C_6$)alkenyl, ($C_2$-$C_6$)alkynyl, ($C_1$-$C_6$)alkoxy, and ($C_3$-$C_6$)cycloalkyl, is optionally substituted with one or more groups independently selected from halo, cyano, hydroxy, nitro, —N($R^c$)$_2$, carboxy, ($C_3$-$C_6$)cycloalkyl, ($C_1$-$C_6$)alkoxy, ($C_1$-$C_6$)alkanoyl, ($C_1$-$C_6$)alkoxycarbonyl, and ($C_2$-$C_6$)alkanoyloxy;

each $R^a$ is independently selected from the group consisting of H, ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, wherein any ($C_1$-$C_6$)alkyl, ($C_2$-$C_6$)alkenyl, ($C_2$-$C_6$)alkynyl, ($C_3$-$C_6$)cycloalkyl, ($C_1$-$C_6$)alkanoyl, and ($C_1$-$C_6$)alkoxycarbonyl, is optionally substituted with one or more groups independently selected from halo, ($C_3$-$C_6$)cycloalkyl, and ($C_1$-$C_6$)alkoxy; or two $R^a$ taken together with the nitrogen to which they are attached form a azetidino, pyrrolidino, piperidino, or morpholino ring;

each R$^b$ is independently selected from the group consisting of H, (C$_1$-C$_6$)alkyl, (C$_2$-C$_6$)alkenyl, (C$_2$-C$_6$)alkynyl, (C$_3$-C$_6$)cycloalkyl, (C$_1$-C$_6$)alkanoyl, and (C$_1$-C$_6$)alkoxycarbonyl, wherein any (C$_1$-C$_6$)alkyl, (C$_2$-C$_6$)alkenyl, (C$_2$-C$_6$)alkynyl, (C$_3$-C$_6$)cycloalkyl, (C$_1$-C$_6$)alkanoyl, and (C$_1$-C$_6$)alkoxycarbonyl, is optionally substituted with one or more groups independently selected from halo, (C$_3$-C$_6$)cycloalkyl, and (C$_1$-C$_6$)alkoxy; or two R$^b$ taken together with the nitrogen to which they are attached form a azetidino, pyrrolidino, piperidino, or morpholino ring; and each R$^c$ is independently selected from the group consisting of H, (C$_1$-C$_6$)alkyl, (C$_2$-C$_6$)alkenyl, (C$_2$-C$_6$)alkynyl, (C$_3$-C$_6$)cycloalkyl, (C$_1$-C$_6$)alkanoyl, and (C$_1$-C$_6$)alkoxycarbonyl, wherein any (C$_1$-C$_6$)alkyl, (C$_2$-C$_6$)alkenyl, (C$_2$-C$_6$)alkynyl, (C$_3$-C$_6$)cycloalkyl, (C$_1$-C$_6$)alkanoyl, and (C$_1$-C$_6$)alkoxycarbonyl, is optionally substituted with one or more groups independently selected from halo, (C$_3$-C$_6$)cycloalkyl, and (C$_1$-C$_6$)alkoxy; or two R$^c$ taken together with the nitrogen to which they are attached form a azetidino, pyrrolidino, piperidino, or morpholino ring.

5. The compound or salt of claim 4 wherein each HET is independently selected from the group consisting of:

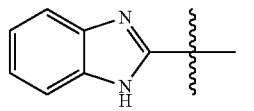 and 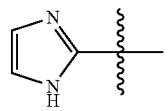

wherein HET is optionally substituted with one or more groups independently selected from halo, cyano, hydroxy, nitro, —N(R$^a$)$_2$, carboxy, phenyl, (C$_1$-C$_6$)alkyl, (C$_2$-C$_6$)alkenyl, (C$_2$-C$_6$)alkynyl, (C$_3$-C$_6$)cycloalkyl, (C$_1$-C$_6$)alkoxy, (C$_1$-C$_6$)alkanoyl, (C$_1$-C$_6$)alkoxycarbonyl, and (C$_2$-C$_6$)alkanoyloxy, wherein any phenyl, (C$_1$-C$_6$)alkyl, (C$_2$-C$_6$)alkenyl, (C$_2$-C$_6$)alkynyl, and (C$_3$-C$_6$)cycloalkyl, is optionally substituted with one or more groups independently selected from halo, cyano, hydroxy, nitro, —N(R$^a$)$_2$, carboxy, (C$_3$-C$_6$)cycloalkyl, (C$_1$-C$_6$)alkoxy, (C$_1$-C$_6$)alkanoyl, (C$_1$-C$_6$)alkoxycarbonyl, and (C$_2$-C$_6$)alkanoyloxy.

6. The compound or salt of claim 4 wherein each HET is independently selected from the group consisting of:

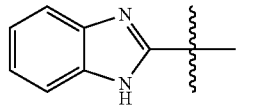 and 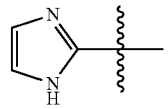

wherein HET is optionally substituted with one or more groups independently selected from (C$_1$-C$_6$)alkyl and —N(R$^a$)$_2$.

7. The compound or salt of claim 4 wherein R$^2$ is selected from the group consisting of H, methyl, ethyl, propyl, isopropyl, butyl, tert-butyl, allyl, cyclopropyl, phenyl, benzyl, CH$_2$CH$_2$OCH$_3$, and CH$_2$CH$_2$—N(CH$_3$)$_2$.

8. The compound or salt of claim 4 wherein R$^2$ is selected from the group consisting of methyl, ethyl, isopropyl, and tert-butyl.

9. A compound that is selected from the group consisting of:

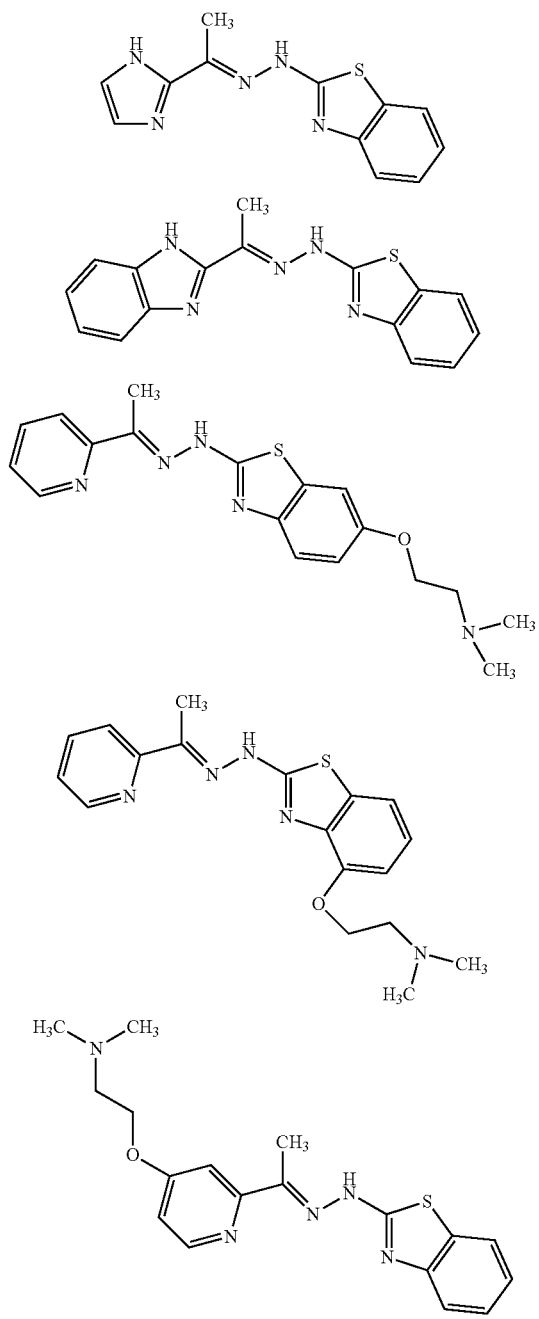
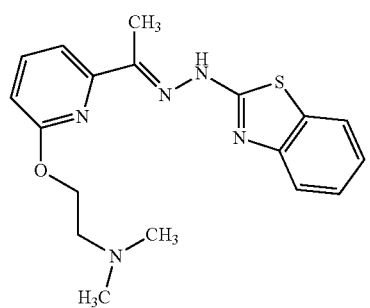

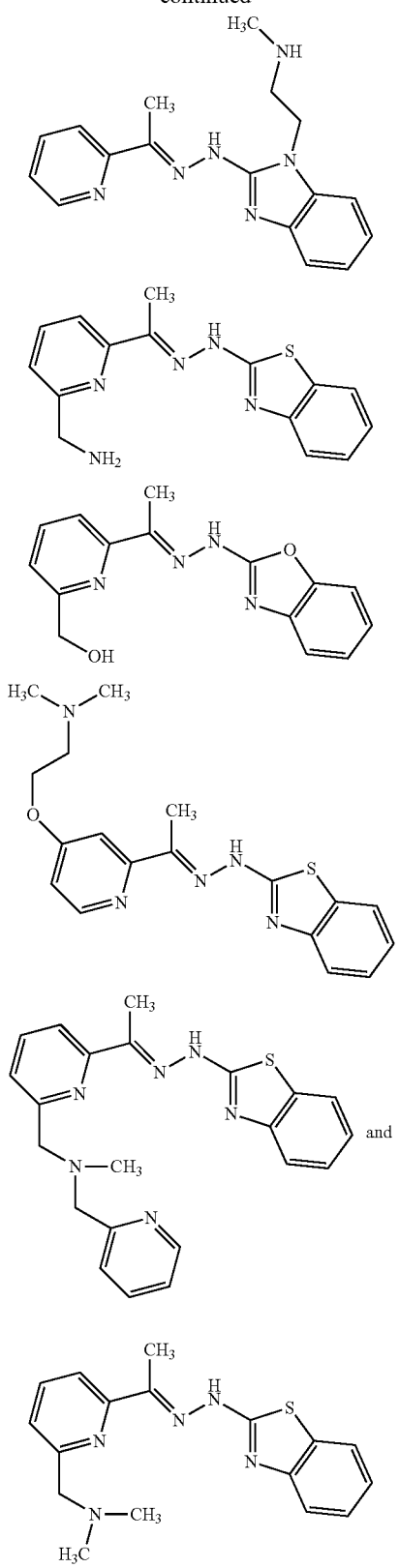
or a salt thereof.
10. A compound that is selected from the group consisting of:
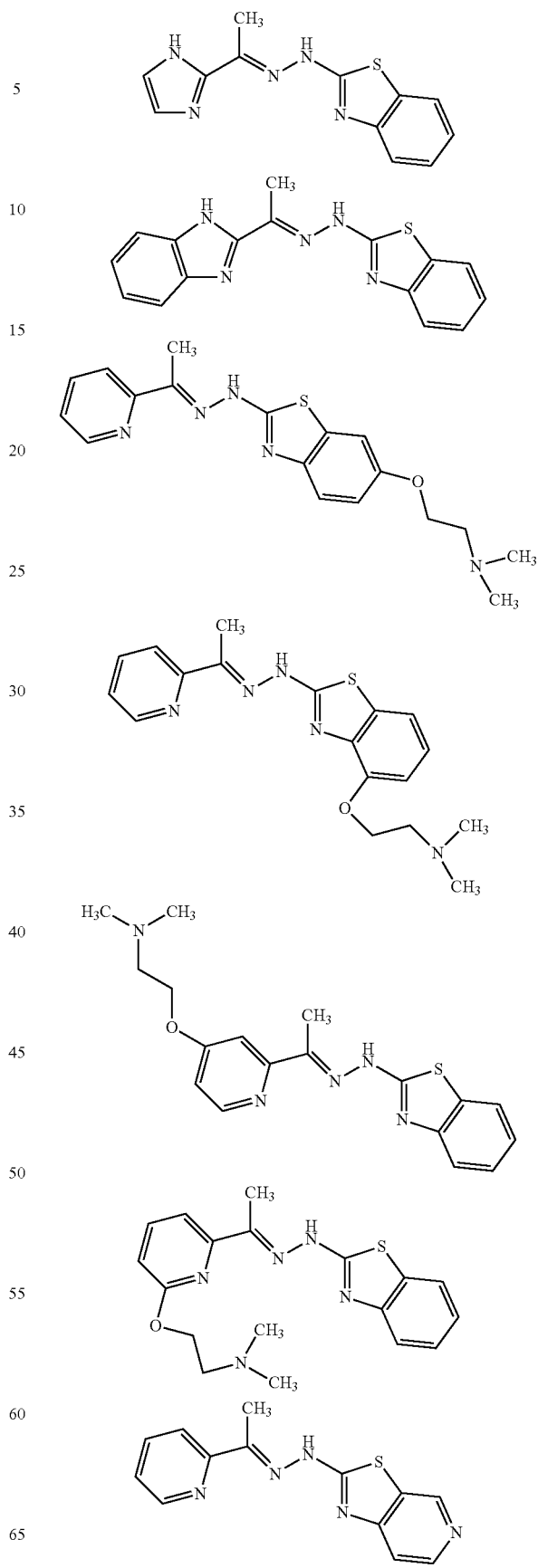

77
-continued
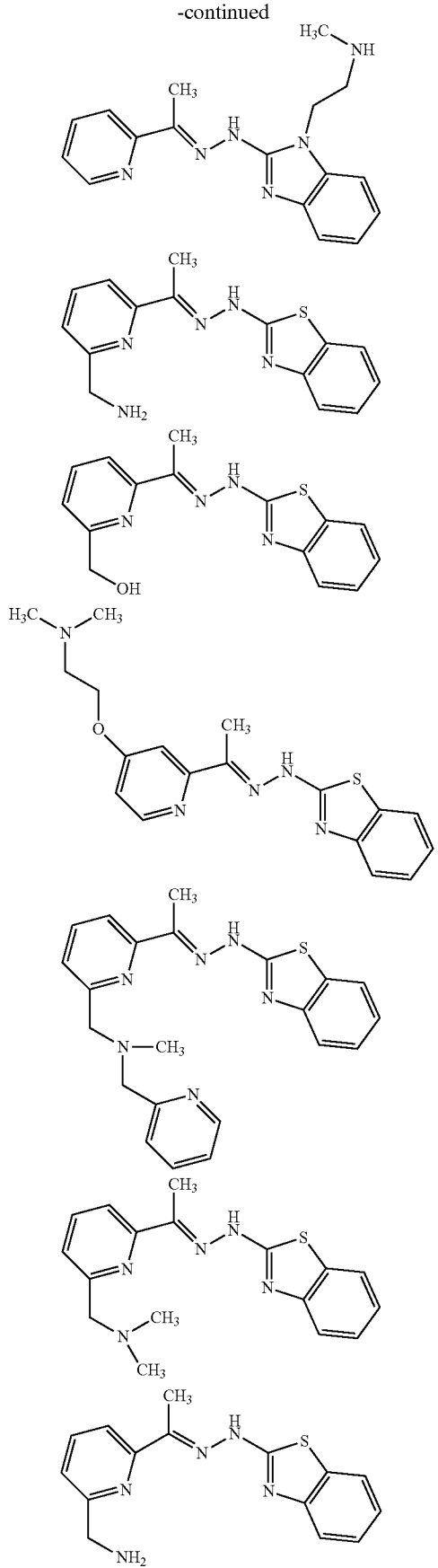
78
-continued
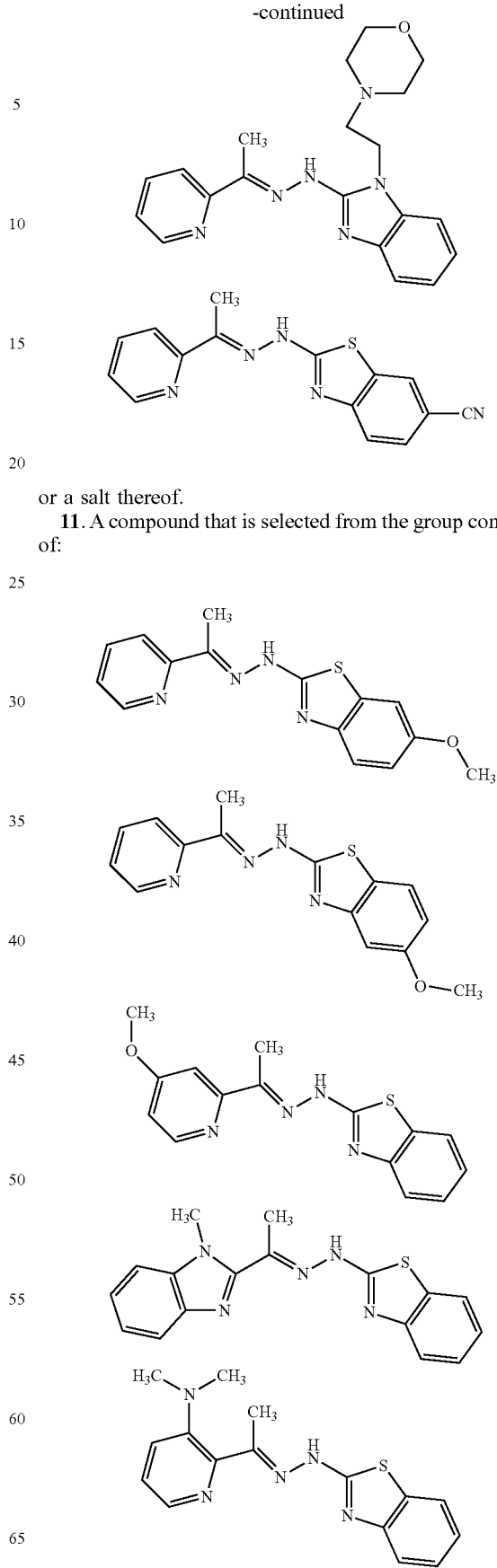
or a salt thereof.
11. A compound that is selected from the group consisting of:

-continued
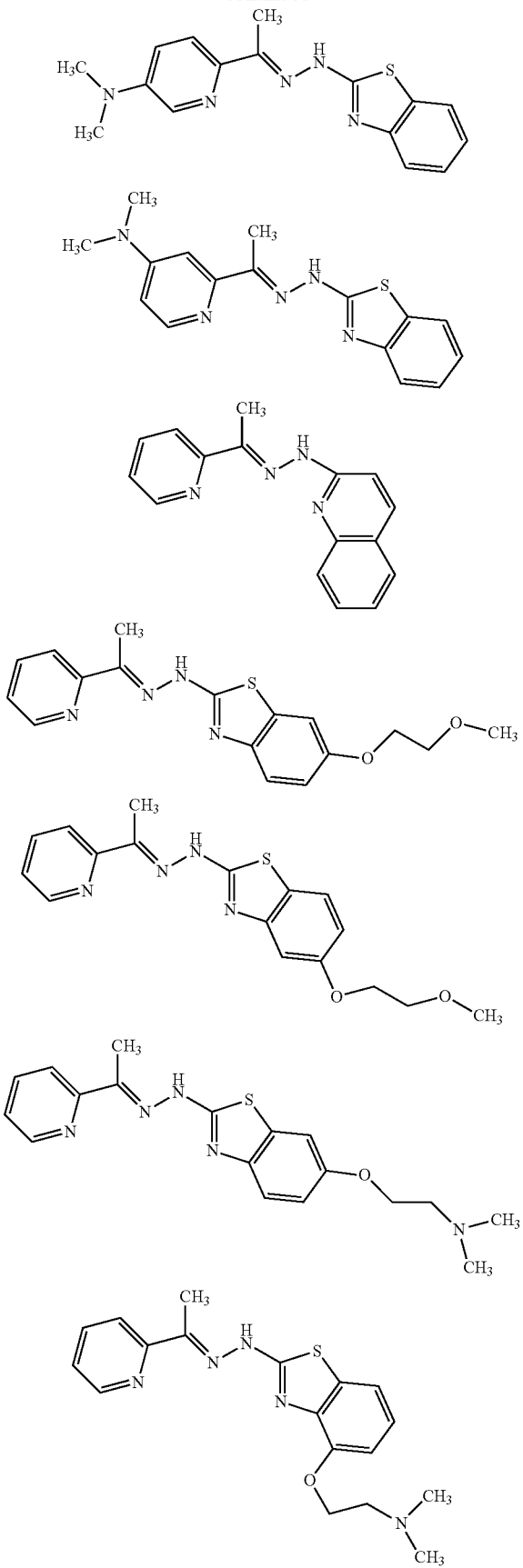
-continued
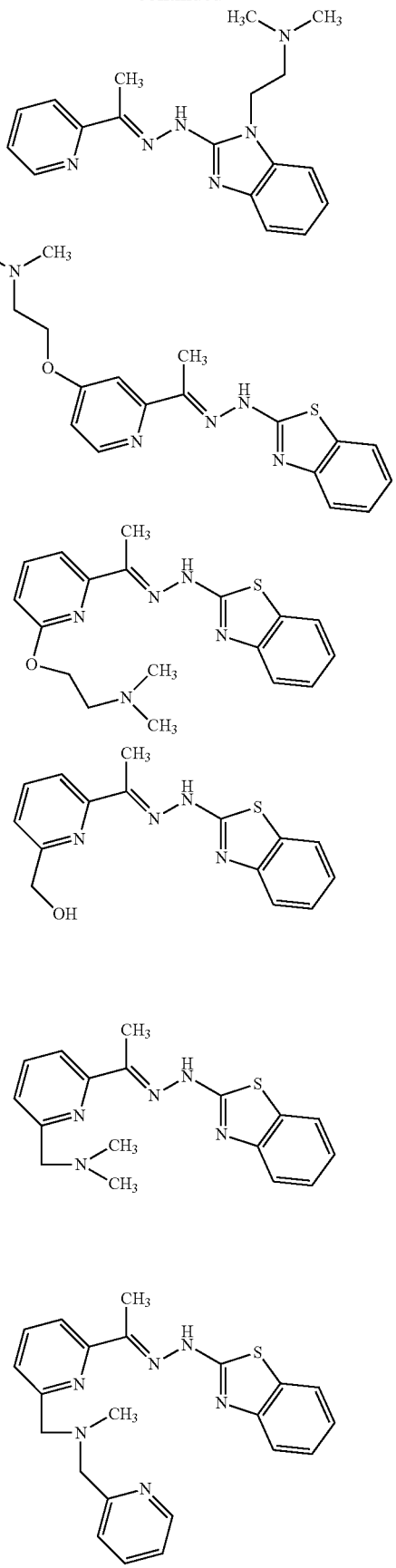

-continued
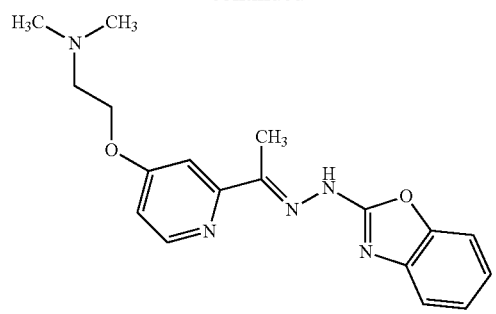
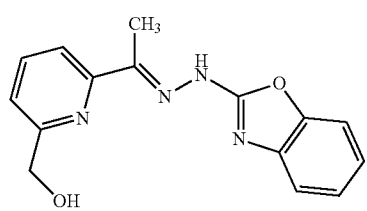
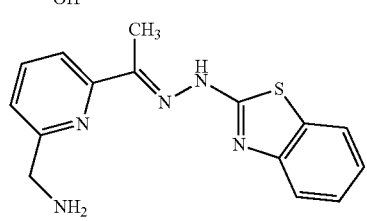
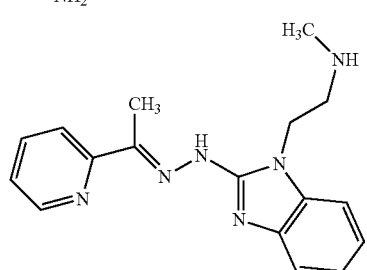
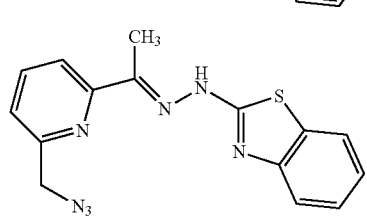
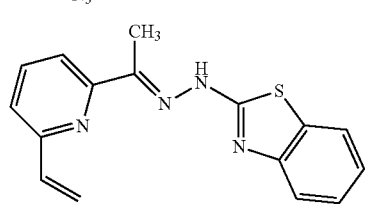
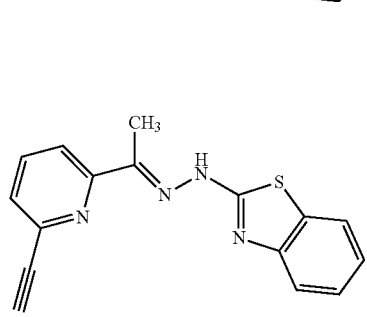
-continued
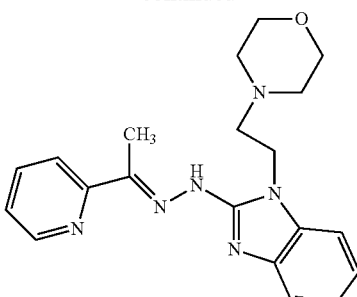
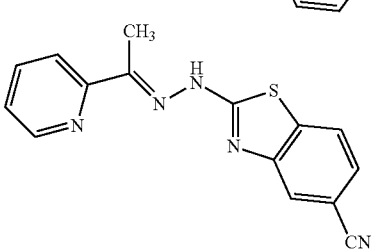
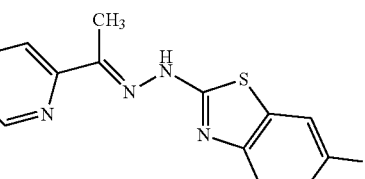
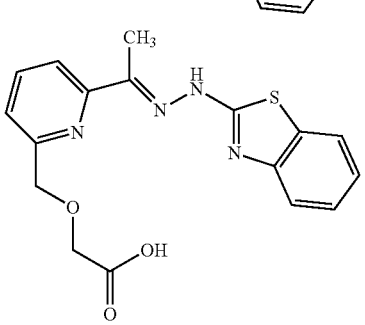
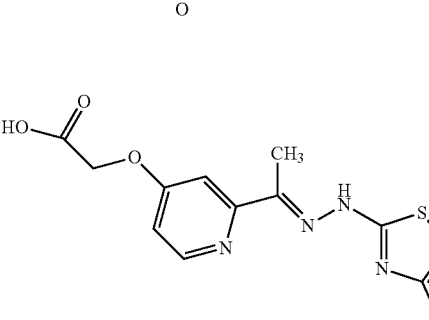
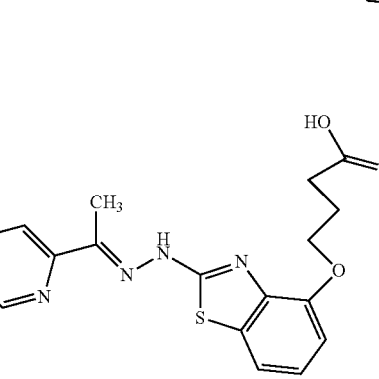

-continued

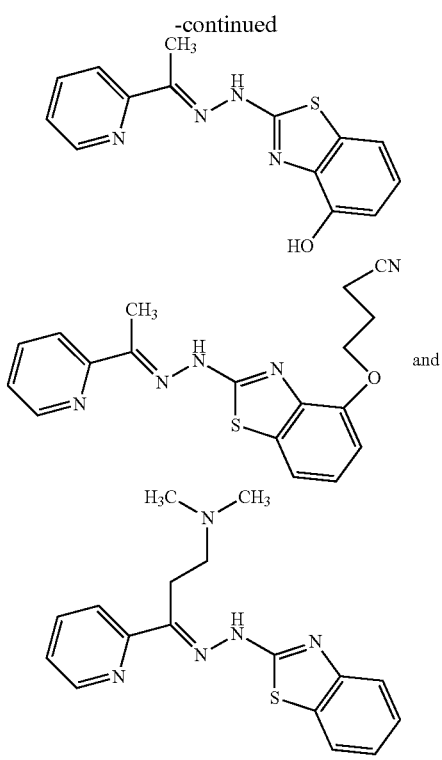

or a salt thereof.

12. A pharmaceutical composition, comprising a compound of claim 1 or a pharmaceutically acceptable salt thereof, and a pharmaceutically acceptable carrier.

13. An injectable pharmaceutical formulation comprising, a compound of claim 1 or a pharmaceutically acceptable salt thereof, and a pharmaceutically acceptable carrier.

14. The compound:

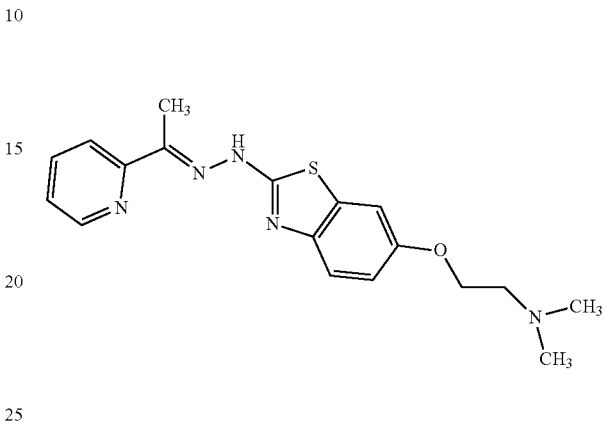

or a salt thereof.

* * * * *

UNITED STATES PATENT AND TRADEMARK OFFICE
CERTIFICATE OF CORRECTION

PATENT NO. : 10,828,288 B2  
APPLICATION NO. : 15/545971  
DATED : November 10, 2020  
INVENTOR(S) : David J. Augeri et al.

Page 1 of 1

It is certified that error appears in the above-identified patent and that said Letters Patent is hereby corrected as shown below:

On the Title Page

Item (56), please delete duplicate publication "Agrawal, et al., "Potential antitumor agents. 13. 4-Methyl-5-amino-1-formylisoquinoline thiosemicarbazone", Journal of Medicinal Chemistry 19(7), 970-972 (1976).";

In the Claims

Column 77, Lines 26-41, Claim 10, please delete " 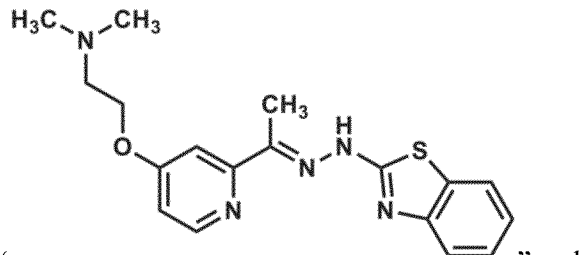 " and insert -- 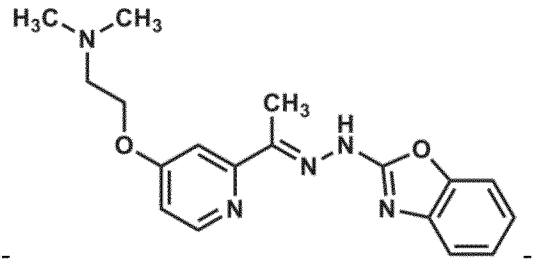 -- therefor.

Signed and Sealed this  
Twenty-third Day of February, 2021

Drew Hirshfeld  
*Performing the Functions and Duties of the  
Under Secretary of Commerce for Intellectual Property and  
Director of the United States Patent and Trademark Office*